US011708612B2

(12) United States Patent
Bild et al.

(10) Patent No.: US 11,708,612 B2
(45) Date of Patent: Jul. 25, 2023

(54) BIOMARKERS FOR CANCER IMMUNOTHERAPY OUTCOMES

(71) Applicant: City of Hope, Duarte, CA (US)

(72) Inventors: Andrea Bild, South Pasadena, CA (US); Jason I. Griffiths, St. Helens (GB)

(73) Assignee: NATIONAL INSTITUTES OF HEALTH (NIH), U.S. DEPT. OF HEALTH AND HUMAN SERVICES (DHHS), U.S. GOVERNMENT, Bethesda, MD (US)

( * ) Notice: Subject to any disclaimer, the term of this patent is extended or adjusted under 35 U.S.C. 154(b) by 23 days.

(21) Appl. No.: 17/110,067

(22) Filed: Dec. 2, 2020

(65) Prior Publication Data
US 2021/0164054 A1     Jun. 3, 2021

Related U.S. Application Data

(60) Provisional application No. 62/942,714, filed on Dec. 2, 2019.

(51) Int. Cl.
| | | |
|---|---|---|
| *C12Q 1/6886* | (2018.01) | |
| *C07K 16/28* | (2006.01) | |
| *G01N 33/574* | (2006.01) | |

(52) U.S. Cl.
CPC ........ *C12Q 1/6886* (2013.01); *C07K 16/2818* (2013.01); *G01N 33/574* (2013.01); *C12Q 2600/106* (2013.01); *C12Q 2600/158* (2013.01)

(58) Field of Classification Search
CPC .................................................. C12Q 1/6886
USPC ...................................................... 424/133.1
See application file for complete search history.

(56) References Cited

PUBLICATIONS

Tockman et al (Cancer Res., 1992, 52:2711s-2718s).*
Motoshima et al (Oncology Letters, 2016, 11: 1911-1916).*
Chittezhath et al (Immunity, 2014, 41: 815-829).*
Schauer et al (Oncoimmunology, 2016, e1160185, 1-13).*
Yi et al (Molecular Cancer, 2018, 17(129): 1-14).*
Ansell, S. M. et al. (Jan. 22, 2015, e-published Dec. 6, 2014). "PD-1 blockade with nivolumab in relapsed or refractory Hodgkin's lymphoma," N Engl J Med 372(4):311-319.
Ayers, M. et al. (Aug. 1, 2017, "IFN-γ-related mRNA profile predicts clinical response to PD-1 blockade," J Clin Invest 127:2930-2940.
Azizi, E. et al. (Aug. 23, 2018, e-published Jun. 28, 2018). "Single-Cell Map of Diverse Immune Phenotypes in the Breast Tumor Microenvironment," *Cell* 174(5):1293-1308.
Barbie, D.A. et al. (Nov. 5, 2009, e-published Oct. 21, 2009). "Systematic RNA interference reveals that oncogenic KRAS-driven cancers require TBK1," Nature 462(7269):108-112.
Bischl, B. mlr: Machine Learning in R. Journal of Machine Learning Research 17 (2016):1-5.
Butler, A. et al. Jun. 2018, e-published Apr. 2, 2018). "Integrating single-cell transcriptomic data across different conditions, technologies, and species," *Nat Biotechnol* 36(5): 411-420.
Carbone, D. P. et al. (Jun. 22, 2017). "First-Line Nivolumab in Stage IV or Recurrent Non-Small-Cell Lung Cancer," N Engl J Med 376(25):2415-2426.
Carpenter, B. et al. (Jan. 2017). "Stan: A Probabilistic Programming Language," Journal of Statistical Software 76(1), 32 pages.
De Simone, M. et al. (Nov. 15, 2016). "Transcriptional Landscape of Human Tissue Lymphocytes Unveils Uniqueness of Tumor-Infiltrating T Regulatory Cells," Immunity 45(5):1135-1147.
Dobin, A. et al. (Jan. 2013, e-published Oct. 25, 2012). "STAR: ultrafast universal RNA-seq aligner," Bioinformatics 29(1):15-21.
Dosset, M. et al. (Mar. 15, 2018). "PD-1/PD-L1 pathway: an adaptive immune resistance mechanism to immunogenic chemotherapy in colorectal cancer," *Oncoimmunology* 7(6): e1433981.
Finak, G. et al. (2015). "MAST: a flexible statistical framework for assessing transcriptional changes and characterizing heterogeneity in single-cell RNA sequencing data," Genome Biology 16, 278.
Garon, E. B. et al. (May 21, 2015, e-published Apr. 19, 2015). "Pembrolizumab for the treatment of non-small-cell lung cancer," N Engl J Med 372(21):2018-2028.
Garris, C. S. et al. (Dec. 18, 2018, e-published Dec. 11, 2018). "Successful Anti-PD-1 Cancer Immunotherapy Requires T Cell-Dendritic Cell Crosstalk Involving the Cytokines IFN-gammaand IL-12," *Immunity* 49, 1148-1161 e1147.
Grosso, J. et al. (2013). "Association of tumor PD-L1 expression and immune biomarkers with clinical activity in patients (pts) with advanced solid tumors treated with nivolumab (anti-PD-1; BMS-936558; ONO-4538)" Journal of Clinical Oncology 31(15):3016-3016.
Hamid, O. et al. (Jul. 11, 2013, e-published Jun. 2, 2013). Safety and tumor responses with lambrolizumab (anti-PD-1) in melanoma. N Engl J Med 369(2):134-144.
Hanzelmann, S. et al. (Jan. 16, 2013) "GSVA: gene set variation analysis for microarray and RNA-seq data," BMC Bioinformatics 14, 7, doi:10.1186/1471-2105-14-7.
Herbst, R. S. et al. (Nov. 27, 2014). "Predictive correlates of response to the anti-PD-L1 antibody MPDL3280A in cancer patients," Nature 515(7528):563-567.
Huang, A. C. et al. (2017). "T-cell invigoration to tumour burden ratio associated with anti-PD-1 response," Nature 545, 60-65.
Kamphorst, A. O. et al. (May 9, 2017, e-published Apr. 26, 2017). "Proliferation of PD-1 + CD8 T cells in peripheral blood after PD-1-targeted therapy in lung cancer patients," Proc Natl Acad Sci U S A 114, 4993-4998.

(Continued)

*Primary Examiner* — Sean E Aeder
(74) *Attorney, Agent, or Firm* — Mintz Levin Cohn Ferris Glovsky and Popeo, P.C.

(57) ABSTRACT

Provided herein, inter alia, are improved methods and systems of determining immunotherapy response in subjects prior and during treatment. Provided herein are methods of detecting gene expression in T cells and in monocytes as well as measuring relative abundance of particular immune cell populations and determining responsiveness to anticancer immunotherapy.

7 Claims, 43 Drawing Sheets

(56) References Cited

PUBLICATIONS

Krieg, C. et al. (2018). "High-dimensional single-cell analysis predicts response to anti-PD-1 immunotherapy," Nat Med 24, 144-153.

Lawrence, N. (2005). "Probabilistic non-liner component analysis with Gaussian process latent variable models," Journal of Machine Learning Research 6, 1783-1816.

Le, D. T. et al. (2017). "Mismatch repair deficiency predicts response of solid tumors to PD-1 blockade," Science 357, 409-413.

Liberzon, A. et al. "Molecular signatures database (MSigDB) 3.0." Bioinformatics 27, 1739-1740, (2011).

Liberzon, A. et al. "The Molecular Signatures Database (MSigDB) hallmark gene set collection," Cell Syst 1, 417-425, (2015).

Llosa, N. J. et al. "The vigorous immune microenvironment of microsatellite instable colon cancer is balanced by multiple counter-inhibitory checkpoints," Cancer Discov 5, 43-51, (2015).

Loos, M. et al. "Clinical significance and regulation of the costimulatory molecule B7-H1 in pancreatic cancer," Cancer Lett 268, 98-109, (2008).

Lynch, T. J. et al. "Ipilimumab in combination with paclitaxel and carboplatin as first-line treatment in stage IIM/IV non-small-cell lung cancer: results from a randomized, double-blind, multicenter phase II study," J Clin Oncol 30, 2046-2054, (2012).

McInnes, L. et al. UMAP: Uniform Manifold Approximation and Projection for Dimension Reduction. arXiv e-prints (Sep. 21, 2020), 63 pages.

Moon, K. R. et al. Visualizing Transitions and Structure for Biological Data Exploration. bioRxiv, 120378, (2018).

Moon, K. R. Manifold learning-based methods for analyzing single-cell RNA-sequencing data. Current Opinion in Systems Biology 7, 36-46, (2017).

Newman, A. M. et al. Robust enumeration of cell subsets from tissue expression profiles. Nat Methods 12, 453-457, (2015).

Nghiem, P. T. et al. PD-1 Blockade with Pembrolizumab in Advanced Merkel-Cell Carcinoma. N Engl J Med 374, 2542-2552, (2016).

Nomi, T. et al. Clinical significance and therapeutic potential of the programmed death-1 ligand/programmed death-1 pathway in human pancreatic cancer. Clin Cancer Res 13, 2151-2157, (2007).

Ohigashi, Y. et al. Clinical significance of programmed death-1 ligand-1 and programmed death-1 ligand-2 expression in human esophageal cancer. Clin Cancer Res 11, 2947-2953, (2005).

Oki, E. et al. Protein Expression of Programmed Death 1 Ligand 1 and HER2 in Gastric Carcinoma. Oncology 93, 387-394, (2017).

Palma, M. et al. T cells in chronic lymphocytic leukemia display dysregulated expression of immune checkpoints and activation markers. Haematologica 102, 562-572, (2017).

Palucka, A. K. et al.The Basis of Oncoimmunology. Cell 164, 1233-1247, (2016).

Peguillet, I. et al. High numbers of differentiated effector CD4 T cells are found in patients with cancer and correlate with clinical response after neoadjuvant therapy of breast cancer. Cancer Res 74, 2204-2216, (2014).

Powles, T. et al. MPDL3280A (anti-PD-L1) treatment leads to clinical activity in metastatic bladder cancer. Nature 515, 558-562, (2014).

Reading, J. L. et al. Too Much of a Good Thing? Chronic IFN Fuels Resistance to Cancer Immunotherapy. Immunity 45, 1181-1183, (2016).

Reck, M. et al. Ipilimumab in combination with paclitaxel and carboplatin as first-line therapy in extensive-disease-small-cell lung cancer: results from a randomized, double-blind, multicenter phase 2 trial. Ann Oncol 24, 75-83, (2013).

Rinder, H. M. et al. Activated and unactivated platelet adhesion to monocytes and neutrophils. Blood 78, 1760-1769 (1991).

Risso, D. et al. A general and flexible method for signal extraction from single-cell RNA-seq data. Nat Commun 9, 284, (2018).

Rizvi, N. A. et al. Mutational landscape determines sensitivity to PD-1 blockade in non-small cell lung cancer. Science 348, 124-128, (2015).

Sade-Feldman, M. et al. Defining T Cell States Associated with Response to Checkpoint Immunotherapy in Melanoma. Cell 175, 998-1013 e1020, (2018).

Samstein, R. M. et al. Tumor mutational load predicts survival after immunotherapy across multiple cancer types. Nat Genet 51, 202-206, (2019).

Schroder, K. et al. Interferon-gamma: an overview of signals, mechanisms and functions. J Leukoc Biol 75, 163-189, (2004).

Sharma, P. et al. Primary, Adaptive, and Acquired Resistance to Cancer Immunotherapy. Cell 168, 707-723, (2017).

Shen et al. (Jun. 1, 2015). ASSIGN: context-specific genomic profiling of multiple heterogeneous biological pathways Bioinformatics 31(11):1745-1753.

Shi, C. et al. Monocyte recruitment during infection and inflammation. Nat Rev Immunol 11, 762-774, (2011).

Shi, J. et al. PD-1 Controls Follicular T Helper Cell Positioning and Function. Immunity 49, 264-274 e264, (2018).

Song, M. et al. PTEN loss increases PD-L1 protein expression and affects the correlation between PD-L1 expression and clinical parameters in colorectal cancer. PLoS One 8, e65821, (2013).

Tirosh, I. et al. Dissecting the multicellular ecosystem of metastatic melanoma by single-cell RNA-seq. Science 352, 189-196, (2016).

Topalian, S. L. et al. Safety, activity, and immune correlates of anti-PD-1 antibody in cancer N Engl J Med 366, 2443-2454, (2012).

Van Dijk, D. et al. Recovering Gene Interactions from Single-Cell Data Using Data Diffusion. Cell 174, 716-729 e727, (2018).

Verma, R. et al. Lymphocyte depletion and repopulation after chemotherapy for primary breast cancer. Breast Cancer Res 18, 10, (2016).

Wang, Y. et al. Negative feedback regulation of IFN-gamma pathway by IFN regulatory factor 2 in esophageal cancers. Cancer Res 68, 1136-1143, (2008).

Wang, L. et al. Clinical significance of B7-H1 and B7-1 expressions in pancreatic carcinoma. World J Surg 34, 1059-1065, (2010).

Wherry, E. J. (2011). T cell exhaustion. Nat Immunol 12, 492-499.

Yang, P. et al. Peripheral CD4+ naive/memory ratio is an independent predictor of survival in non-small cell lung cancer. Oncotarget 8, 83650-83659, (2017).

Ye, Y. et al. Interaction of B7-H1 on intrahepatic cholangiocarcinoma cells with PD-1 on tumor-infiltrating T cells as a mechanism of immune evasion. J Surg Oncol 100, 500-504, (2009).

Yuan, Y. et al. Complete regression of cutaneous metastases with systemic immune response in a patient with triple negative breast cancer receiving p53MVA vaccine with pembrolizumab. Oncoimmunology 6, e1363138, (2017).

Zhang, M. Y. et al. Expression of Bcl-2, PD-L1 and its clinical significance in colorectal cancer. Sichuan Da Xue Xue Bao Yi Xue Ban 43, 827-829, 859 (2012). Translation of Abstract only.

\* cited by examiner

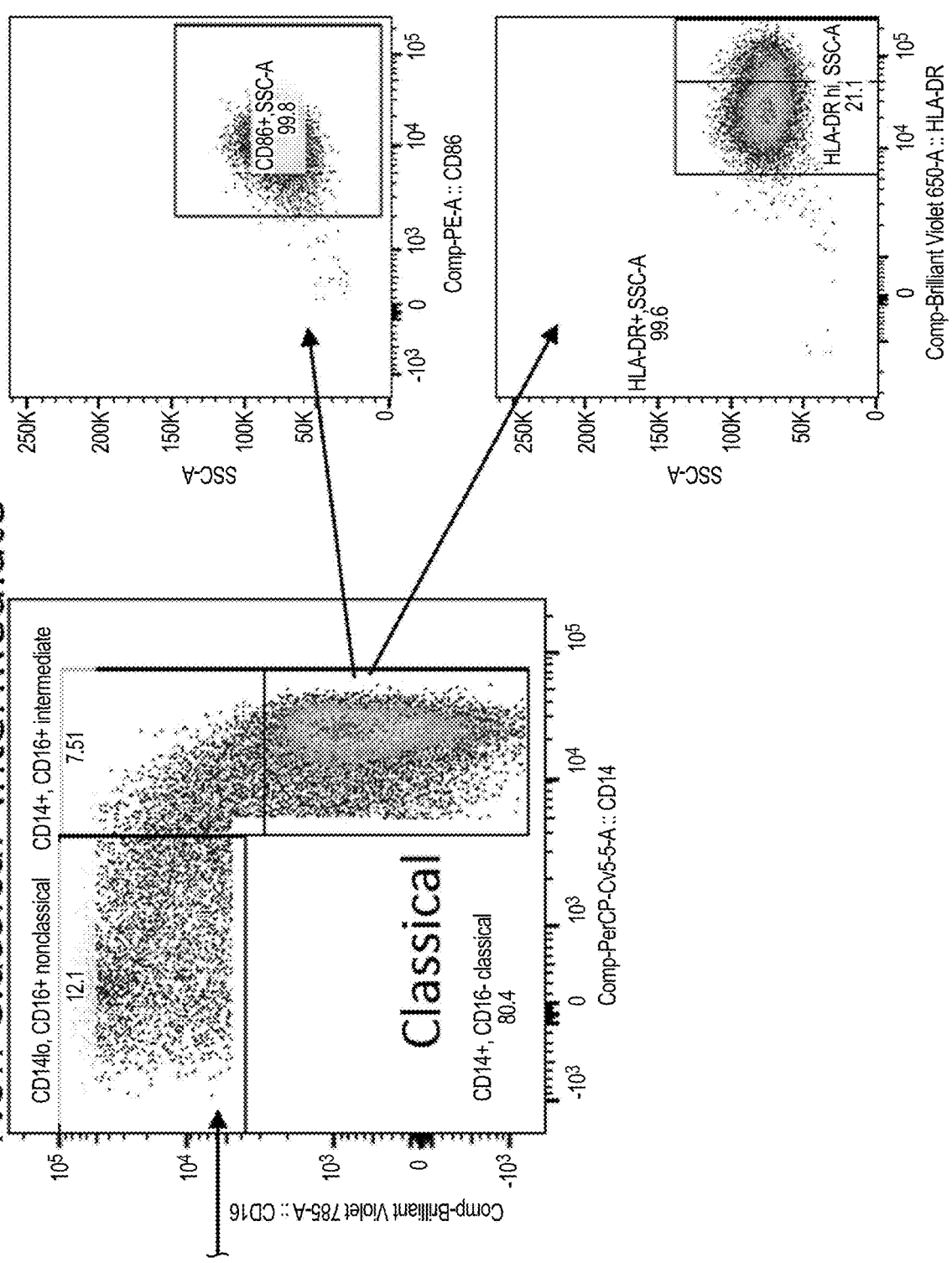

To FIG. 9F-2

BIOMARKERS FOR CANCER IMMUNOTHERAPY OUTCOMES

CROSS REFERENCE TO RELATED APPLICATIONS

This application claims priority to U.S. Provisional Application No. 62/942,714, filed Dec. 2, 2019, which is hereby incorporated by reference in its entirety and for all purposes.

STATEMENT AS TO RIGHTS TO INVENTIONS MADE UNDER FEDERALLY SPONSORED RESEARCH AND DEVELOPMENT

This invention was made with government support under U54 CA209978 awarded by the National Institutes of Health. The government has certain rights in the invention.

BACKGROUND

Immune checkpoint inhibitors treat a wide range of cancers and work by strengthening the immune system's ability to fight tumor cells. Current therapies may include monoclonal antibodies that target immune inhibitory pathways, which regulate immune activity and are frequently co-opted by cancer cells to prevent tumor recognition. One such pathway is the programmed cell death protein 1 (PD-1) pathway. Increased expression of the programmed death-ligand 1 (PD-L1) by cancer cells or tumor-associated cells allows immune escape by inhibiting proliferation, survival, and effector functions of T lymphocytes. In many cancers, including gastrointestinal (GI), PD-L1 expression has been correlated with poor prognosis. Immunotherapies using PD-1 inhibitors or PD-L1 blockade attempt to antagonize cancer-mediated immune suppression and have shown significant clinical benefits for some patients. Various immunotherapy regimens have been developed to bolster the immune system, including its combined administration with chemotherapy. Chemotherapy-induced cancer cell death releases tumor-specific antigens, promoting antigen presentation to the adaptive immune system, while immunotherapy is expected to increase the number and tumor infiltration of cytotoxic (CD8$^+$) T cells and thereby tumor cell death. A regimen which begins immunotherapy after chemotherapy resulted in substantially improved progression-free survival (PFS) compared with chemotherapy alone or immunotherapy concomitant with chemotherapy in small cell lung cancer.

Immunotherapy effectiveness depends on multiple factors including neo-antigen creation and tumor mutational load, tumor infiltration by cytotoxic T-cells, effector immune cell signal production, and immune crosstalk. However, the clinical response to immune checkpoint inhibitors varies widely across patients, with approximately 40% of patients showing no beneficial response at treatment end. Many studies have assessed tumor cells and tumor-associated immune cells for biomarkers of response to immunotherapy. PD-L1 expression, tumor mutation burden, gene expression have been suggested as predictive markers of immunotherapy response, but these tests require invasive collection of tumor tissue which can be challenging to obtain on all patients and over time. The frequency of specific monocyte cell types in the peripheral blood has been recently suggested as a non-invasive pre-treatment indicator of melanoma cancer patient response to immunotherapy, with a higher frequency of classical monocytes predicting improved PFS and overall survival. However, it is unclear whether circulating immune cells can serve as a surrogate measurement of tumor response to therapy given that these cells are not collected when physically in the tumor microenvironment. Further, it is unknown whether the numbers and phenotypes of circulating immune cells, as well as their evolution during treatment, can predict treatment success non-invasively prior to or soon after the initiation of therapy.

BRIEF SUMMARY

In view of the foregoing, there is a need for improved methods of determining immunotherapy response in subjects prior to and during treatment. The present disclosure addresses this need, and provides additional benefits as well.

In an aspect, provided herein are methods including detecting one or more parameters in a sample of peripheral blood from a subject with cancer, including detecting (i) gene expression in monocytes including (1) increased expression of one or more of NFKB1, MYD88, NFKBIA or NFKBIZ, (2) decreased expression of IKBKB, (3) increased expression of one or more of growth factor genes, and/or (4) increased expression of one or more TNF genes, compared to a control; (ii) a greater number of CD8+ differentiated cells, a greater number of CD4+ naive cells, fewer CD4+ differentiated cells, and/or fewer T follicular helper ($T_{FH}$) cells compared to a control; or (iii) a lower density of total peripheral blood mononuclear cells, a lower density of CD4+ effector memory (EM) cells, and/or a higher density of classical monocytes compared to a control.

In an aspect, provided herein are methods of identifying a cancer of a subject as responsive to treatment with a PD-1 inhibitor, the method comprising detecting one or more parameters in a sample of peripheral blood from the subject, including detecting (i) gene expression in monocytes comprising (1) increased expression of one or more of NFKB1, MYD88, NFKBIA or NFKBIZ, (2) decreased expression of IKBKB, (3) increased expression of one or more of growth factor genes, and/or (4) increased expression of one or more TNF genes, compared to a control; (ii) greater number of CD8+ differentiated cells, a greater number of CD4+ naive cells, fewer CD4+ differentiated cells, and/or fewer T follicular helper ($T_{FH}$) cells compared to a control; or (iii) a lower density of total peripheral blood mononuclear cells, a lower density of CD4+ effector memory (EM) cells, and/or a higher density of classical monocytes compared to a control.

In an aspect, provided herein is a method for treating cancer in a subject including detecting one or more parameters in a sample of peripheral blood from the subject, including detecting (i) gene expression in monocytes including (1) increased expression of one or more of NFKB1, MYD88, NFKBIA or NFKBIZ, (2) decreased expression of IKBKB, (3) increased expression of one or more of growth factor genes, and/or (4) increased expression of one or more TNF genes, compared to a control; (ii) a greater number of CD8+ differentiated cells, a greater number of CD4+ naive cells, fewer CD4+ differentiated cells, and/or fewer T follicular helper ($T_{FH}$) cells compared to a control; or (iii) a lower density of total peripheral blood mononuclear cells, a lower density of CD4+ effector memory (EM) cells, and/or a higher density of classical monocytes compared to a control; and identifying the cancer as responsive to treatment with a PD-1 inhibitor if the cancer has one or more of the parameters (i)-(iii).

In an aspect, provided herein is a method including detecting one or more parameters in a sample of peripheral blood from a subject with cancer previously treated with a PD-1 inhibitor, including detecting (i) in T cells, (1) increased expression of one or more interferon type I or type II signaling genes, (2) increased expression of one or more of NFKB1, MYD88, NFKBIA or NFKBIZ, (3) increased expression of one or more major histocompatibility complex (MHC) class I or class II processing genes, (4) increased expression of one or more of CCL3, CCL4, CCL5, and CCR5, (5) decreased expression of one or more of CXCR3 or CCR2 genes, (6) increased expression in CD8+ T cells of one or more cell death genes, (7) a greater number of differentiated CD8+ cells, and/or (8) fewer differentiated CD4+ cells compared to a control; or (ii) in monocytes, (1) increased expression of genes upregulated by IFN stimulation, and/or (2) increased expression of genes upregulated by major histocompatibility complex 2 (MHCII) production.

In an aspect, provided herein is a method of identifying a cancer of a subject previously treated with a PD-1 inhibitor as responsive to treatment with the PD-1 inhibitor, the method including detecting one or more parameters in a sample of peripheral blood from the subject, including detecting (i) in T cells, (1) increased expression of one or more interferon type I or type II signaling genes, (2) increased expression one or more of NFKB1, MYD88, NFKBIA or NFKBIZ, (3) increased expression of one or more major histocompatibility complex (MHC) class I or class II processing genes, (4) increased expression of one or more of CCL3, CCL4, CCL5, and CCR5, (5) decreased expression of one or more of CXCR3 or CCR2 genes, (6) increased expression in CD8+ T cells of one or more cell death genes, (7) a greater number of differentiated CD8+ cells, and/or (8) fewer differentiated CD4+ cells compared to a control; or (ii) in monocytes, (1) increased expression of genes upregulated by IFN stimulation, and/or (2) increased expression of genes upregulated by major histocompatibility complex 2 (MHCII) production.

In an aspect, provided herein is a method of monitoring response to PD-1 immunotherapy in a subject previously treated with a PD-1 inhibitor, the method including detecting (i) in T cells, (1) increased expression of one or more interferon (IFN) type I or type II signaling genes, (2) increased expression one or more of NFKB1, MYD88, NFKBIA or NFKBIZ, (3) increased expression of one or more major histocompatibility complex (MHC) class I or class II processing genes, (4) increased expression of one or more of CCL3, CCL4, CCL5, and CCR5, (5) decreased expression of one or more of CXCR3 or CCR2 genes, (6) increased expression in CD8+ T cells of one or more cell death genes, (7) a greater number of differentiated CD8+ cells, and/or (8) fewer differentiated CD4+ cells compared to a control; or (ii) in monocytes, (1) increased expression of genes upregulated by IFN stimulation, and/or (2) increased expression of genes upregulated by major histocompatibility complex 2 (MHCII) production; and identifying the cancer as responsive to continued treatment with the PD-1 inhibitor if one or both of parameters (i) and (ii) are detected.

In an aspect, provided herein is a method of monitoring response to PD-1 immunotherapy in a subject previously treated with a PD-1 inhibitor, the method including: (a) detecting an increase in peripheral blood mononuclear cells (PBMCs) in a sample of peripheral blood from the subject compared to a control; (b) detecting a reduced rate of tumor growth compared to a control, comprising measuring tumor size and/or a level of one or more tumor antigens; and (c) identifying the cancer as responsive to continued treatment with the PD-1 inhibitor if both of parameters (a) and (b) are detected.

In an aspect, provided herein is a system including at least one processor; and at least one memory including program code which when executed by the at least one memory provides operations for performing a method as described herein.

BRIEF DESCRIPTION OF THE DRAWINGS

FIG. 3A are graphs showing differences in interferon (IFN) and inflammatory signaling of CD4$^+$ and CD8$^+$ T cells of responders and non-responders, showing overall trends of pathways within each cellular process (solid lines) and variation (shaded regions). Individual GSEA pathways exhibiting differential trends in expression patterns between responders and non-responders are indicated by dashed lines, over C1, C2, and C3 timepoints. FIG. 3B is a heatmap of changes in gene expression of responder and non-responder CD4$^+$ and CD8$^+$ T cells over time. Interferon (IFN), cell death, NF-KB, MHC (major histocompatibility complex) I & II and migration signature genes are displayed as the proportion of maximum level of each gene. Genes not detected in a cell type are shaded grey. FIG. 3C are graphs showing the differences in inflammatory signaling, differentiation and growth factor production between the monocytes of responders and non-responders showing overall trends of pathways within each cellular process (solid lines) and variation (shaded regions). The trends of pathways exhibiting differential expression patterns in responders and non-responders are indicated by dashed lines. FIG. 3D is a heatmap displaying the changes in gene expression of responder and non-responder monocytes over time. Interferon, cell death, NF-κB, TNF-α, growth factors production, and migration signature genes are displayed as the proportion of maximum level of each gene, where C stands for cycle, 1 cycle is 14 days, C1 is the baseline, C3 is the chemotherapy mFOLOFX6 regimen, and C5 is chemotherapy including anti PD-1 immunotherapy.

FIG. 12A corresponds to clusters published by Azizi et al. [30]. FIG. 12B corresponds to clusters published by Sade-Feldman et al. [29].

FIGS. 13B-13C (machine learning prediction): Connection of immune cells types identified in public datasets and those predicted for the PD-1 dataset clusters, by applying a Random Forest learning algorithm to the patient cohort as a training set. FIGS. 13D-13E (Shared marker genes): Connections of the number of shared genes between public datasets and our cohort clusters. In FIGS. 13B-13E, the top row corresponds to cluster published by Azizi et al. while the bottom row corresponds to cluster published by Sade-Feldman et al.

Figure 22:
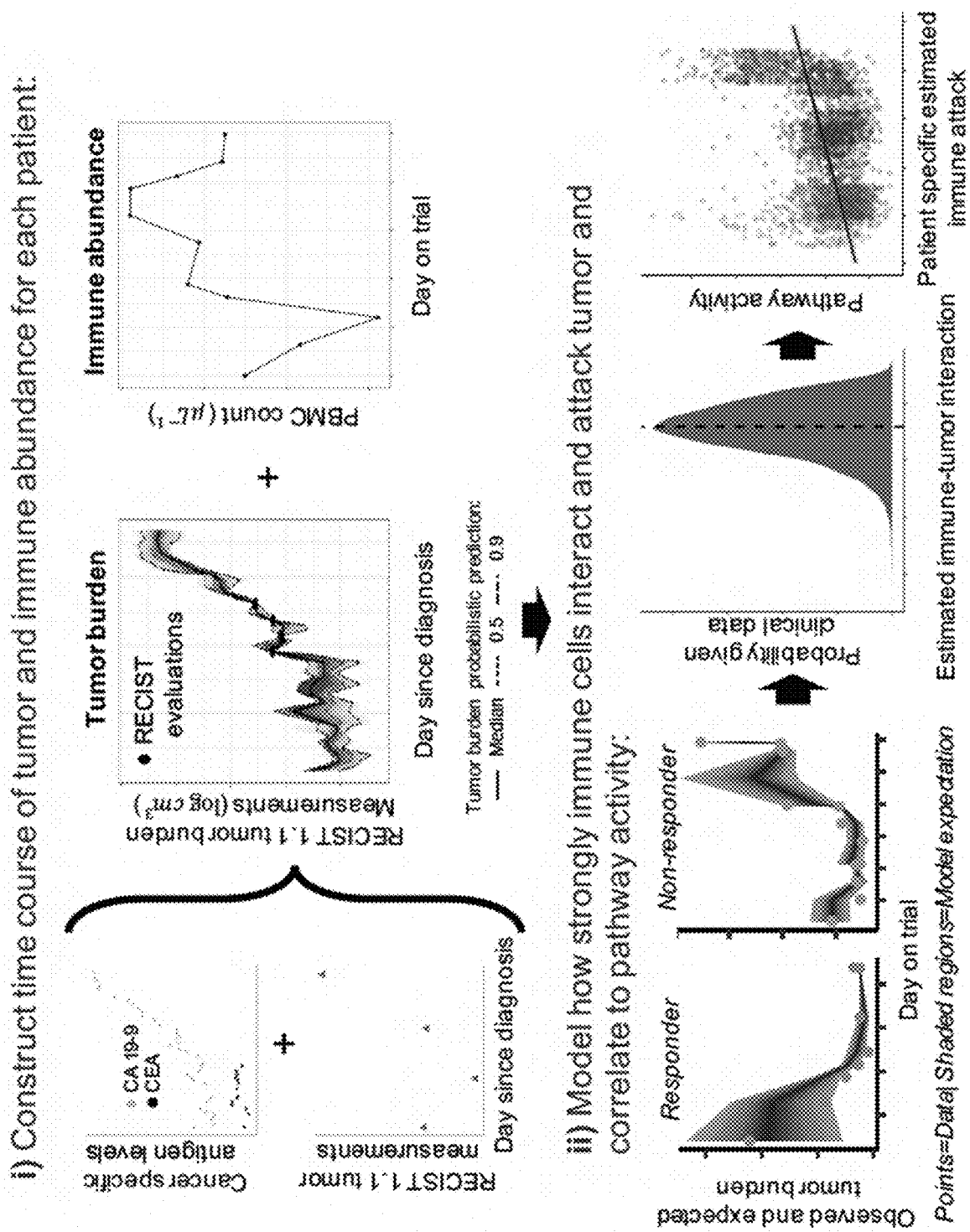

FIG. 22 illustrates a mathematical model flowchart of tumor-immune cell interactions.

Figure 23:
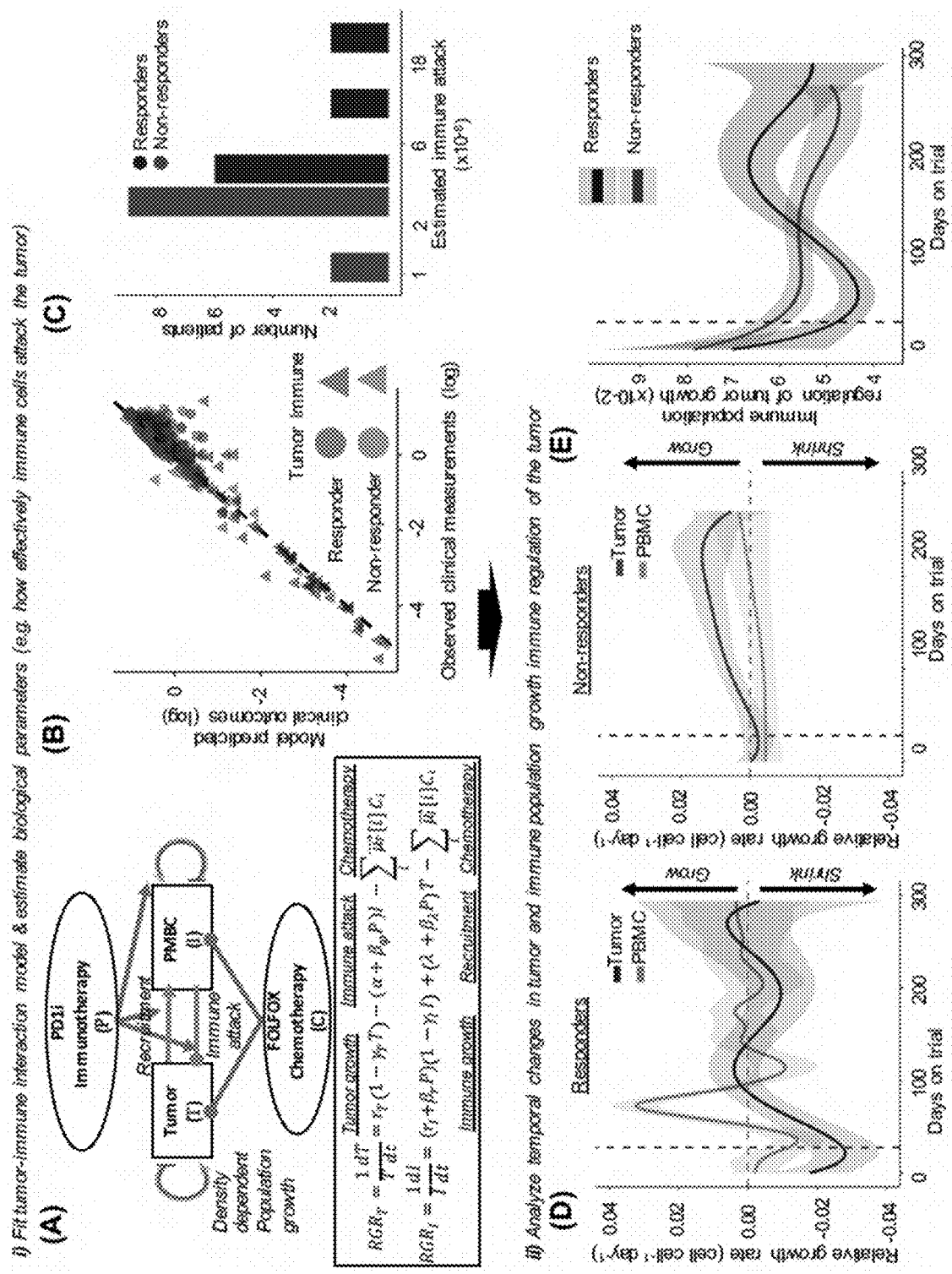

FIG. 23 illustrates a model and estimate of biological parameters for determining tumor response, and example data.

DETAILED DESCRIPTION

The practice of the technology described herein will employ, unless indicated specifically to the contrary, conventional methods of chemistry, biochemistry, organic chemistry, molecular biology, microbiology, recombinant DNA techniques, genetics, immunology, and cell biology that are within the skill of the art, many of which are described below for the purpose of illustration. Examples of such techniques are available in the literature. [See for example Refs. 61-68]

All patents, patent applications, articles and publications mentioned herein, both supra and infra, are hereby expressly incorporated herein by reference in their entireties.

Unless defined otherwise herein, all technical and scientific terms used herein have the same meaning as commonly understood by one of ordinary skill in the art to which this disclosure belongs. Various scientific dictionaries that include the terms included herein are well known and available to those in the art. Although any methods and materials similar or equivalent to those described herein find use in the practice or testing of the disclosure, some preferred methods and materials are described. Accordingly, the terms defined immediately below are more fully described by reference to the specification as a whole. It is to be understood that this disclosure is not limited to the particular methodology, protocols, and reagents described, as these may vary, depending upon the context in which they are used by those of skill in the art.

As used herein, the singular terms "a", "an", and "the" include the plural reference unless the context clearly indicates otherwise.

Reference throughout this specification to, for example, "one embodiment", "an embodiment", "another embodiment", "a particular embodiment", "a related embodiment", "a certain embodiment", "an additional embodiment", or "a further embodiment" or combinations thereof means that a particular feature, structure or characteristic described in connection with the embodiment is included in at least one embodiment of the present disclosure. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

The terms "disease" or "condition" refer to a state of being or health status of a patient or subject capable of being diagnosed and/or treated with compounds or methods provided herein. The disease may be a cancer.

As used herein, the term "cancer" refers to all types of cancer, neoplasm or malignant tumors found in mammals (e.g. humans), including leukemias, lymphomas, carcinomas and sarcomas. Examples of cancers that may be diagnosed and/or treated with a compound or method provided herein include brain cancer, glioma, glioblastoma, neuroblastoma, prostate cancer, colorectal cancer, pancreatic cancer, Medulloblastoma, melanoma, cervical cancer, gastric cancer, ovarian cancer, lung cancer, cancer of the head, Hodgkin's Disease, and Non-Hodgkin's Lymphomas. Example cancers that may be diagnosed and/or treated with a compound or method provided herein include cancer of the thyroid, endocrine system, brain, breast, cervix, colon, head & neck, liver, kidney, lung, ovary, pancreas, rectum, stomach, and uterus. Additional examples include, thyroid carcinoma, cholangiocarcinoma, pancreatic adenocarcinoma, skin cutaneous melanoma, colon adenocarcinoma, rectum adenocarcinoma, stomach adenocarcinoma, esophageal carcinoma, head and neck squamous cell carcinoma, breast invasive carcinoma, lung adenocarcinoma, lung squamous cell carcinoma, non-small cell lung carcinoma, mesothelioma, multiple myeloma, neuroblastoma, glioma, glioblastoma multiforme, ovarian cancer, rhabdomyosarcoma, primary thrombocytosis, primary macroglobulinemia, primary brain tumors, malignant pancreatic insulanoma, malignant carcinoid, urinary bladder cancer, premalignant skin lesions, testicular cancer, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer. In embodiments, the cancer is gastrointestinal cancer. In embodiments, the cancer is colorectal cancer. In embodiments, the cancer is gastroesophogeal. In embodiments, the cancer is cancer pancreatic cancer. In embodiments, the cancer is biliary cancer.

As used herein, the term "diagnosis" refers to an identification or likelihood of the presence of a particular type of cancer or outcome in a subject. As also used herein, the term "prognosis" refers to the likelihood or risk of a subject developing a particular outcome or particular event.

As used herein, a "biological sample" encompasses essentially any sample type obtained from a subject that can be used in a diagnostic or prognostic method described herein. The biological sample may be any bodily fluid, tissue or any other suitable sample. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as cells (e.g., cancer cells), polypeptides, or proteins. The term "biological sample" encompasses a clinical sample, but also, in some instances, includes cells in culture, cell supernatants, cell lysates, blood, serum, plasma, urine, cerebral spinal fluid, biological fluid, and tissue samples. The sample may be pretreated as necessary by dilution in an appropriate buffer solution or concentrated, if desired. Any of a number of standard aqueous buffer solutions, employing one of a variety of buffers, such as phosphate, Tris, or the like, preferably at physiological pH can be used. Biological samples can be derived from patients using well-known techniques such as venipuncture, lumbar puncture, fluid sample such as saliva or urine, or tissue biopsy and the like. In embodiments, the sample is a cancer sample (e.g., containing or suspected of containing cancer cells, such as from a tumor). In embodiments, the sample is a formalin-fixed, paraffin-embedded (FFPE) sample.

"Treating" or "treatment" as used herein (and as well understood in the art) includes any approach for obtaining beneficial or desired results in a subject's condition, including clinical results. Beneficial or desired clinical results can include, but are not limited to, alleviation or amelioration of one or more symptoms or conditions, diminishment of the extent of a disease, stabilizing (i.e., not worsening) the state of disease, prevention of a disease's transmission or spread, delay or slowing of disease progression, amelioration or palliation of the disease state, diminishment of the reoccurrence of disease, and remission, whether partial or total and whether detectable or undetectable. "Treating" or "treatment" refers to any indicia of success in the therapy or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. In other words, "treatment" as used herein includes any cure, amelioration, or prevention of a disease.

"Treating" or "treatment" as used herein includes prophylactic treatment. Treatment may prevent the disease from occurring; inhibit the disease's spread; relieve the disease's symptoms, fully or partially remove the disease's underlying cause, shorten a disease's duration, or do a combination of these things. The term "treating" and conjugations thereof may include prevention of an injury, pathology, condition, or disease. In embodiments, treating is preventing. In embodiments, treating does not include preventing. Treatment methods include administering to a subject a therapeutically effective amount of an active agent. The administering step may consist of a single administration or may include a series of administrations. The length of the treatment period depends on a variety of factors, such as the severity of the condition, the age of the patient, the concentration of active agent, the activity of the compositions used in the treatment, or a combination thereof. It will also be appreciated that the effective dosage of an agent used for the treatment or prophylaxis may increase or decrease over the course of a particular treatment or prophylaxis regime. Changes in dosage may result and become apparent by diagnostic assays (e.g., assays described herein or known in the art). In some instances, chronic administration may be required. For example, the compositions are administered to the subject in an amount and for a duration sufficient to treat the patient.

The term "prevent" refers to a decrease in the occurrence of disease symptoms in a patient. The prevention may be complete (no detectable symptoms) or partial, such that fewer symptoms are observed than would likely occur absent treatment.

The term "patient" or "subject" refers to a living organism suffering from or prone to a disease or condition that can be treated by administration of a pharmaceutical composition. Non-limiting examples include humans, other mammals, bovines, rats, mice, dogs, monkeys, goat, sheep, cows, deer, and other non-mammalian animals. In some embodiments, a subject is human.

The term "control" or "control experiment" is used in accordance with its plain and ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is a measurement of a reference sample. In some instances, the control is a synthetic quantification standard used as a reference for assay measurements. In embodiments, the control is a reference value obtained for a reference individual or population of individuals having a known condition, such as responsiveness or non-responsiveness to PD-1 inhibitor treatment. In embodiments, the reference individual or population is not responsive to PD-1 inhibitor treatment, and detection of PD-1 inhibitor responsiveness comprises dissimilarity to the control (e.g., an increase or decrease of a particular parameter). In embodiments, the control is a refence value for a sample from the same subject but at a different time, such as at an earlier time (e.g., prior to administering a treatment, such as a PD1 inhibitor).

As described herein, the terms "marker", "protein marker", "polypeptide marker", and "biomarker" are used interchangeably throughout the disclosure. As used herein, a protein marker refers generally to a protein or polypeptide, the level or concentration of which is associated with a particular biological state. In embodiments, the marker is a gene expression marker, changes in which may be detected at the level of transcribed RNA, or translated polypeptide.

The terms "polypeptide," "peptide" and "protein" used interchangeably herein, refer to a polymeric form of amino acids of any length, which can include coded and non-coded amino acids, chemically or biochemically modified or derivatized amino acids, and polypeptides having modified peptide backbones. In various embodiments, detecting the concentrations of naturally occurring protein marker proteins in a biological sample is contemplated for use within diagnostic, prognostic, or monitoring methods disclosed herein. The term also includes fusion proteins, including, but not limited to, naturally occurring fusion proteins with a heterologous amino acid sequence, fusions with heterologous and homologous leader sequences, with or without N-terminal methionine residues; immunologically tagged proteins; and the like. The terms also include polymers that may be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymers. A "fusion protein" refers to a chimeric protein encoding two or more separate protein sequences that are recombinantly expressed as a single moiety.

For specific proteins described herein, the named protein includes any of the protein's naturally occurring forms, variants or homologs that maintain the protein's activity (e.g., within at least 50%, 80%, 90%, 95%, 96%, 97%, 98%, 99% or 100% activity compared to the native protein). In some embodiments, variants or homologs have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring form. Genes and their corresponding proteins are identified by designations commonly used in the art according to their plain and ordinary meaning. Additional information relating to recited gene designations, including sequence information (e.g., DNA, RNA, and amino acid sequences), full names of genes commonly identified by way of acronym, and the like are available in publicly accessible databases known to those skilled in the art, such as databases available from the National Center for Biotechnology Information (www.ncbi.nlm.nih.gov/), including GenBank (www.ncbi.nlm.nih.gov/genbank/) and the NCBI Protein database (www.ncbi.nlm.nih.gov/protein/), and UniProt (www.uniprot.org).

A "substantially isolated" or "isolated" substance is one that is substantially free of its associated surrounding materials in nature. The term "substantially free" is used herein to mean at least 50%, preferably at least 70%, more preferably at least 80%, and even more preferably at least 90% free of the materials with which it is associated in nature. As used herein, "isolated" can refer to polynucleotides, polypeptides, antibodies, cells, samples, and the like.

An "effective amount" is an amount sufficient for a compound to accomplish a stated purpose relative to the absence of the compound (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug is an amount of a drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques.

The term "administering" as used herein refers to oral administration, administration as a suppository, topical contact, intravenous, parenteral, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. In embodiments, the administering does not include administration of any active agent other than the recited active agent.

The term "co-administer" as used herein refers to a composition described herein administered at the same time, just prior to, or just after the administration of one or more additional therapies. The compounds provided herein can be administered alone or can be coadministered to the patient. Co-administration is meant to include simultaneous or sequential administration of the compounds individually or in combination (more than one compound). Thus, the preparations can also be combined, when desired, with other active substances (e.g. to reduce metabolic degradation). The compositions of the present disclosure can be delivered transdermally, by a topical route, or formulated as applicator sticks, solutions, suspensions, emulsions, gels, creams, ointments, pastes, jellies, paints, powders, and aerosols.

The term "cancer model organism" as used herein refers to an organism exhibiting a phenotype indicative of cancer, or the activity of cancer causing elements, within the organism. A wide variety of organisms may serve as cancer model organisms, and include for example, cancer cells and mammalian organisms such as rodents (e.g. mouse or rat) and primates. Cancer cell lines are widely understood by those skilled in the art as cells exhibiting phenotypes or genotypes similar to in vivo cancers. Cancer cell lines as used herein includes cell lines from animals (e.g. mice) and from humans.

The term "anticancer agent" is used in accordance with its plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent identified herein having utility in methods of treating cancer. In some embodiments, an anti-cancer agent is an agent approved by the FDA or similar regulatory agency of a country other than the USA, for treating cancer. Examples of anti-cancer agents include, but are not limited to, MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomusitne, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), or pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002, Syk inhibitors, mTOR inhibitors, antibodies (e.g., rituxan), gossyphol, genasense, polyphenol E, Chlorofusin, all trans-retinoic acid (ATRA), bryostatin, tumor necrosis factor-related apoptosis-inducing ligand (TRAIL), 5-aza-2'-deoxycytidine, all trans retinoic acid, doxorubicin, vincristine, etoposide, gemcitabine, imatinib (Gleevec®), geldanamycin, 17-N-Allylamino-17-Demethoxygeldanamycin (17-AAG), flavopiridol, LY294002, bortezomib, trastuzumab, BAY 11-7082, PKC412, PD184352, 20-epi-1, 25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; daclizimab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylerie conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B 1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofuran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; zinostatin stimalamer, Adriamycin, Dactinomycin, Bleomycin, Vinblastine, Cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; fluorocitabine; fosquidone; fostriecin sodium; gemcitabine; gemcitabine hydrochloride; hydroxyurea; idarubicin hydrochloride; ifosfamide; iimofosine; interleukin (including recombinant interleukin II, or rIL.sub.2), interferon alfa-2a; interferon alfa-2b; interferon alfa-n1; interferon alfa-n3; interferon beta-1a; interferon gamma-1b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazoie; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride, agents that arrest cells in the G2-M phases and/or modulate the formation or stability of microtubules, (e.g. Taxol™ (i.e. paclitaxel), Taxotere™, compounds comprising the taxane skeleton, Erbulozole (i.e. R-55104), Dolastatin 10 (i.e. DLS-10 and NSC-376128), Mivobulin isethionate (i.e. as CI-980), Vincristine, NSC-639829, Discodermolide (i.e. as NVP-XX-A-296), ABT-751 (Abbott, i.e. E-7010), Altorhyrtins (e.g. Altorhyrtin A and Altorhyrtin C), Spongistatins (e.g. Spongistatin 1, Spongistatin 2, Spongistatin 3, Spongistatin 4, Spongistatin 5, Spongistatin 6, Spongistatin 7, Spongistatin 8, and Spongistatin 9), Cemadotin hydrochloride (i.e. LU-103793 and NSC-D-669356), Epothilones (e.g. Epothilone A, Epothilone B, Epothilone C (i.e. desoxyepothilone A or dEpoA), Epothilone D (i.e. KOS-862, dEpoB, and desoxyepothilone B), Epothilone E, Epothilone F, Epothilone B N-oxide, Epothilone A N-oxide, 16-aza-epothilone B, 21-aminoepothilone B (i.e. BMS-310705), 21-hydroxyepothilone D (i.e. Desoxyepothilone F and dEpoF), 26-fluoroepothilone, Auristatin PE (i.e. NSC-654663), Soblidotin (i.e. TZT-1027), LS-4559-P (Pharmacia, i.e. LS-4577), LS-4578 (Pharmacia, i.e. LS-477-P), LS-4477 (Pharmacia), LS-4559 (Pharmacia), RPR-112378 (Aventis), Vincristine sulfate, DZ-3358 (Daiichi), FR-182877 (Fujisawa, i.e. WS-9885B), GS-164 (Takeda), GS-198 (Takeda), KAR-2 (Hungarian Academy of Sciences), BSF-223651 (BASF, i.e. ILX-651 and LU-223651), SAH-49960 (Lilly/Novartis), SDZ-268970 (Lilly/Novartis), AM-97 (Armad/Kyowa Hakko), AM-132 (Armad), AM-138 (Armad/Kyowa Hakko), IDN-5005 (Indena), Cryptophycin 52 (i.e. LY-355703), AC-7739 (Ajinomoto, i.e. AVE-8063A and CS-39.HC1), AC-7700 (Ajinomoto, i.e. AVE-8062, AVE-8062A, CS-39-L-Ser.HCl, and RPR-258062A), Vitilevuamide, Tubulysin A, Canadensol, Centaureidin (i.e. NSC-106969), T-138067 (Tularik, i.e. T-67, TL-138067 and TI-138067), COBRA-1 (Parker Hughes Institute, i.e. DDE-261 and WHI-261), H10 (Kansas State University), H16 (Kansas State University), Oncocidin A1 (i.e. BTO-956 and DIME), DDE-313 (Parker Hughes Institute), Fijianolide B, Laulimalide, SPA-2 (Parker Hughes Institute), SPA-1 (Parker Hughes Institute, i.e. SPIKET-P), 3-IAABU (Cytoskeleton/Mt. Sinai School of Medicine, i.e. MF-569), Narcosine (also known as NSC-5366), Nascapine, D-24851 (Asta Medica), A-105972 (Abbott), Hemiasterlin, 3-BAABU (Cytoskeleton/Mt. Sinai School of Medicine, i.e. MF-191), TMPN (Arizona State University), Vanadocene acetylacetonate, T-138026 (Tularik), Monsatrol, lnanocine (i.e. NSC-698666), 3-IAABE (Cytoskeleton/Mt. Sinai School of Medicine), A-204197 (Abbott), T-607 (Tuiarik, i.e. T-900607), RPR-115781 (Aventis), Eleutherobins (such as Desmethyleleutherobin, Desaetyleleutherobin, Isoeleutherobin A, and Z-Eleutherobin), Caribaeoside, Caribaeolin, Halichondrin B, D-64131 (Asta Medica), D-68144 (Asta Medica), Diazonamide A, A-293620 (Abbott), NPI- 2350 (Nereus), Taccalonolide A, TUB-245 (Aventis), A-259754 (Abbott), Diozostatin, (-)-Phenylahistin (i.e. NSCL-96F037), D-68838 (Asta Medica), D-68836 (Asta Medica), Myoseverin B, D-43411 (Zentaris, i.e. D-81862), A-289099 (Abbott), A-318315 (Abbott), HTI-286 (i.e. SPA-110, trifluoroacetate salt) (Wyeth), D-82317 (Zentaris), D-82318 (Zentaris), SC-12983 (NCI), Resverastatin phosphate sodium, BPR—OY-007 (National Health Research Institutes), and SSR-250411 (Sanofi)), steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, or the like.

As defined herein, the term "activation", "activate", "activating", "activator" and the like in reference to a protein-inhibitor interaction means positively affecting (e.g. increasing) the activity or function of the protein relative to the activity or function of the protein in the absence of the activator. In embodiments activation means positively affecting (e.g. increasing) the concentration or levels of the protein relative to the concentration or level of the protein in the absence of the activator. The terms may reference activation, or activating, sensitizing, or up-regulating signal transduction or enzymatic activity or the amount of a protein decreased in a disease. Thus, activation may include, at least in part, partially or totally increasing stimulation, increasing or enabling activation, or activating, sensitizing, or up-regulating signal transduction or enzymatic activity or the amount of a protein which is decreased in a disease relative to a non-diseased control). Activation may include, at least in part, partially or totally increasing stimulation, increasing or enabling activation, or activating, sensitizing, or up-regulating signal transduction or enzymatic activity or the amount of a protein The terms "agonist," "activator," "upregulator," etc. refer to a substance capable of detectably increasing the expression or activity of a given gene or protein. The agonist can increase expression or activity 10%, 20%, 30%, 40%, 50%, 60%, 70%, 80%, 90% or more in comparison to a control in the absence of the agonist. In certain instances, expression or activity is 1.5-fold, 2-fold, 3-fold, 4-fold, 5-fold, 10-fold or higher than the expression or activity in the absence of the agonist.

As defined herein, the term "inhibition", "inhibit", "inhibiting" and the like in reference to a protein-inhibitor interaction means negatively affecting (e.g. decreasing) the activity or function of the protein relative to the activity or function of the protein in the absence of the inhibitor. In embodiments inhibition means negatively affecting (e.g. decreasing) the concentration or levels of the protein relative to the concentration or level of the protein in the absence of the inhibitor. In embodiments, inhibition refers to reduction of a disease or symptoms of disease. In embodiments, inhibition refers to a reduction in the activity of a particular protein target. Thus, inhibition includes, at least in part, partially or totally blocking stimulation, decreasing, preventing, or delaying activation, or inactivating, desensitizing, or down-regulating signal transduction or enzymatic activity or the amount of a protein. In embodiments, inhibition refers to a reduction of activity of a target protein resulting from a direct interaction (e.g. an inhibitor binds to the target protein). In embodiments, inhibition refers to a reduction of activity of a target protein from an indirect interaction (e.g. an inhibitor binds to a protein that activates the target protein, thereby preventing target protein activation).

The terms "inhibitor," "repressor" or "antagonist" or "downregulator" interchangeably refer to a substance capable of detectably decreasing the expression or activity of a given gene or protein. The antagonist can decrease expression or activity 10%, 20%, 30%, 40%, 50%, 60%, 70%, 80%, 90% or more in comparison to a control in the absence of the antagonist. In certain instances, expression or activity is 1.5-fold, 2-fold, 3-fold, 4-fold, 5-fold, 10-fold or lower than the expression or activity in the absence of the antagonist.

The term "expression" includes any step involved in the production of the polypeptide including, but not limited to, transcription, post-transcriptional modification, translation, post-translational modification, and secretion. Expression can be detected using conventional techniques for detecting protein (e.g., ELISA, Western blotting, flow cytometry, immunofluorescence, immunohistochemistry, etc.).

The term "gene expression" refers to any step in the process by which information from a gene is used in the synthesis of a functional gene product. These products are often proteins, but in non-protein coding genes such as transfer RNA (tRNA) or small nuclear RNA (snRNA) genes, the product is a functional RNA.

The term "reference value" as used herein refers to a value to which a measured quantity is compared. In embodiments, a reference value is assigned to genes in order to compare measured gene expression levels and make a comparison of whether the measured value is greater, equal, or less than the reference value, which then enables a determination of increased, no change, or decreased expression level of the gene. In embodiments, a reference value is assigned to an activity level representing the collective reference expression levels of several genes (such as genes associated with a particular signature). In embodiments, reference values are pre-determined values, such as from previous measurements for which expression levels were previously measured. In embodiments, a reference value is a control value for a known sample or condition that was previously measured, or is measured in parallel with a test sample. In embodiments, a reference value is a value for a sample from a subject at an earlier time point, to which values a value for a test sample at a later time point may be compared, and which may be measured separately or simultaneously with the test sample. In embodiments, a known sample providing the reference value is a non-cancerous tissue of the same type from which a test cancer cell originated, or a cell line of the same type as a test cancer cell. In embodiments, the reference value represents a difference between two treatment conditions for the known sample (e.g., a measure in the change of an activity level or the expression of one or more genes between a first condition in which a particular signaling pathway was induced, and a second condition in which the particular signaling pathway was not induced). In embodiments, a pathway activity increase or decrease of one standard deviation from the mean is considered significant.

In embodiments, the reference value is a reference activity score. In embodiments, a reference activity score is the result of a weighted average of normalized expression levels for genes in a pathway signature that may be ranked, linearly combined, and optionally scaled to between zero (0) and one (1). In embodiments, a scaled activity score of more than about 0.05, 0.1, 0.2, 0.3, 0.4, 0.5, 0.6, 0.7, 0.8, 0.9, 0.95, or more of the maximum score indicates a significantly increased activity in the corresponding pathway. In embodiments, a significantly increased activity is indicated by a scaled activity score of more than about 0.5 of the maximum score. In embodiments, a scaled score of about zero (0), a minimum unscaled score in a set of multiple samples, or a minimum unsealed score from an independent set of reference samples represents the activity score for a population of control cells in which the signaling pathway is not induced.

The term "associated" or "associated with" in the context of a substance, substance activity, or function associated with a disease (e.g. a protein associated disease, such as a cancer (e.g., cancer, inflammatory disease, autoimmune disease, or infectious disease)) means that the disease (e.g. cancer, inflammatory disease, autoimmune disease, or infectious disease) is caused by (in whole or in part), or a symptom of the disease is caused by (in whole or in part) the substance or substance activity or function. As used herein, what is described as being associated with a disease, if a causative agent, could be a target for treatment of the disease.

The term "signaling pathway" or "pathway" as used herein refers to a series of interactions between cellular and optionally extra-cellular components (e.g. proteins, nucleic acids, small molecules, ions, lipids) that conveys a change in one component to one or more other components, which in turn may convey a change to additional components, which is optionally propagated to other signaling pathway components. In embodiments, a signaling pathway is identified by a particular gene (e.g., the IFN signaling pathway), which refers to the pathway identified by signaling changes induced by activity of the indicated gene or corresponding protein (e.g., IFN). In embodiments, the signaling pathway includes genes whose expression is statistically significantly increased and/or decreased in response to overexpression of a particular gene that identifies the pathway.

The term "activity level" as used herein refers to a value representing the level of gene expression of all or a subset of genes in a particular pathway. In embodiments, activity level is determined by measuring gene expression of genes in a particular pathway. In embodiments, an activity level is a value calculated based on the expression levels of a plurality of genes in a particular pathway. A variety of suitable algorithms are available for calculating an activity level based on gene expression data from a plurality of genes. In embodiments, gene expression levels are analyzed using the Adaptive Signature Selection and InteGratioN toolkit (ASSIGN; see, e.g., Shen et al., 2015 Jun. 1; 31(11): 1745-53; available from BioConductor) to calculate an activity level. In embodiments, gene expression levels are analyzed using Gene Set Variation Analysis (GSVA; see, e.g., Hänzelmann et al., *BMC Bioinformatics*. 2013; 14: 7) to calculate an activity level. In embodiments, gene expression levels are analyzed using gene set enrichment analysis (GSEA) or single sample GSEA (ssGSEA; see, e.g., Barbie et al., Nature. 2009 Nov. 5; 462(7269): 108-112) to calculate an activity level. In embodiments, expression levels for all genes of a particular signature are collectively expressed as a single activity level value (e.g., a score) for that signature. In embodiments, comparing gene expression values for genes of a signature to a reference is performed by comparing a score for that signature to a reference score or threshold.

Methods of Use

In an aspect, provided herein is a method including detecting one or more parameters in a sample of peripheral blood from a subject with cancer, including detecting (i) gene expression in monocytes including (1) increased expression of one or more of NFKB1, MYD88, NFKBIA or NFKBIZ, (2) decreased expression of IKBKB, (3) increased expression of one or more of growth factor genes, and/or (4) increased expression of one or more TNF genes, compared to a control; (ii) a greater number of CD8+ differentiated cells, a greater number of CD4+ naive cells, fewer CD4+ differentiated cells, and fewer T follicular helper ($T_{FH}$) cells compared to a control; or (iii) a lower density of total peripheral blood mononuclear cells, a lower density of CD4+ effector memory (EM) cells, and a higher density of classical monocytes compared to a control.

In an aspect, provided herein is a method of identifying a cancer of a subject as responsive to treatment with a PD-1 inhibitor. The method includes detecting one or more parameters in a sample of peripheral blood from the subject, including detecting (i) gene expression in monocytes including (1) increased expression of one or more of NFKB1, MYD88, NFKBIA or NFKBIZ, (2) decreased expression of IKBKB, (3) increased expression of one or more of growth factor genes, and/or (4) increased expression of one or more TNF genes, compared to a control; (ii) greater number of CD8+ differentiated cells, a greater number of CD4+ naive cells, fewer CD4+ differentiated cells, and fewer T follicular helper ($T_{FH}$) cells compared to a control; or (iii) a lower density of total peripheral blood mononuclear cells, a lower density of CD4+ effector memory (EM) cells, and a higher density of classical monocytes compared to a control.

In an aspect, provided herein is a method for treating cancer in a subject. The method includes detecting one or more parameters in a sample of peripheral blood from the subject, including detecting (i) gene expression in monocytes including (1) increased expression of one or more of NFKB1, MYD88, NFKBIA or NFKBIZ, (2) decreased expression of IKBKB, (3) increased expression of one or more of growth factor genes, and/or (4) increased expression of one or more TNF genes, compared to a control; (ii) a greater number of CD8+ differentiated cells, a greater number of CD4+ naive cells, fewer CD4+ differentiated cells, and fewer T follicular helper ($T_{FH}$) cells compared to a control; or (iii) a lower density of total peripheral blood mononuclear cells, a lower density of CD4+ effector memory (EM) cells, and a higher density of classical monocytes compared to a control; and identifying the cancer as responsive to treatment with a PD-1 inhibitor if the cancer has one or more of the parameters (i)-(iii).

In embodiments, the cancer is gastrointestinal cancer. In embodiments, the gastrointestinal cancer is selected from colorectal cancer, gastroesophogeal cancer, pancreatic cancer, and biliary cancer. In embodiments, the gastrointestinal cancer is colorectal cancer. In embodiments, the gastrointestinal cancer is gastroesophogeal cancer. In embodiments, the gastrointestinal cancer is pancreatic cancer. In embodiments, the gastrointestinal cancer is biliary cancer.

In embodiments, the methods described herein further include detecting one or more of the following parameters: (iv) increased expression in T cells of one or more cell death genes compared to a control; (v) greater number of CTLA4+CD4+ EM cells and PD-1+CD8+ cells compared to a control; (vi) greater number of classical, CD86+, and HLADR+ monocytes as measured by florescence-activated cell sorting (FACS) and compared to a control; and (vii) fewer CD4+EM cells and a greater number of CLT4+CD4+ EM cells as measured by FACS and compared to a control.

In embodiments, the methods described herein include detecting one or more parameters including (i) gene expression in monocytes including (1) increased expression of one or more of NFKB1, MYD88, NFKBIA or NFKBIZ, (2) decreased expression of IKBKB, (3) increased expression of one or more of growth factor genes, and/or (4) increased expression of one or more TNF genes, compared to a control; (ii) a greater number of CD8+ differentiated cells, a greater number of CD4+ naive cells, fewer CD4+ differentiated cells, and fewer T follicular helper ($T_{FH}$) cells compared to a control; (iii) a lower density of total peripheral blood mononuclear cells, a lower density of CD4+ effector memory (EM) cells, and a higher density of classical monocytes compared to a control; (iv) increased expression in T cells of one or more cell death genes compared to a control; (v) greater number of CTLA4+CD4+ EM cells and PD-1+CD8+ cells compared to a control; (vi) greater number of classical, CD86+, and HLADR+ monocytes as measured by florescence-activated cell sorting (FACS) and compared to a control; and (vii) fewer CD4+EM cells and a greater number of CLT4+CD4+ EM cells as measured by FACS and compared to a control. In embodiments, two, three, four, five, six, or seven of the parameters (i)-(vii) are detected. In embodiments, two of the parameters (i)-(vii) are detected. In embodiments, three of the parameters (i)-(vii) are detected. In embodiments, four of the parameters (i)-(vii) are detected. In embodiments, five of the parameters (i)-(vii) are detected. In embodiments, six of the parameters (i)-(vii) are detected. In embodiments, all of the parameters (i)-(vii) are detected. In embodiments, all of the parameters (i)-(iii) are detected.

In embodiments, the methods described herein further include selecting a PD-1 inhibitor for administration to the subject, and optionally treating the subject with the PD-1 inhibitor, if one or more of the following parameters is detected: one or more parameters including (i) gene expression in monocytes including (1) increased expression of one or more of NFKB1, MYD88, NFKBIA or NFKBIZ, (2) decreased expression of IKBKB, (3) increased expression of one or more of growth factor genes, and/or (4) increased expression of one or more TNF genes, compared to a control; (ii) a greater number of CD8+ differentiated cells, a greater number of CD4+ naive cells, fewer CD4+ differentiated cells, and fewer T follicular helper ($T_{FH}$) cells compared to a control; (iii) a lower density of total peripheral blood mononuclear cells, a lower density of CD4+ effector memory (EM) cells, and a higher density of classical monocytes compared to a control; (iv) increased expression in T cells of one or more cell death genes compared to a control; (v) greater number of CTLA4+CD4+ EM cells and PD-1+CD8+ cells compared to a control; (vi) greater number of classical, CD86+, and HLADR+ monocytes as measured by florescence-activated cell sorting (FACS) and compared to a control; and (vii) fewer CD4+EM cells and a greater number of CLT4+CD4+ EM cells as measured by FACS and compared to a control. In embodiments, two, three, four, five, six, or seven of the parameters (i)-(vii) are detected. In embodiments, two of the parameters (i)-(vii) are detected. In embodiments, three of the parameters (i)-(vii) are detected. In embodiments, four of the parameters (i)-(vii) are detected. In embodiments, five of the parameters (i)-(vii) are detected. In embodiments, six of the parameters (i)-(vii) are detected. In embodiments, seven of the parameters (i)-(vii) are detected. In embodiments, all of the parameters (i)-(vii) are detected.

In embodiments, the methods described herein include detecting in monocytes increased expression of one or more of NFKB1, MYD88, NFKBIA or NFKBIZ compared to a control. In embodiments, the methods described herein include detecting in monocytes increased expression of NFKB1 compared to a control. In embodiments, the methods described herein include detecting in monocytes increased expression of MYD88 compared to a control. In embodiments, the methods described herein include detecting in monocytes increased expression of NFKBIA compared to a control. In embodiments, the methods described herein include detecting in monocytes increased expression of NFKBIZ compared to a control. In embodiments, increased expression of two or more of NFKB1, MYD88, NFKBIA or NFKBIZ are detected. In embodiments, increased expression of NFKB1, MYD88, NFKBIA and NFKBIZ are detected.

In embodiments, the methods described herein include detecting in monocytes increased expression of one or more growth factor genes including one or more of FOS, JUN, or JUNB compared to a control. In embodiments, the methods described herein include detecting in monocytes increased expression of FOS compared to a control. In embodiments, the methods described herein include detecting in monocytes increased expression of JUN compared to a control. In embodiments, the methods described herein include detecting in monocytes increased expression of JUNB compared to a control. In embodiments, increased expression of FOS, JUN, and JUNB is detected.

In embodiments, the methods described herein include detecting in monocytes increased expression of one or more TNF genes include one or more of TNF, TNFAIP2, or TNFAIP3 compared to a control. In embodiments, the methods described herein include detecting in monocytes increased expression of TNF compared to a control. In embodiments, the methods described herein include detecting in monocytes increased expression of TNFAIP2 compared to a control. In embodiments, the methods described herein include detecting in monocytes increased expression of TNFAIP3 compared to a control. In embodiments, increased expression of TNF, TNFAIP2, and TNFAIP3 is detected.

In embodiments, the methods described herein include detecting in a sample of peripheral blood a greater number of CD8+ differentiated cells, a greater number of CD4+ naive cells, fewer CD4+ differentiated cells, and fewer T follicular helper ($T_{FH}$) cells compared to a control.

In embodiments, the methods described herein include detecting in a sample of peripheral blood a lower density of total peripheral blood mononuclear cells, a lower density of CD4+ effector memory (EM) cells, and a higher density of classical monocytes compared to a control.

In embodiments, the methods described herein include detecting increased expression in T cells of one or more cell death genes compared to a control, the cell death genes including one or more of CASP1, CASP3, CASP7, or CASP8. In embodiments, the methods described herein include detecting increased expression in T cells of CASP1 compared to a control. In embodiments, the methods described herein include detecting increased expression in T cells of CASP3 compared to a control. In embodiments, the methods described herein include detecting increased expression in T cells of CASP7 compared to a control. In embodiments, the methods described herein include detecting increased expression in T cells of CASP8 compared to a control. In embodiments, increased expression of CASP1, CASP3, CASP7, and CASP8 is detected.

In embodiments, the methods described herein include detecting a greater number of CTLA4+CD4+ EM cells and PD-1+CD8+ cells compared to a control.

In embodiments, the methods described herein include detecting a greater number of classical, CD86+, and HLADR+ monocytes as measured by florescence-activated cell sorting (FACS) and compared to a control.

In embodiments, the methods described herein include detecting fewer CD4+EM cells and a greater number of CLT4+CD4+ EM cells as measured by FACS and compared to a control.

In embodiments, detecting gene expression includes one or more of single-cell RNA sequencing, single sample gene set enrichment analysis, Northern blotting, fluorescent in situ hybridization, reverse transcription polymerase chain reaction (RT-PCR), serial analysis of gene expression (SAGE), microarray, or tiling arrays. In embodiments, detecting gene expression includes single-cell RNA sequencing. In embodiments, detecting gene expression includes single sample gene set enrichment analysis. In embodiments, detecting gene expression includes Northern blotting. In embodiments, detecting gene expression includes fluorescent in situ hybridization. In embodiments, detecting gene expression includes reverse transcription polymerase chain reaction (RT-PCR). In embodiments, detecting gene expression includes serial analysis of gene expression (SAGE) microarray. In embodiments, detecting gene expression includes tiling arrays.

In embodiments, detecting a number of cells as fewer or greater than a control includes one or more of single-cell RNA sequencing, affinity-based pseudotime reconstruction, flow cytometry or immunophenotyping. In embodiments, detecting a number of cells as fewer or greater than a control includes single-cell RNA sequencing. In embodiments, detecting a number of cells as fewer or greater than a control includes affinity-based pseudotime reconstruction. In embodiments, detecting a number of cells as fewer or greater than a control includes flow cytometry. In embodiments, detecting a number of cells as fewer or greater than a control includes immunophenotyping.

In embodiments, the methods described herein further include selecting a subject for anticancer therapy (other than a PD-1 inhibitor) if the cancer is not identified as responsive to treatment with a PD-1 inhibitor; and optionally administering the anticancer therapy to the subject.

In embodiments, the methods described herein include selection and/or administration of anticancer therapy where the anticancer therapy includes one or more of radiation therapy, chemotherapy, surgery, or immunotherapy. In embodiments, the anticancer therapy includes radiation therapy. In embodiments, the anticancer therapy includes chemotherapy. In embodiments, the anticancer therapy includes surgery. In embodiments, the anticancer therapy includes immunotherapy.

In embodiments, the methods described herein include selection and/or administration of a PD-1 inhibitor. In embodiments, the PD-1 inhibitor is a PD-1 antibody. In embodiments, the PD-1 antibody is one or more of pembrolizumab, nivolumab, or cemiplimab. In embodiments, the PD-1 antibody is pembrolizumab. In embodiments, the PD-1 antibody is nivolumab. In embodiments, the PD-1 antibody is cemiplimab.

In embodiments, the methods described herein further include treating the subject with an anticancer therapy other than a PD-1 inhibitor. In embodiments, anticancer therapy other than a PD-1 inhibitor includes radiation therapy, chemotherapy, surgery, or immunotherapy excluding PD-1 inhibitor. In embodiments, anticancer therapy other than a PD-1 inhibitor is radiation therapy. In embodiments, anticancer therapy other than a PD-1 inhibitor is chemotherapy. In embodiments, anticancer therapy other than a PD-1 inhibitor is surgery. In embodiments, anticancer therapy other than a PD-1 inhibitor is immunotherapy excluding PD-1 inhibitor. Immunotherapy excluding PD-1 inhibitor includes PD-L1 inhibitors such as atezolizumab, CTLA-4 inhibitors such as ipilmumab, adoptive cell transfer, targeted therapy including small-molecule drugs or monoclonal antibodies, cytokines including interferons and interleukins, and *Bacillus calmette-guerin* (BCG).

In an aspect, provided herein is a method including detecting one or more parameters in a sample of peripheral blood from a subject with cancer previously treated with a PD-1 inhibitor, including detecting (i) in T cells, (1) increased expression of one or more interferon type I or type II signaling genes, (2) increased expression one or more of NFKB1, MYD88, NFKBIA or NFKBIZ, (3) increased expression of one or more major histocompatibility complex (MHC) class I or class II processing genes, (4) increased expression of one or more of CCL3, CCL4, CCL5, and CCR5, (5) decreased expression of one or more of CXCR3 or CCR2 genes, (6) increased expression in CD8+ T cells of one or more cell death genes, (7) a greater number of differentiated CD8+ cells, and/or (8) fewer differentiated CD4+ cells compared to a control; (ii) or in monocytes, (1) increased expression of genes upregulated by IFN stimulation, and/or (2) increased expression of genes upregulated by major histocompatibility complex 2 (MHCII) production.

In an aspect, provided herein is a method of identifying a cancer of a subject previously treated with a PD-1 inhibitor as responsive to treatment with the PD-1 inhibitor, the method including detecting one or more parameters in a sample of peripheral blood from the subject, including detecting (i) in T cells, (1) increased expression of one or more interferon type I or type II signaling genes, (2) increased expression one or more of NFKB1, MYD88, NFKBIA or NFKBIZ, (3) increased expression of one or more major histocompatibility complex (MHC) class I or class II processing genes, (4) increased expression of one or more of CCL3, CCL4, CCL5, and CCR5, (5) decreased expression of one or more of CXCR3 or CCR2 genes, (6) increased expression in CD8+ T cells of one or more cell death genes, (7) a greater number of differentiated CD8+ cells, and/or (8) fewer differentiated CD4+ cells compared to a control; or (ii) in monocytes, (1) increased expression of genes upregulated by IFN stimulation, and/or (2) increased expression of genes upregulated by major histocompatibility complex 2 (MHCII) production.

In an aspect, provided herein is a method of monitoring response to PD-1 immunotherapy in a subject previously treated with a PD-1 inhibitor, the method including detecting (i) in T cells, (1) increased expression of one or more interferon (IFN) type I or type II signaling genes, (2) increased expression one or more of NFKB1, MYD88, NFKBIA or NFKBIZ, (3) increased expression of one or more major histocompatibility complex (MHC) class I or class II processing genes, (4) increased expression of one or more of CCL3, CCL4, CCL5, and CCR5, (5) decreased expression of one or more of CXCR3 or CCR2 genes, (6) increased expression in CD8+ T cells of one or more cell death genes, (7) a greater number of differentiated CD8+ cells, and/or (8) fewer differentiated CD4+ cells compared to a control; or (ii) in monocytes, (1) increased expression of genes upregulated by IFN stimulation, and/or (2) increased expression of genes upregulated by major histocompatibility complex 2 (MHCII) production; and identifying the cancer as responsive to continued treatment with the PD-1 inhibitor if one or both of parameters (i) and (ii) are detected.

In embodiments, the cancer is gastrointestinal cancer. In embodiments, the gastrointestinal cancer is selected from colorectal cancer, gastroesophogeal cancer, pancreatic cancer, and biliary cancer. In embodiments, the gastrointestinal cancer is colorectal cancer. In embodiments, the gastrointestinal cancer is gastroesophogeal cancer. In embodiments, the gastrointestinal cancer is pancreatic cancer. In embodiments, the gastrointestinal cancer is biliary cancer.

In embodiments, the methods described herein include detecting in a sample of peripheral blood from a subject with cancer previously treated with a PD-1 inhibitor, in T cells increased expression in one or more interferon (IFN) type I or type II signaling genes compared to a control. In embodiments, the methods described herein include detecting IFN signaling genes including one or more genes of FIGS. 17A-C. In embodiments, the IFN signaling genes include one or more of IFIT1/3, IFITM3, IFI44L, PSME2, IFI6, ISG15. In embodiments, the IFN signaling genes include two or more of IFIT1/3, IFITM3, IFI44L, PSME2, IFI6, ISG15. In embodiments, the IFN signaling genes include IFIT1/3, IFITM3, IFI44L, PSME2, IFI6, and ISG15. In embodiments, the IFN signaling genes include one or more of IFNG, STAT1, STAT2, IRF1, IRF2, IRF7, SOCS1, SOCS2, SOCS3, IFIT1, IFIT2, IFIT3, IFIT5, IFITM1, IFITM2, IFITM3, ISG15, ISG20, GBP5, IFNGR1, IFNGR2, IFI16, IFI35, IFI44.

In embodiments, the methods described herein include detecting in a sample of peripheral blood from a subject with cancer previously treated with a PD-1 inhibitor, in T cells increased expression of one or more of NFKB1, MYD88, NFKBIA or NFKBIZ. In embodiments, the methods described herein include detecting in T cells increased expression of NFKB1 compared to a control. In embodiments, the methods described herein include detecting in T cells increased expression of MYD88 compared to a control. In embodiments, the methods described herein include detecting in T cells increased expression of NFKBIA compared to a control. In embodiments, the methods described herein include detecting in T cells increased expression of NFKBIZ compared to a control. In embodiments, increased expression of NFKB1, MYD88, NFKBIA and NFKBIZ is detected.

In embodiments, the methods described herein include detecting in a sample of peripheral blood from a subject with cancer previously treated with a PD-1 inhibitor, in T cells increased expression of one or more of MHC I processing genes including one or more of PIK3CD, PSMA7, PSMB8, PSMD9, HLA-A, HLA-B, or HLA-C compared to a control. In embodiments, the methods described herein include detecting in T cells increased expression of PIK3CD compared to a control. In embodiments, the methods described herein include detecting in T cells increased expression of PSMA7 compared to a control. In embodiments, the methods described herein include detecting in T cells increased expression of PSMB8 compared to a control. In embodiments, the methods described herein include detecting in T cells increased expression of PSMD9 compared to a control. In embodiments, the methods described herein include detecting in T cells increased expression of HLA-A compared to a control. In embodiments, the methods described herein include detecting in T cells increased expression of HLA-B compared to a control. In embodiments, the methods described herein include detecting in T cells increased expression of HLA-C compared to a control. In embodiments, increased expression in two or more of PIK3CD, PSMA7, PSMB8, PSMD9, HLA-A, HLA-B, or HLA-C is detected. In embodiments, increased expression of PIK3CD, PSMA7, PSMB8, PSMD9, HLA-A, HLA-B, and HLA-C is detected.

In embodiments, the methods described herein include detecting in a sample of peripheral blood from a subject with cancer previously treated with a PD-1 inhibitor, in T cells increased expression of MEW II processing genes including one or more of HLA-DQB1, HLA-DQA1, HLA-DPB1, HLA-DPA1, HLA-DRB1, HLA-DRA, HLA-DMB, or HLA-DMA compared to a control. In embodiments, the methods described herein include detecting in T cells increased expression of HLA-DQB1 compared to a control. In embodiments, the methods described herein include detecting in T cells increased expression of HLA-DQA1 compared to a control. In embodiments, the methods described herein include detecting in T cells increased expression of HLA-DPB1 compared to a control. In embodiments, the methods described herein include detecting in T cells increased expression of HLA-DPA compared to a control 1. In embodiments, the methods described herein include detecting in T cells increased expression of HLA-DRB1 compared to a control. In embodiments, the methods described herein include detecting in T cells increased expression of HLA-DRA compared to a control. In embodiments, the methods described herein include detecting in T cells increased expression of HLA-DMB compared to a control. In embodiments, the methods described herein include detecting in T cells increased expression of HLA-DMA compared to a control. In embodiments, increased expression of two or more of HLA-DQB1, HLA-DQA1, HLA-DPB1, HLA-DPA1, HLA-DRB1, HLA-DRA, HLA-DMB, or HLA-DMA is detected. In embodiments, increased expression of HLA-DQB1, HLA-DQA1, HLA-DPB1, HLA-DPA1, HLA-DRB1, HLA-DRA, HLA-DMB, and HLA-DMA is detected.

In embodiments, the methods described herein include detecting in a sample of peripheral blood from a subject with cancer previously treated with a PD-1 inhibitor, in T cells increased expression of one or more of CCL3, CCL4, CCL5, and CCR5 compared to a control. In embodiments, the methods described herein include detecting in T cells increased expression of CCL3 compared to a control. In embodiments, the methods described herein include detecting in T cells increased expression of CCL4 compared to a control. In embodiments, the methods described herein include detecting in T cells increased expression of CCL5 compared to a control. In embodiments, the methods described herein include detecting in T cells increased expression of CCR5 compared to a control. In embodiments, increased expression of CCL3, CCL4, CCL5, and CCR5 is detected.

In embodiments, the methods described herein include detecting in a sample of peripheral blood from a subject with cancer previously treated with a PD-1 inhibitor, in T cells decreased expression of one or more of CXCR3 and/or CCR2 genes compared to a control. In embodiments, the methods described herein include detecting in T cells decreased expression of CXCR3 genes compared to a control. In embodiments, the methods described herein include detecting in T cells decreased expression of CCR2 genes compared to a control.

In embodiments, the methods described herein include detecting in a sample of peripheral blood from a subject with cancer previously treated with a PD-1 inhibitor, increased expression in CD8+ T cells of one or more cell death genes compared to a control, the cell death genes including one or more of CASP1, CASP3, CASP7, or CASP8. In embodiments, the methods described herein include detecting increased expression in T cells of CASP1 compared to a control. In embodiments, the methods described herein include detecting increased expression in T cells of CASP3 compared to a control. In embodiments, the methods described herein include detecting increased expression in T cells of CASP7 compared to a control. In embodiments, the methods described herein include detecting increased expression in T cells of CASP8 compared to a control. In embodiments, increased expression of CASP1, CASP3, CASP7, and CASP8 is detected.

In embodiments, the methods described herein include detecting in a sample of peripheral blood from a subject with cancer previously treated with a PD-1 inhibitor a greater number of differentiated CD8+ cells compared to a control.

In embodiments, the methods described herein include detecting in a sample of peripheral blood from a subject with cancer previously treated with a PD-1 inhibitor, fewer differentiated CD4+ cells compared to a control.

In embodiments, the methods described herein include detecting in a sample of peripheral blood from a subject with cancer previously treated with a PD-1 inhibitor, in monocytes, increased expression of genes upregulated by IFN stimulation.

In embodiments, the methods described herein include detecting in a sample of peripheral blood from a subject with cancer previously treated with a PD-1 inhibitor, in monocytes, increased expression of genes upregulated by major histocompatibility complex 2 (WWII) production.

In embodiments, the methods described herein identifying a cancer as responsive to continued treatment with the PD-1 inhibitor if one or both of parameters (i) and (ii) are detected. In embodiments, the parameters are (i) in T cells, (1) increased expression of one or more interferon (IFN) type I or type II signaling genes, (2) increased expression one or more of NFKB1, MYD88, NFKBIA or NFKBIZ, (3) increased expression of one or more major histocompatibility complex (MHC) class I or class II processing genes, (4) increased expression of one or more of CCL3, CCL4, CCL5, and CCR5, (5) decreased expression of one or more of CXCR3 or CCR2 genes, (6) increased expression in CD8+ T cells of one or more cell death genes, (7) a greater number of differentiated CD8+ cells, and/or (8) fewer differentiated CD4+ cells compared to a control; and (ii) in monocytes, (1) increased expression of genes upregulated by IFN stimulation, and/or (2) increased expression of genes upregulated by major histocompatibility complex 2 (WWII) production.

In embodiments, detecting gene expression includes one or more of single-cell RNA sequencing, single sample gene set enrichment analysis, Northern blotting, fluorescent in situ hybridization, reverse transcription polymerase chain reaction (RT-PCR), serial analysis of gene expression (SAGE), microarray, or tiling arrays. In embodiments, detecting gene expression includes single-cell RNA sequencing. In embodiments, detecting gene expression includes single sample gene set enrichment analysis. In embodiments, detecting gene expression includes Northern blotting. In embodiments, detecting gene expression includes fluorescent in situ hybridization. In embodiments, detecting gene expression includes reverse transcription polymerase chain reaction (RT-PCR). In embodiments, detecting gene expression includes serial analysis of gene expression (SAGE) microarray. In embodiments, detecting gene expression includes tiling arrays.

In embodiments, detecting a number of cells as fewer or greater than a control includes one or more of single-cell RNA sequencing, affinity-based pseudotime reconstruction, flow cytometry or immunophenotyping. In embodiments, detecting a number of cells as fewer or greater than a control includes single-cell RNA sequencing. In embodiments, detecting a number of cells as fewer or greater than a control includes affinity-based pseudotime reconstruction. In embodiments, detecting a number of cells as fewer or greater than a control includes flow cytometry. In embodiments, detecting a number of cells as fewer or greater than a control includes immunophenotyping.

In embodiments, the methods described herein further include administering one or more doses of a PD-1 inhibitor after detecting (i) in T cells, (1) increased expression of one or more interferon type I or type II signaling genes, (2) increased expression one or more of NFKB1, MYD88, NFKBIA or NFKBIZ, (3) increased expression of one or more major histocompatibility complex (MHC) class I or class II processing genes, (4) increased expression of one or more of CCL3, CCL4, CCL5, and CCR5, (5) decreased expression of one or more of CXCR3 or CCR2 genes, (6) increased expression in CD8+ T cells of one or more cell death genes, (7) a greater number of differentiated CD8+ cells, and/or (8) fewer differentiated CD4+ cells compared to a control; or (ii) in monocytes, (1) increased expression of genes upregulated by IFN stimulation, and/or (2) increased expression of genes upregulated by major histocompatibility complex 2 (MHCII) production.

In embodiments, the methods described herein include selection and/or administration of a PD-1 inhibitor. In embodiments, the PD-1 inhibitor is a PD-1 antibody. In embodiments, the PD-1 antibody is one or more of pembrolizumab, nivolumab, or cemiplimab. In embodiments, the PD-1 antibody is pembrolizumab. In embodiments, the PD-1 antibody is nivolumab. In embodiments, the PD-1 antibody is cemiplimab.

In embodiments, the methods described herein further include selecting the subject for anticancer therapy (other than a PD-1 inhibitor) if the cancer is not identified as responsive to continued treatment with the PD-1 inhibitor, and optionally administering the anticancer therapy to the subject. In embodiments, the methods described herein further include selecting the subject for anticancer therapy if the cancer is not identified as responsive to continued treatment with the PD-1 inhibitor, and administering the anticancer therapy to the subject. In embodiments, the anticancer therapy includes one or more of radiation therapy, chemotherapy, surgery, or immunotherapy. In embodiments, the anticancer therapy includes radiation therapy. In embodiments, the anticancer therapy includes chemotherapy. In embodiments, the anticancer therapy includes surgery. In embodiments, the anticancer therapy includes immunotherapy.

In embodiments, the methods described herein further include treating the subject with an with an anticancer therapy other than a PD-1 inhibitor. In embodiments, anticancer therapy other than a PD-1 inhibitor includes radiation therapy, chemotherapy, surgery, or immunotherapy excluding PD-1 inhibitor. In embodiments, anticancer therapy other than a PD-1 inhibitor is radiation therapy. In embodiments, anticancer therapy other than a PD-1 inhibitor is chemotherapy. In embodiments, anticancer therapy other than a PD-1 inhibitor is surgery. In embodiments, anticancer therapy other than a PD-1 inhibitor is immunotherapy excluding PD-1 inhibitor. Immunotherapy excluding PD-1 inhibitor includes PD-L1 inhibitors such as atezolizumab, CTLA-4 inhibitors such as ipilmumab, adoptive cell transfer, targeted therapy including small-molecule drugs or monoclonal antibodies, cytokines including interferons and interleukins, and *Bacillus calmette-guerin* (BCG).

In an aspect, provided herein is a system including at least one processor; and at least one memory including program code which when executed by the at least one memory provides operations for performing a method as described herein.

In embodiments, the operations include collecting gene expression data associated with a subject, collecting cell density data associated with a subject; and providing, via a user interface, a prognosis for the subject based at least in part on detected gene expression and/or cell density In embodiments, the system includes functional modules, which are defined by computer executable instructions recorded on computer readable media and which cause a computer to perform method steps when executed. The modules are segregated by function for the sake of clarity. However, it should be understood that the modules/systems need not correspond to discreet blocks of code and the described functions can be carried out by the execution of various code portions stored on various media and executed at various times.

The computer readable storage media can be any available tangible media that can be accessed by a computer. Computer readable storage media includes volatile and nonvolatile, removable and non-removable tangible media implemented in any method or technology for storage of information such as computer readable instructions, data structures, program modules or other data. Computer readable storage media includes, but is not limited to, RAM (random access memory), ROM (read only memory), EPROM (erasable programmable read only memory), EEPROM (electrically erasable programmable read only memory), flash memory or other memory technology, CD-ROM (compact disc read only memory), DVDs (digital versatile disks) or other optical storage media, magnetic cassettes, magnetic tape, magnetic disk storage or other magnetic storage media, other types of volatile and nonvolatile memory, and any other tangible medium which can be used to store the desired information and which can accessed by a computer.

Computer-readable data embodied on one or more computer-readable media may define instructions, for example, as part of one or more programs that, as a result of being executed by a computer, instruct the computer to perform one or more of the functions described herein, and/or various embodiments, variations and combinations thereof. Such instructions may be written in any of a plurality of programming languages, for example, Java, J#, Visual Basic, C, C#, C++, Fortran, Pascal, Eiffel, Basic, COBOL assembly language, and the like, or any of a variety of combinations thereof. The computer-readable media on which such instructions are embodied may reside on one or more of the components of either of a system, or a computer readable storage medium described herein, may be distributed across one or more of such components.

The computer-readable media may be transportable such that the instructions stored thereon can be loaded onto any computer resource to implement the aspects discussed herein. In addition, it should be appreciated that the instructions stored on the computer-readable medium, described above, are not limited to instructions embodied as part of an application program running on a host computer. Rather, the instructions may be embodied as any type of computer code (e.g., software or microcode) that can be employed to program a computer to implement aspects of the present invention. The computer executable instructions may be written in a suitable computer language or combination of several languages.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Example 1

Signalling State and Cancer Response to Immunotherapy

In the experiments described herein, peripheral blood mononuclear cells (PBMCs) were collected from patients with advanced GI cancers throughout treatment with combination chemotherapy and immunotherapy. It was hypothesized that circulating immune cell frequency and signaling reflect intratumoral activity of immune cells, and that subsets of immune cells in patients responsive to immunotherapy are primed to recognize cancer cells but blocked through PD1 directed mechanisms. Immune cell abundance and phenotype evolution during treatment was measured by single cell RNA sequencing (scRNAseq) and flow cytometry. Data showed that patients who respond to immunotherapy can be recognized prior to treatment through increased abundance of naive T cells and monocytes primed for activation and an excess of exhausted T cells. After treatment, these responsive patients show a response both in cell numbers and cell activation as the inhibitory PD-1 pathways are blocked. These findings help identify patients for treatment and optimize the timing of treatment relative to chemotherapy.

Overview of Trial and Patient Cohort

Figure 1:
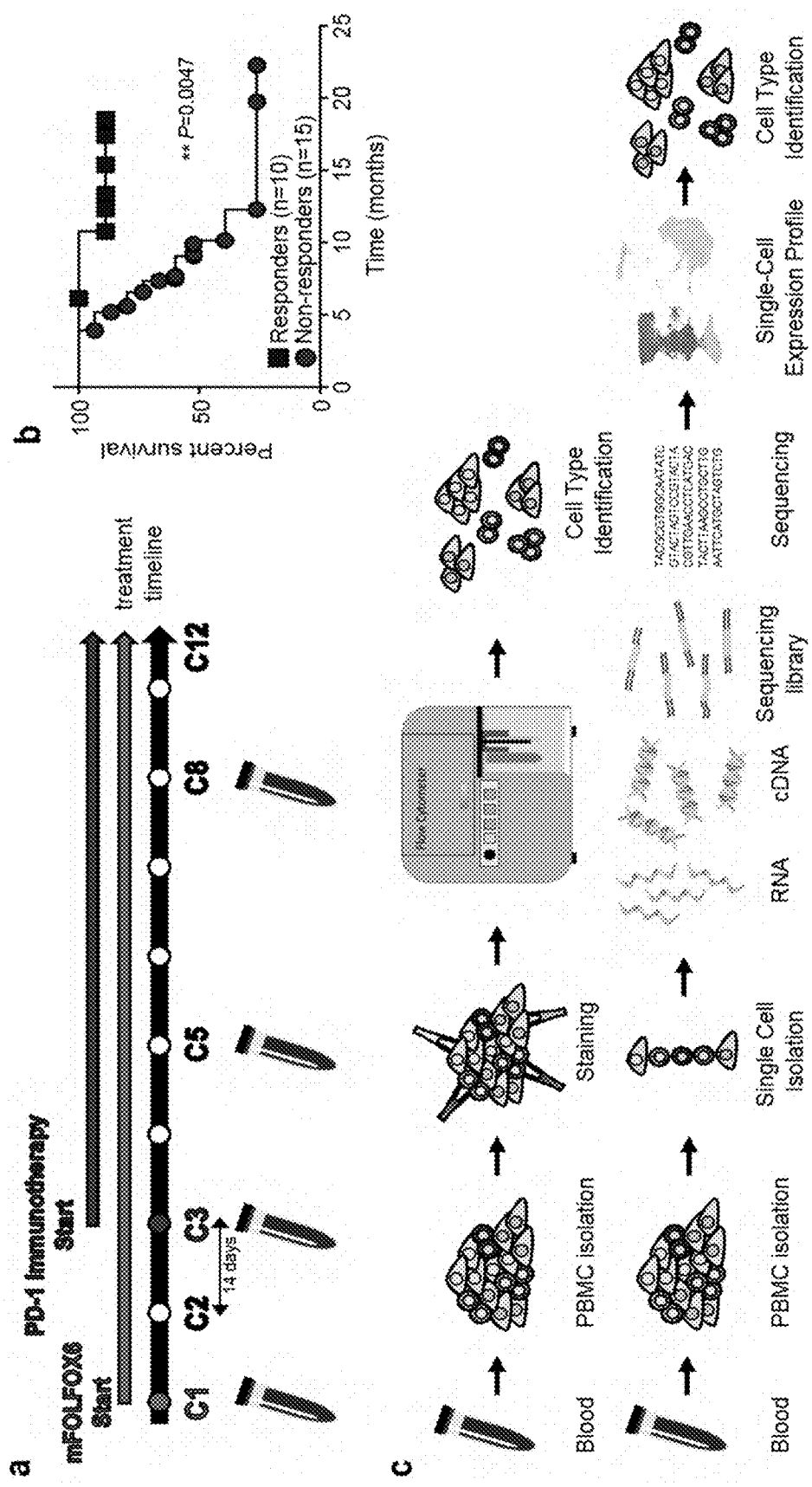
FIG. 1 illustrates an overview of a clinical trial treatment strategy, classification of patients, and pipeline used to investigate PBMCs. Panel (a) is a schematic of a treatment plan showing advanced gastrointestinal patients received FOLFOX6 chemotherapy at the beginning of the trial for two 14-day cycles. From cycles 3 through 12, they received both FOLFOX6 and anti-PD-1 immunotherapy. At baseline (cycle 1=C1), cycle 3 (C3), cycle 5 (C5), cycle 8 (C8) whole blood was collected and PBMCs were isolated and frozen. Panel (b) is a graph showing overall survival of responders and non-responders is plotted as percent survival vs. time in months. Panel (c) is a pictorial of an experimental set up showing PBMC analyses are performed using both flow cytometry and single-cell RNA sequencing.

Patients with advanced GI cancers, including colorectal, gastroesophageal, pancreatic, and biliary, were enrolled in a single institution phase I trial (NCT02268825) of modified FOLFOX6 (mFOLOFX6) chemotherapy regimen followed by a combination of chemotherapy and anti-PD-1 immunotherapy (pembrolizumab) (FIG. 1 panel (a)). Patient response was assessed according to the RECIST1.1 guideline that defined patients as complete responders (CR), partial responders (PR), stable disease (SD) and progressive disease (PD). All patients with a CR, PR, or SD were grouped as responder patients and the remaining as non-responders. Confirming the classification, 89% of responders survived more than 18 months compared to only 26% of non-responders (FIG. 1 panel (b)). PBMCs isolated from 3 to 4 time points were analyzed: cycle 1 (C1) provides the baseline without any treatment, cycle 3 (C3) treatment with only mFOLFOX6 chemotherapy, and cycle 5 (C5) or cycle 8 (C8) during treatment with both mFOLFOX6 and PD-li. A total of 12 patients (responder n=7, non-responder n=5) were analyzed by flow cytometry and 13 patients (responder n=7, non-responder n=6) by scRNAseq (FIG. 1 panel (c), FIGS. 9A-F and Table 1-2). Eight patients' samples were analyzed using both techniques (responder n=6, non-responder n=2).

As summarized in Table 1, there were a total of 18 patients, with 8 non-responders and 10 responders to the PD-1 immunotherapy treatment. Patient samples were cryopreserved peripheral blood mononuclear cells (PBMC) samples. The patients were treated for advanced (stage 3/4) gastrointestinal cancers (including colorectal, gastroesophageal, pancreatic and biliary cancers). Patients in this clinical trial (NCT02268825), were treated with modified FOLFOX6 (mFOLOFX6) chemotherapy regimen consisting of 400 mg/m$^2$ intravenous (IV) leucovorin, 400 mg/m$^2$ IV fluorouracil (5-FU) bolus followed by 2400 mg/m$^2$ IV over 46 hrs and 85 mg/m$^2$ IV oxaliplatin (Eloxatin) every 2 weeks (i.e. 1 cycle) until disease progression, death, or completion of the study. Pembrolizumab 200 mg IV every two weeks was added to mFOLFOX6 at cycle 3, after 4 weeks of mFOLFOX. Every two weeks, and before starting treatment, patients' blood was collected and PBMCs were isolated and cryopreserved. Median of previous history of chemotherapy treatment for responders was 101 days and 42 days for non-responders. Clinical trial participants are further identified by gender, race, ECOG performance status, primary cancer type, Pembrolizub dose level, prior systemic treatment, prior 5-FU and Oxaliplatin treatment, number of previous systemic treatment lines for metastatic disease, microsatellite instability (MSI), and whether or not there was correlated testing (FACS, scRNAseq, or FACS and scRNAseq).

Provided in Table 2 are the IQR (interquartile range) and laboratory reference range reported for white blood cells, red blood cells, hemoglobin, platelets, number of granulocytes, number of monocytes, and number of lymphocytes were recorded and grouped by total patients, non-responders, and responders.

TABLE 1

The patient and disease characteristics of the patients participating in the clinical trial.

|  | All Patients (n = 18) | Responders (n = 8) | Non-responders (n = 10) |
|---|---|---|---|
| Age, median years (IQR) | 62 (54-72) | 67 (60-73) | 60 (48-66) |
| Gender, n (%) |  |  |  |
| F | 8 (44) | 2 (25) | 6 (60) |
| M | 10 (56) | 6 (75) | 4 (40) |
| Race, n (%) |  |  |  |
| White | 14 (78) | 8 (100) | 6 (60) |
| Black or African American | 2 (11) | 0 (0) | 2 (20) |
| Unknown | 2 (11) | 0 (0) | 2 (20) |
| ECOG Performance Status, n (%) |  |  |  |
| 0 Fully active | 10 (56) | 4 (50) | 6 (60) |
| 1 Restricted | 8 (44) | 4 (50) | 4 (40) |
| Primary Cancer Type, n (%) |  |  |  |
| Colorectal Carcinoma | 9 (50) | 3 (38) | 6 (60) |
| Biliary Tract Cancer | 4 (22) | 1 (13) | 3 (30) |
| Gastroesophageal Carcinoma | 3 (17) | 3 (38) | 0 (0) |
| Pancreatic Carcinoma | 2 (11) | 1 (13) | 1 (10) |
| Pembrolizumab Dose level, n (%) |  |  |  |
| 75 mg q 2 weeks | 1 (6) | 0 (0) | 1 (10) |
| 200 mg q 2 weeks | 17 (94) | 8 (100) | 9 (90) |
| Prior Systemic Treatment, n (%) |  |  |  |
| No | 6 (33) | 6 (75) | 0 (0) |
| Yes | 12 (67) | 2 (25) | 10 (100) |
| Days from last dose of treatment, Median (IQR) | 42 (23-293) | 101 (34-167) | 42 (21-416) |
| Prior 5-FU and Oxaliplatin, n (%) |  |  |  |
| No | 10 (56) | 7 (88) | 3 (30) |
| Yes | 8 (44) | 1 (13) | 7 (70) |
| Days from last dose of 5-FU/Ox, Median (IQR) | 606 (298-986) | 927 (927-927) | 555 (249-1005) |
| Number of previous systemic treatment lines for metastatic disease, n (%) |  |  |  |
| 0 | 7 (39) | 6 (75) | 1 (10) |
| 1 | 4 (22) | 2 (25) | 2 (20) |
| 2 | 3 (17) | 0 (0) | 3 (30) |
| 3 | 4 (22) | 0 (0) | 4 (40) |

TABLE 1-continued

The patient and disease characteristics of the patients participating in the clinical trial.

|  | All Patients (n = 18) | Responders (n = 8) | Non-responders (n = 10) |
|---|---|---|---|
| Microsatellite Instability (MSI) Result, n (%) | | | |
| dMMR (MSI-high) | 4 (22) | 3 (38) | 1 (10) |
| MMR proficient (MSI-stable) | 8 (44) | 1 (13) | 7 (70) |
| Unknown | 6 (33) | 4 (50) | 2 (20) |
| Correlative testing, n (%) | | | |
| FACS | 5 (28) | 1 (13) | 4 (40) |
| Single cell (SC) | 5 (28) | 1 (13) | 4 (40) |
| FACS and SC | 8 (44) | 6 (75) | 2 (20) |

TABLE 2

The total blood count parameters for all clinical trial patients on day 1 of cycles 1, 3, and 5.

| | Blood Count with Differential, laboratory reference range | | | | | |
|---|---|---|---|---|---|---|
| | All Patients (n = 18) | | Responders (n = 8) | | Non-responders (n = 10) | |
| | Median (IQR) | Range | Median (IQR) | Range | Median (IQR) | Range |
| White Blood Cells, 3.20-10.60k/μL | | | | | | |
| C1 | 7.0 (4.6) | 3.9-17.2 | 7.3 (5.4) | 4.46-11.4 | 6.4 (4.6) | 3.9-17.2 |
| C3 | 4.2 (2.3) | 2.5-19.0 | 4.5 (1.4) | 3.13-6.7 | 3.6 (3.1) | 2.5-19.0 |
| C5 | 4.5 (1.9) | 2.4-11.9 | 4.7 (1.7) | 3.24-10.5 | 4.1 (4.0) | 2.4-11.9 |
| Red Blood Cells, 3.88-5.46M/μL | | | | | | |
| C1 | 4.3 (0.8) | 3.5-5.4 | 4.7 (0.6) | 3.75-5.4 | 4.1 (0.8) | 3.5-5.0 |
| C3 | 4.1 (0.9) | 2.8-5.4 | 4.4 (0.9) | 3.1-5.4 | 3.8 (1.0) | 2.8-4.8 |
| C5 | 3.7 (1.2) | 2.8-5.3 | 4.4 (0.9) | 2.84-5.3 | 3.5 (0.8) | 3.3-4.6 |
| Hemoglobin, 12.1-15.9 g/dL | | | | | | |
| C1 | 12.7 (2.6) | 9.4-16.1 | 12.8 (2.5) | 9.4-15.2 | 12.5 (3.4) | 9.6-16.1 |
| C3 | 11.9 (2.9) | 8.7-15.2 | 11.7 (3.3) | 9.5-14.7 | 12.2 (3.3) | 8.7-15.2 |
| C5 | 11.7 (2.6) | 8.8-15.9 | 12.3 (2.4) | 8.9-14.7 | 11.1 (3.5) | 8.8-15.9 |
| Platelets, 177-406k/μL | | | | | | |
| C1 | 212 (93) | 129-353 | 195 (104.3) | 148-339 | 234 (103) | 129-353 |
| C3 | 154 (50) | 93-228 | 134 (76.0) | 93-223 | 164 (38) | 112-228 |
| C5 | 147 (78) | 77-404 | 114 (118.8) | 77-404 | 166 (59) | 120-226 |
| Granulocyte #, 1.3-7.0k/μL | | | | | | |
| C1 | 4.6 (3.6) | 2.6-15.5 | 5.4 (4.5) | 3-8.6 | 4.1 (2.9) | 2.6-15.5 |
| C3 | 2.5 (2.1) | 1.1-16.7 | 2.5 (1.1) | 2-4.8 | 2.1 (2.5) | 1.1-16.7 |
| C5 | 3.0 (2.5) | 1.1-9.6 | 2.7 (1.4) | 1.37-8.5 | 3.3 (3.5) | 1.1-9.6 |
| Monocyte #, 0.2-0.7k/μL | | | | | | |
| C1 | 0.5 (0.3) | 0.2-1.1 | 0.5 (0.5) | 0.3-1.1 | 0.4 (0.4) | 0.2-0.9 |
| C3 | 0.4 (0.3) | 0.2-0.9 | 0.4 (0.5) | 0.3-0.9 | 0.4 (0.3) | 0.2-0.7 |
| C5 | 0.5 (0.4) | 0.0-1.1 | 0.5 (0.6) | 0-1.1 | 0.5 (0.3) | 0.3-0.7 |
| Lymphocyte #, 0.8-3.1k/μL | | | | | | |
| C1 | 1.4 (0.9) | 0.4-2.8 | 1.1 (0.7) | 0.4-1.7 | 1.7 (1.5) | 0.7-2.8 |
| C3 | 1.3 (0.7) | 0.5-2.3 | 1.1 (0.4) | 0.5-1.6 | 1.7 (0.6) | 0.7-2.3 |
| C5 | 1.3 (0.8) | 0.4-3.0 | 1.2 (0.4) | 0.44-2.2 | 1.6 (1.0) | 0.7-3.0 |

Identifying Immune Cell Populations from scRNA-Seq Profiles

Figure 2:
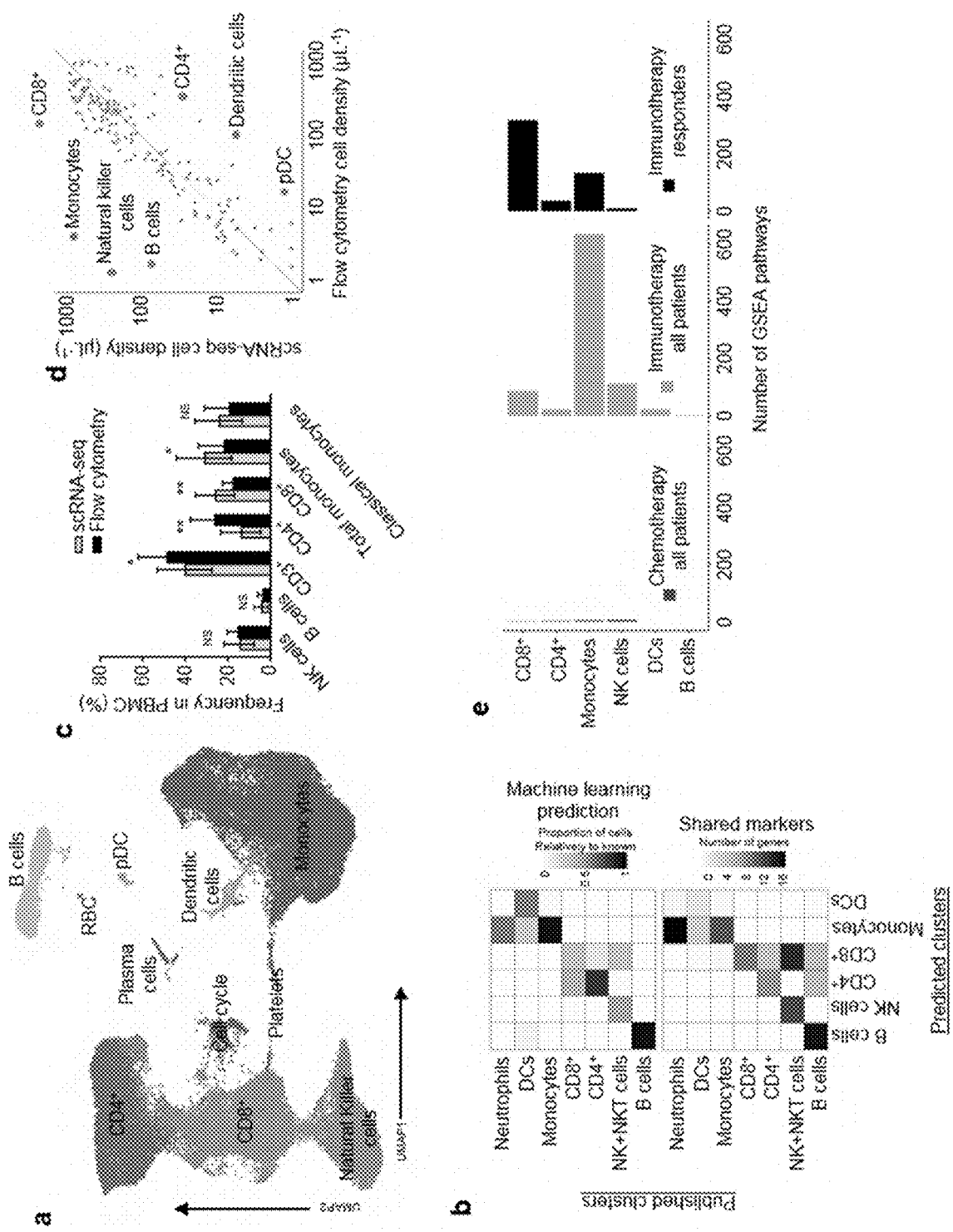
FIG. 2 shows data describing the dynamic nature of monocyte and T cell signaling following immunotherapy, but not chemotherapy, treatment in patients. Panel (a) is a Uniform Manifold Approximation and Projection (UMAP) of the scRNA seq data of all patients and all time points analyzed. The major PBMC, RBC (red blood cells), and pDC (plasmacytoid dendritic cells) clusters are labeled. Panel (b) is a chart showing the similarity of cluster annotation between predicted clusters and public datasets. The top portion corresponds to the machine learning prediction for the distribution of immune cells in public datasets, grouped by predicted clusters formed using the Random Forest learner, which was trained using the PD-1 scRNAseq samples (N=69745) data set. The bottom portion (labeled Shared marker genes) shows the number of shared genes between public dataset and the predicted clusters, including NKT (Natural killer T cells) and DC (Dendritic cells). Panel (c) is a graph showing direct comparison of the frequency of major populations of samples of 8 patients analyzed with scRNA-seq and flow cytometry. All time points and patients were pooled in order to compare the overall frequency of populations, the bars indicate s. d., NS (non-significant), and statistical significance is displayed as *$P<0.05$ and **$P<0.01$ (two-tailed unpaired t-test). Panel (d) is a plot of immune cell density estimates between scRNA-seq and flow cytometry. The densities of each cell type were obtained by both methods for each patient. The diagonal dashed line shows 1:1 correspondence between the approaches. Panel (e) is a graph showing the relative number of molecular pathways (identified using GSEA, or Gene Set Enrichment Analysis) impacted by chemotherapy (red bars; far left) and PD-1 immunotherapy (grey bars; middle). Also plotted are the number of pathways effected that are specific to PD-1 immunotherapy responders (black bars; right).
Figure 10:
FIG. 10 is a plot of UMAP key gene expression markers of major PBMC populations. The gene expression markers include MS4A1, KLRF1, GZMA, CD3D, CD4, CD8A, FCER1A, CD14, and CD16 (UMAP1 vs. UMAP2). Major PBMC types are verified by their characteristic expression of certain combinations of these genes. Unlike other dimension reduction techniques, UMAP representations preserve information about developmental similarity, with nearby cells being developmentally similar to one another.
Figure 11:
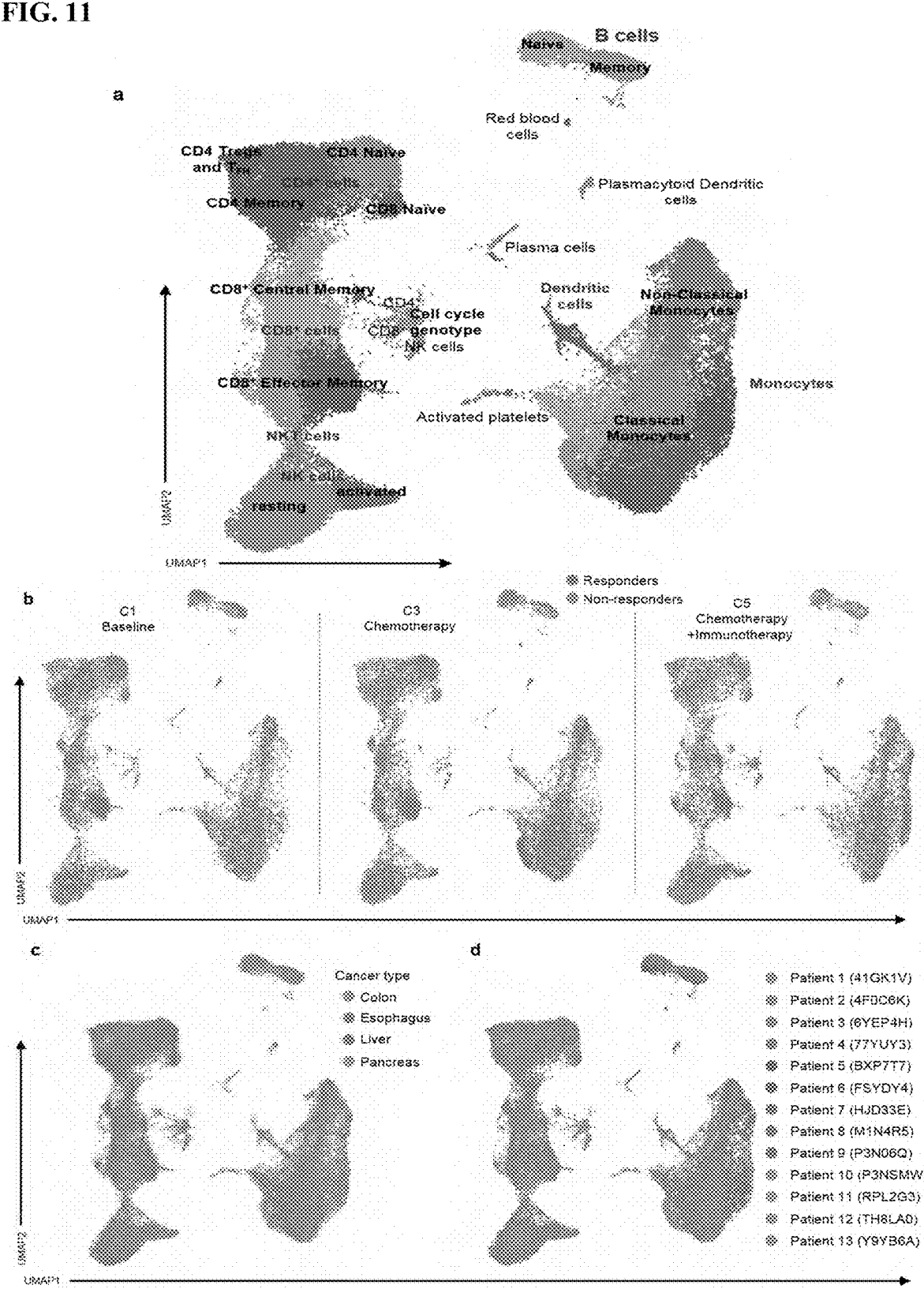
FIG. 11 illustrates that UMAP gene expression plots show no batch effects. Panel (a) is a Uniform Manifold Approximation and Projection (UMAP) of the scRNA seq data of all patients and all time points. Major PBMC clusters are labeled in red while subclusters or minor PBMC clusters are labeled in black. Panel (b) is the UMAP gene expression distribution per time point of treatment is plotted for each time point C1, C3, and C5, where C stands for cycle, 1 cycle is 14 days, C1 is the baseline time point, C3 is the chemotherapy FOLFOX regimen, C5 is the chemotherapy+anti PD-1 immunotherapy regimen. Panel (c) is the UMAP gene expression distribution per cancer analyzed. Panel (d) is the UMAP gene expression distribution per patient analyzed.

Single cell RNA sequencing was performed using the 10× platform, creating a transcriptional profile from 71,545 cells. Our analysis revealed a diverse set of 35 clusters. To identify cell type for each of these clusters, canonical gene expression was evaluated for each cluster to identify major PBMC lineages. (FIG. 2 panel (a), FIG. 10). Further interrogation of markers identified naïve, central memory and effector memory T cells, classical and non-classical monocytes, active and resting natural kill (NK) cells, naïve and memory B cells, dendritic cells and plasmacytoid dendritic cells (FIG. 11 panel (a), Table 3). No batch effects were found corresponding to time, patient or cancers (FIG. 11 panels (b)-(d)).

Provided in Table 3 are the major clusters and sub clusters annotation for single cell RNA sequencing analysis. Single cell RNA sequencing was performed using the 10× platform, creating a transcriptional profile from 71,545 cells, and the analysis revealed a diverse set of 35 clusters. To identify cell type for each of these clusters, canonical gene expression was evaluated for each cluster to identify major PBMC lineages. Further analysis of markers identified naïve, central memory and effector memory T cells, classical and non-classical monocytes, active and resting natural kill (NK) cells, naïve and memory B cells, dendritic cells and plasmacytoid dendritic cells.

TABLE 3

Major clusters and sub clusters annotation

| Cluster | Major clusters | Sub clusters |
|---|---|---|
| 1 | NK Cell | NK Cell Resting |
| 2 | Monocyte | Monocyte Classical |
| 3 | Monocyte | Monocyte Classical |
| 4 | Monocyte | Monocyte Non-Classical |
| 9 | Monocyte | Monocyte Classical Platelets |
| 10 | Monocyte | Monocyte Classical |
| 11 | B Cell | B Cell Naive |
| 12 | NK Cell | NK Cell Activated |
| 13 | B Cell | B Cell Memory |
| 14 | Dendritic Cell | Dendritic Cell |
| 15 | Monocyte | Monocyte Classical |
| 17 | Cell Cycle | Cell Cycle |
| 18 | Monocyte | Monocyte Classical |
| 19 | Plasmacytoid dendritic cell | Plasmacytoid Dendritic Cell |
| 20 | Plasma Cell | Plasma Cell |
| 22 | Activated Platelets | Activated Platelets |
| 23 | TCell | NA |
| 24 | RBC | RBC |
| 25 | Plasma Cell | Plasma Cell |
| T0 | T Cell CD4 | T Cell CD4 EM |
| T1 | T Cell CD4 | T Cell CD4 Naive |
| T10 | T Cell CD8 | T Cell CD8 Exhausted |
| T11 | T Cell CD8 | T Cell CD8 EM |
| T12 | T Cell CD8 | T Cell CD8 EM |
| T13 | T Cell CD8 | T Cell CD8 EM |
| T14 | T Cell CD8 | T Cell CD8 CM |
| T15 | T Cell CD4 | T Cell $T_{FH}$ |
| T2 | T Cell CD8 | T Cell CD8 TEMRA |
| T3 | T Cell CD8 | T Cell CD8 TEMRA |
| T4 | T Cell CD4 | T Cell CD4 EM |
| T5 | T Cell CD8 | T Cell CD8 EM |
| T6 | NA | NA |
| T7 | T Cell CD8 | T Cell CD8 CM |
| T8 | T Cell CD4 | T Cell Treg |
| T9 | T Cell CD8 | T Cell CD8 Naive |

Figure 12A:
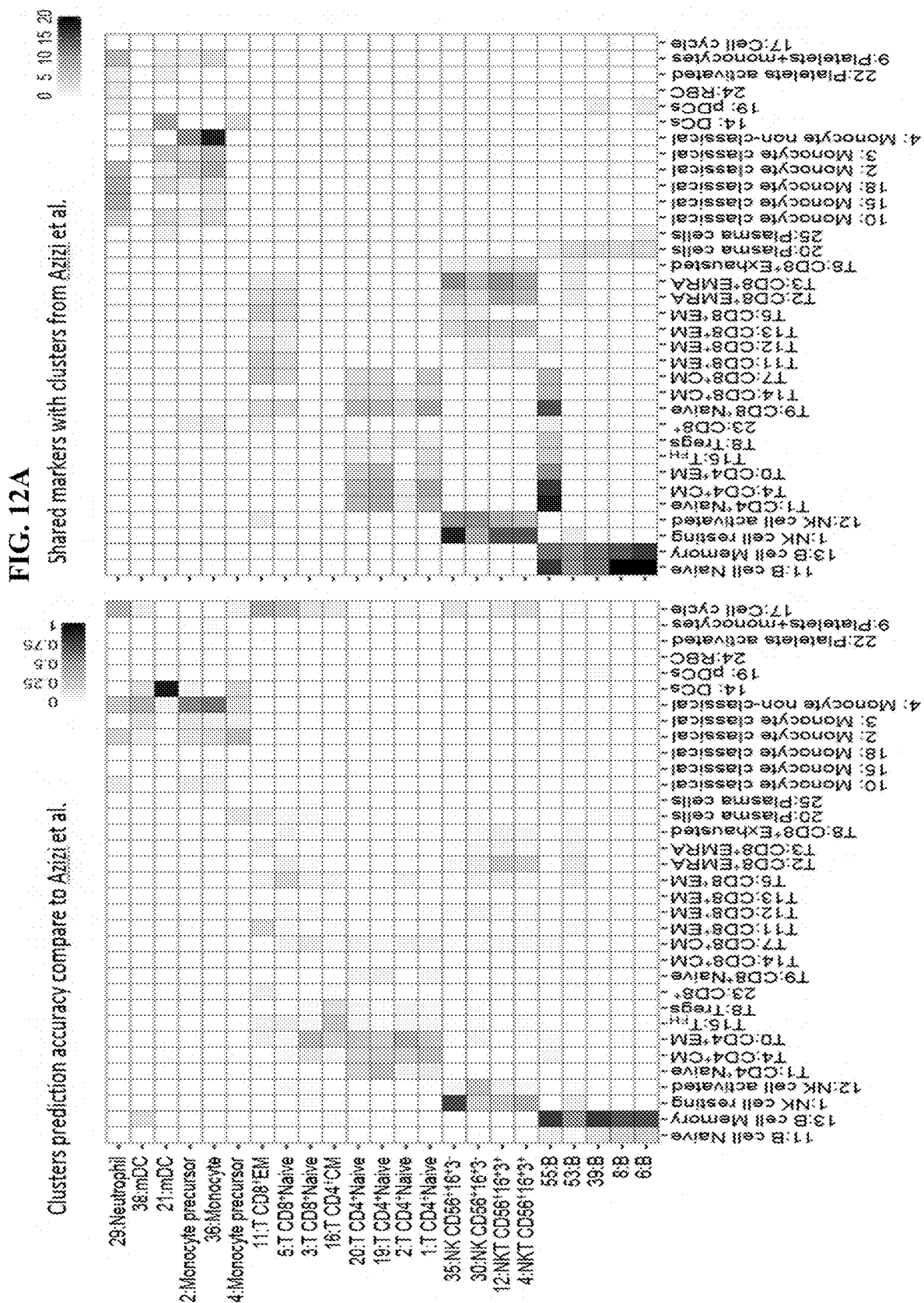
FIGS. 12A-B illustrate that UMAP labeled clusters are similar to public datasets. The left panels correspond to the machine learning prediction, where the distribution of immune cells in public datasets is predicted to PD-1 clusters by Random Forest learner using the patient sample cohort as a training set. The right panels are the shared marker genes, corresponding to the number of shared genes between public datasets and the patient sample cohort clusters.
Figure 12B:
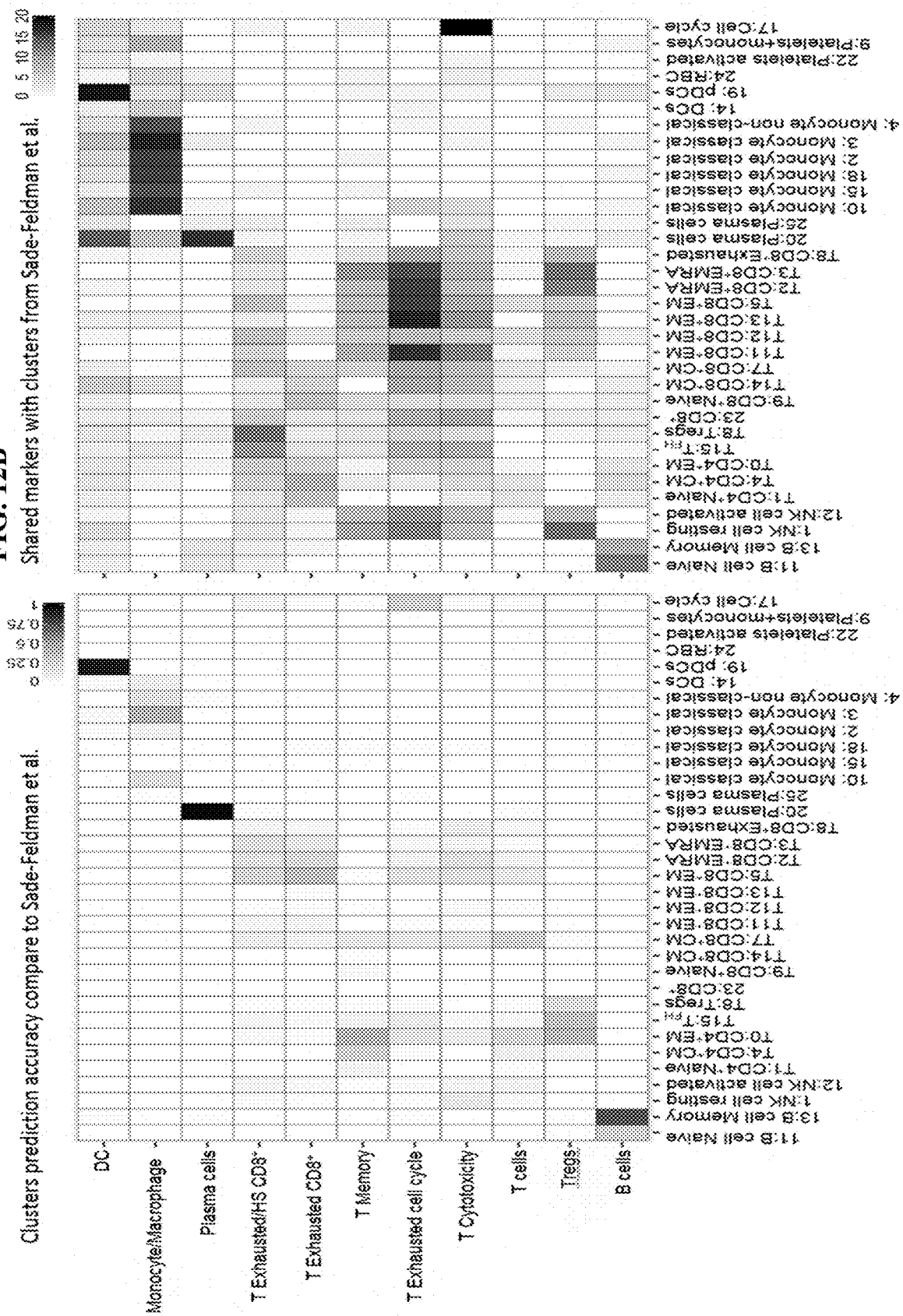
Figure 13A:
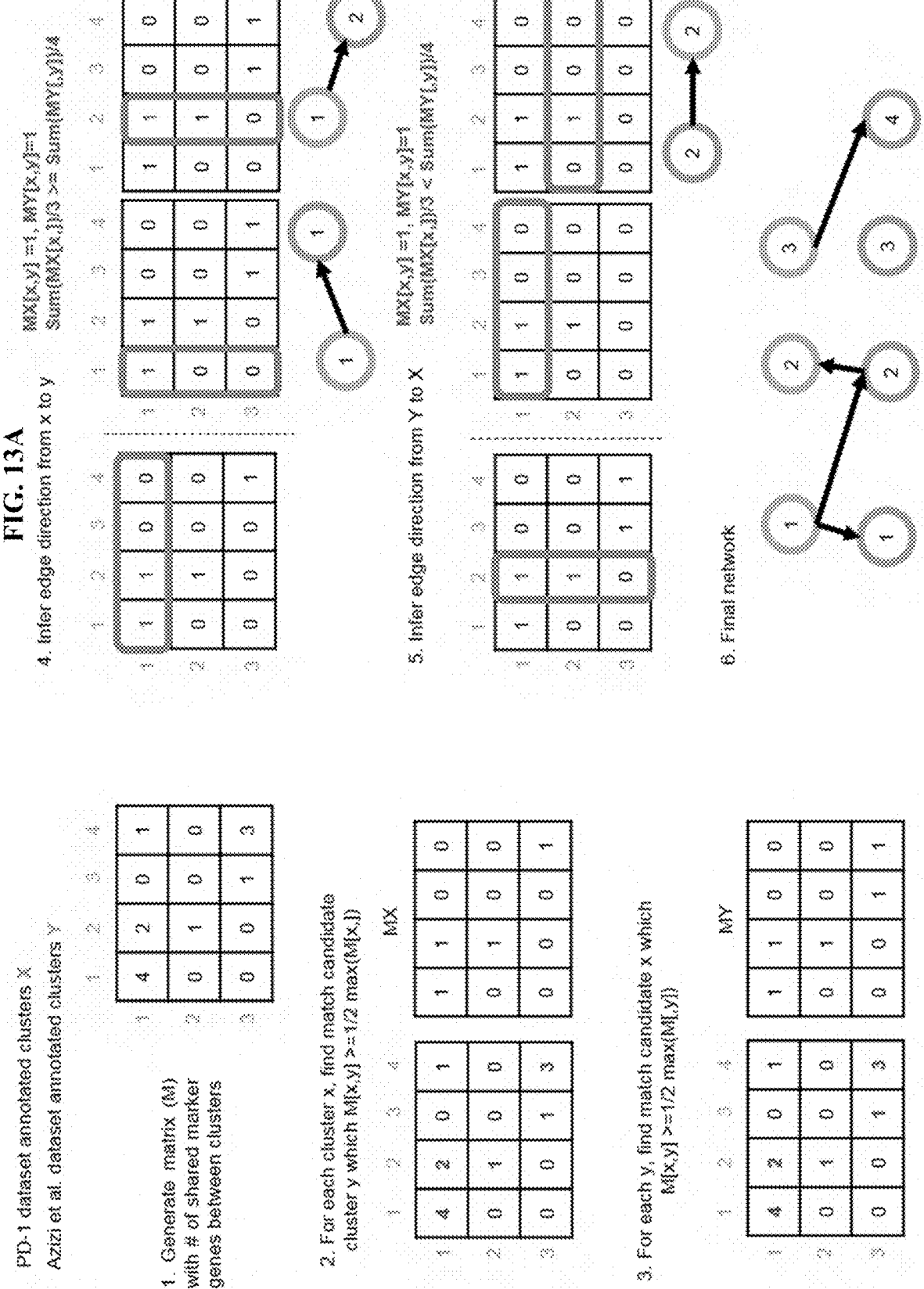
FIGS. 13A-E illustrate the connections between PD-1 dataset annotated clusters and public dataset clusters. Cell type annotations determined from anaylsis of transcriptional profiles of cells within the patient cohort applied to single cell data from two recent immune studies. The agreement between cell type annotations predicted for that dataset using our annotation algorithm (x-axis) is compared to the cell type annotations predicted by the authors of the previous studies (y-axis). The heatmaps show the frequency of agreement in cell type annotation.
Figure 13B:
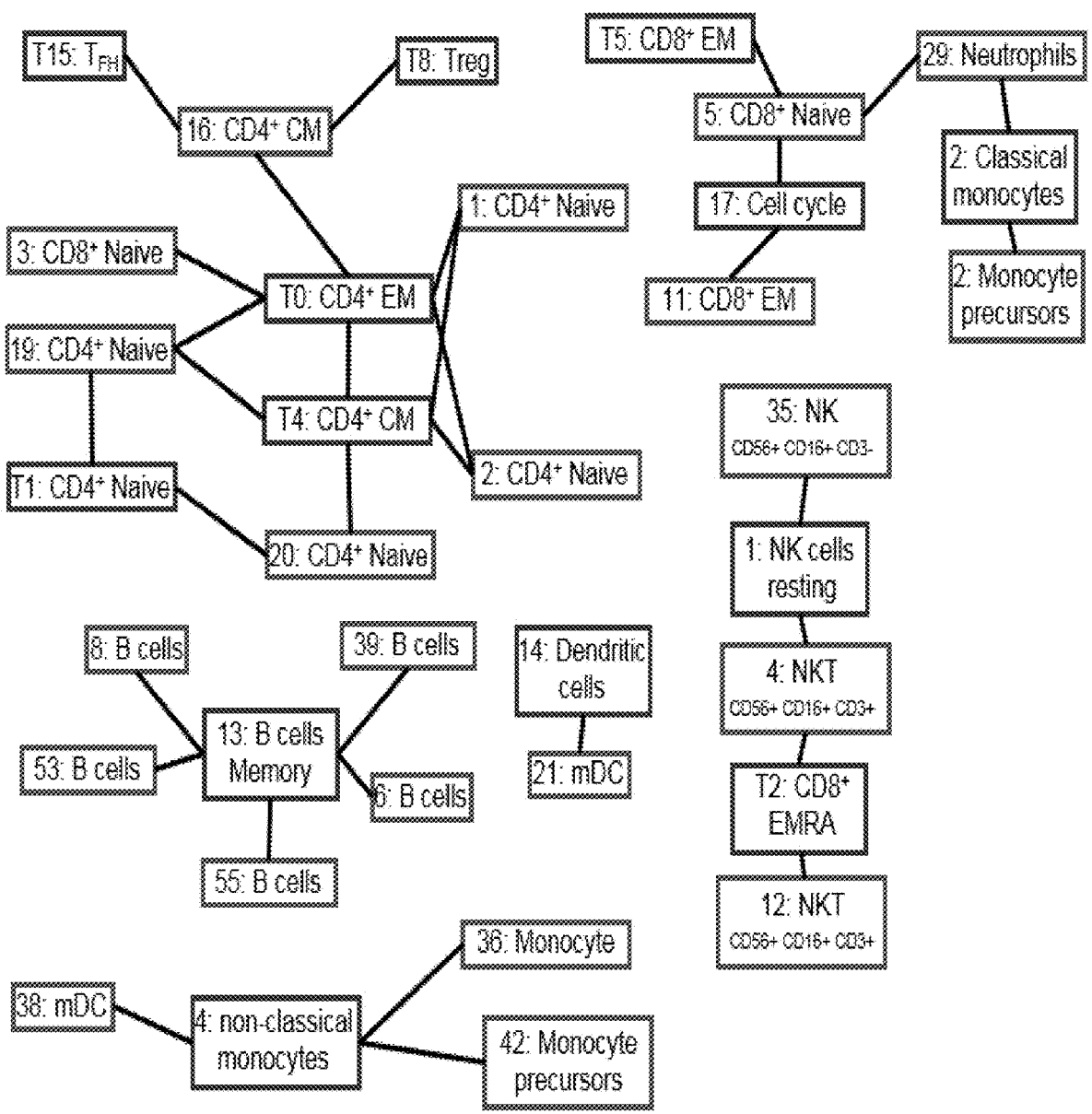
Figure 13C:
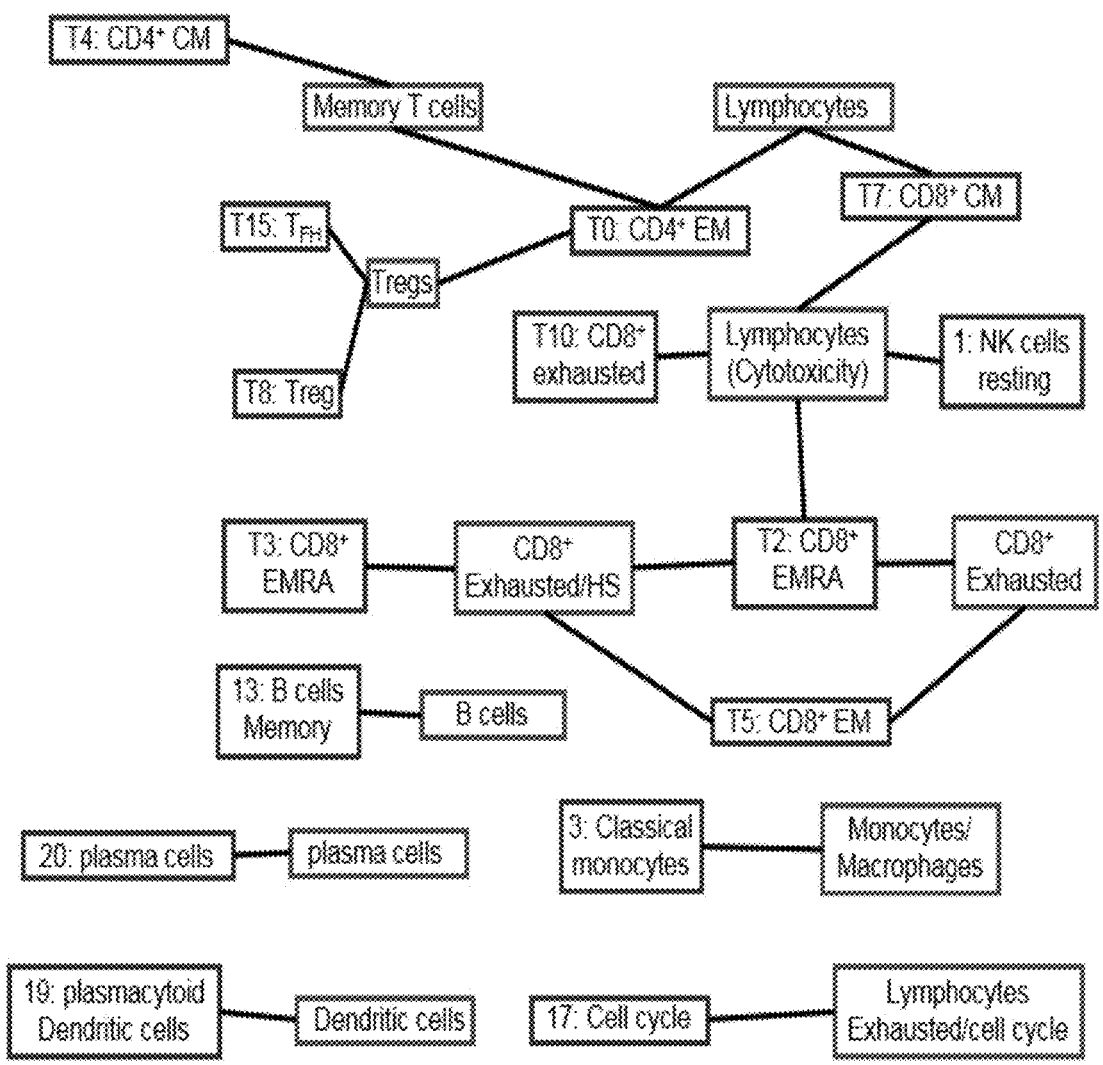
Figure 13D:
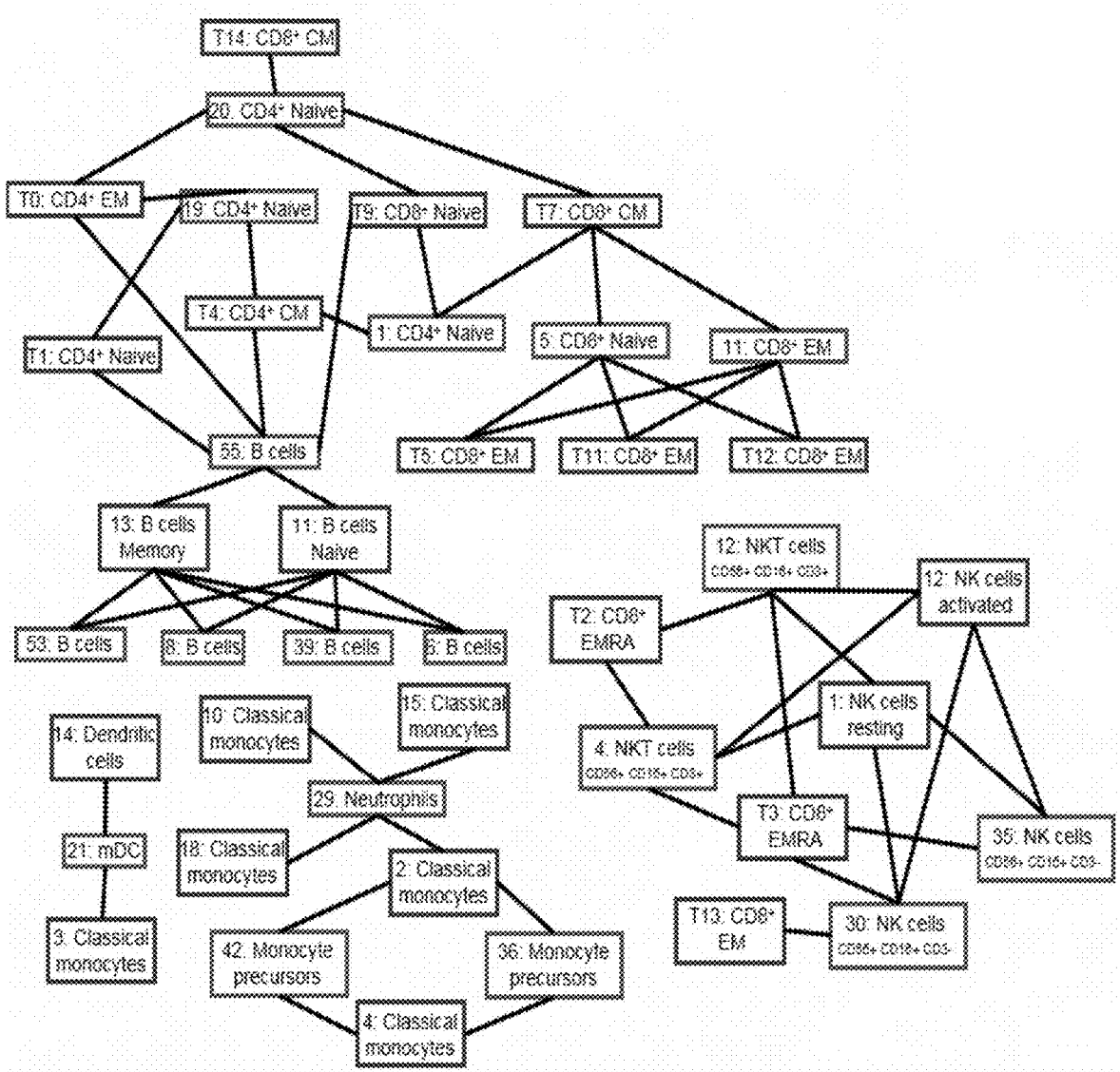
Figure 13E:
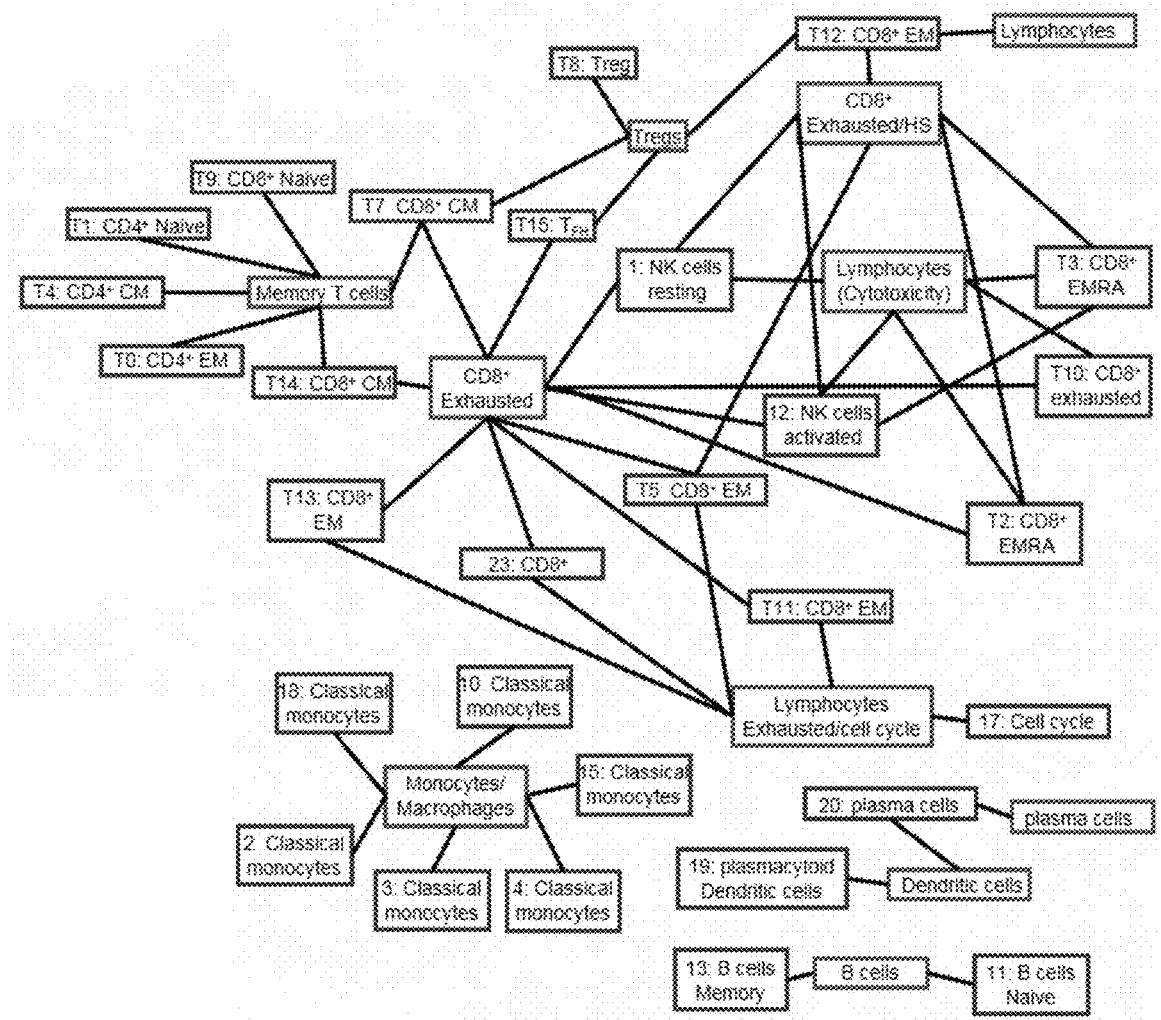
Figure 14:
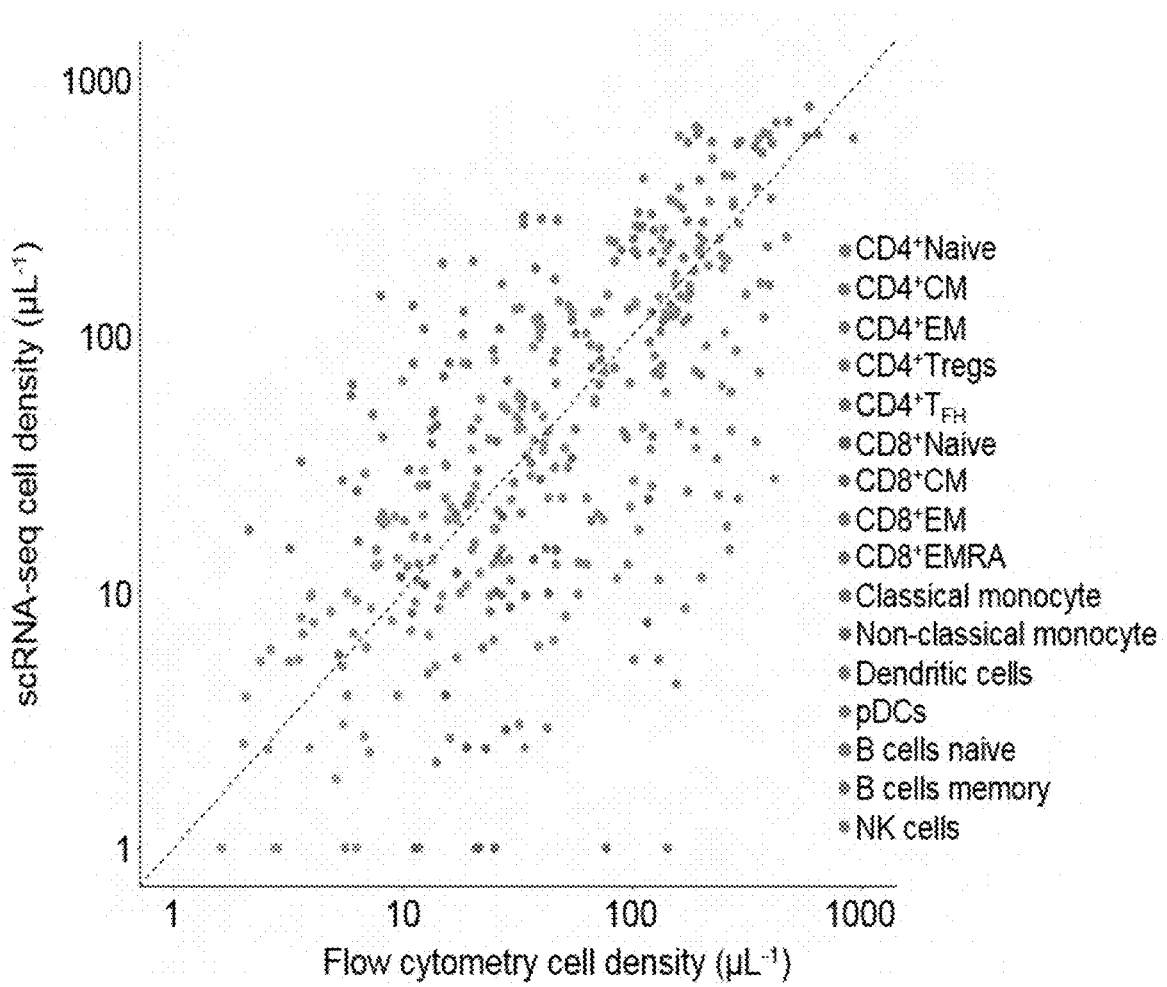
FIG. 14 is a plot providing a comparison of immune cell subtype densities, using scRNA-seq (Y-axis) or flow cytometry (X-axis) estimates. The densities of each cell subtype (colored points) were obtained scaling cell proportions measured by each method by the observed PBMC density in the blood sample. The cell subtype density was calculated for each patient, at each time point. The diagonal dashed line shows the 1:1 correspondence between the approaches.
Figure 15:
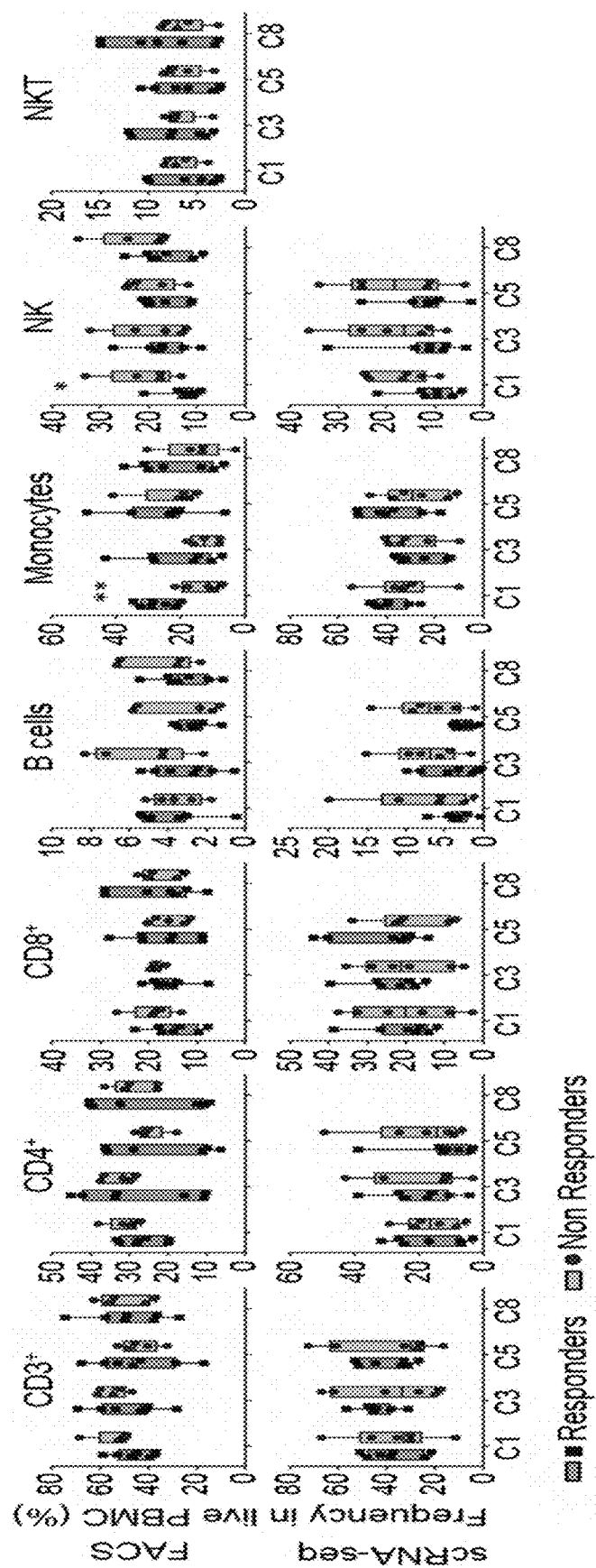
FIG. 15 are graphs illustrating that chemotherapy and immunotherapy induce no change in immune cell frequencies in both responders and non-responders except for monocytes and natural killer cells. Comparison of major cell population frequencies over the course of treatment obtained by flow cytometry (top) and scRNA-seq (bottom), where NK are natural killer cells, NKT are natural killer T cells, the statistical significance is displayed as *P<0.05, **P<0.01 (two-tailed unpaired t-test), C stands for cycle, 1 cycle is 14 days, C1 is the baseline, C3 is the chemotherapy FOLFOX regimen, and C5 is the chemotherapy+anti PD-1 immunotherapy regimen.

To confirm the cluster annotations, transcriptional profiles and corresponding annotations were compared to two publicly available scRNAseq datasets [See for example Refs. 29, 30]. A machine learning classifier was used to compare our annotations with those of a profile of PBMCs [See Ref 30] and tumor infiltrating immune cells [See for example Ref. 29]. It was seen that 96.5% of T cells from the PBMCs (clusters with at least 10 PBMC cells) and 94.1% from the tumor infiltrating immune cells T cell clusters dataset were correctly predicted using the classifier (FIG. 2 panel (b), FIGS. 12A-B). Cluster marker genes were compared and found to have a similarly high agreement of cluster annotations (FIG. 2 panel (b), FIGS. 12A-B). The connections between the annotations herein and the published ones are shown in the network presented, and show an overall consensus in results with some refinement of cell subtype annotation between approaches (FIG. 13). As a final approach to validate our cell type annotations, 8 patients were profiled with both flow cytometry and scRNAseq. A high agreement in the total percentages of B cells and NK cells was found and a slightly lower agreement in the percentages of lymphocytes and monocytes with differences of 10% and 9%, respectively (FIG. 2 panels (c)-(d)). Further interrogation of the monocytes identified a cluster with a high percentage of activated platelet contamination. Without wishing to be bound by theory, this was likely due to activated platelets binding to the monocytes and partially explains the differences observed between the flow cytometry and scRNAseq analysis [See for example ref. 31]. This contaminated cluster was removed from further analysis. Overall, there was a similar level of major immune cell populations in the flow cytometry and scRNAseq analysis with differences likely due to the measurement of mRNA or protein. Additionally, flow cytometry benefits from high cell number throughput, allowing for the identification of rare immune populations, but lacks the resolution of scRNAseq (FIG. 14). No change in population frequencies of identified major subtypes (T cells, NK, monocytes, and B cells) was observed, as determined by scRNAseq and flow cytometry, after chemotherapy or PD-1i between responders and non-responders; however, at baseline, more monocytes and fewer NK cells in responders were detected by flow cytometry only (FIG. 15).

Activation of Responder T Cells after the Start of PD-1 Immunotherapy

To capture information from signaling states of immune cells that is distinct from cell counts, pathway activity analysis within individual immune cells was performed using single sample Gene Set Enrichment Analysis (ssGSEA) [See for example. Ref 32]. Enrichment scores were calculated using C2 and Hallmark pathway signatures [See for example Refs. 33, 34]. Pathway differences before therapy, during chemotherapy and during the early-immunotherapy phase of the trial were analyzed using a random effects linear modeling framework. This allows partitioning of the molecular effects of chemotherapy from the effects of immunotherapy and simultaneously accounts for patient-specific variation in expression. Pathway changes specific to the immune cells of responders, and those that were common to both responder and non-responder were identified (FIG. 2e). Overall, immune cell gene expression was not changed upon chemotherapy treatment (FIG. 2e, left hand panel in red); however, specific changes common to all patients in NK, monocytes and T cells, including interferon (IFN) signaling after the start of PD-1i (FIG. 2e, middle pane), as well as signaling changes specific only to responders were detected (FIG. 2e, right hand panel in black).

Figure 3A:
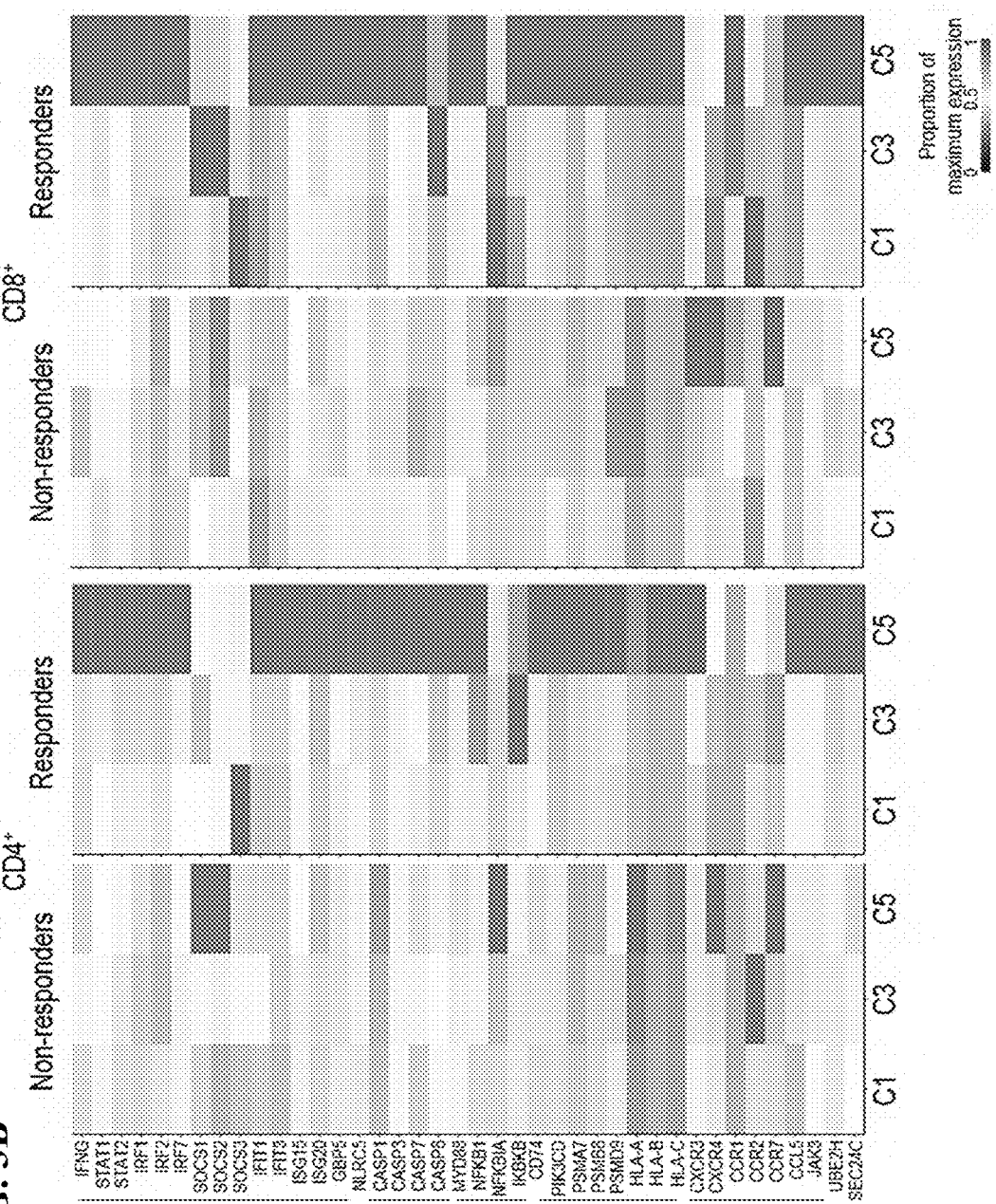
FIGS. 3A-D illustrate that pathway signaling evolution is dynamic in immune cell subtypes upon immunotherapy in responder patients.
Figure 3B:
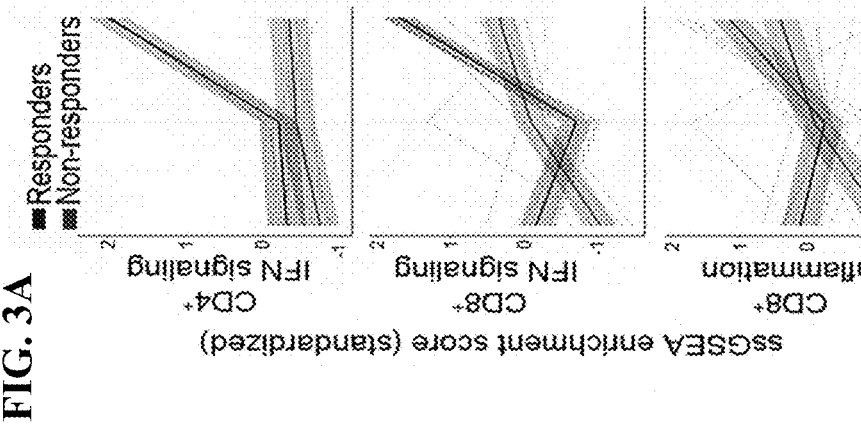
Figure 16:
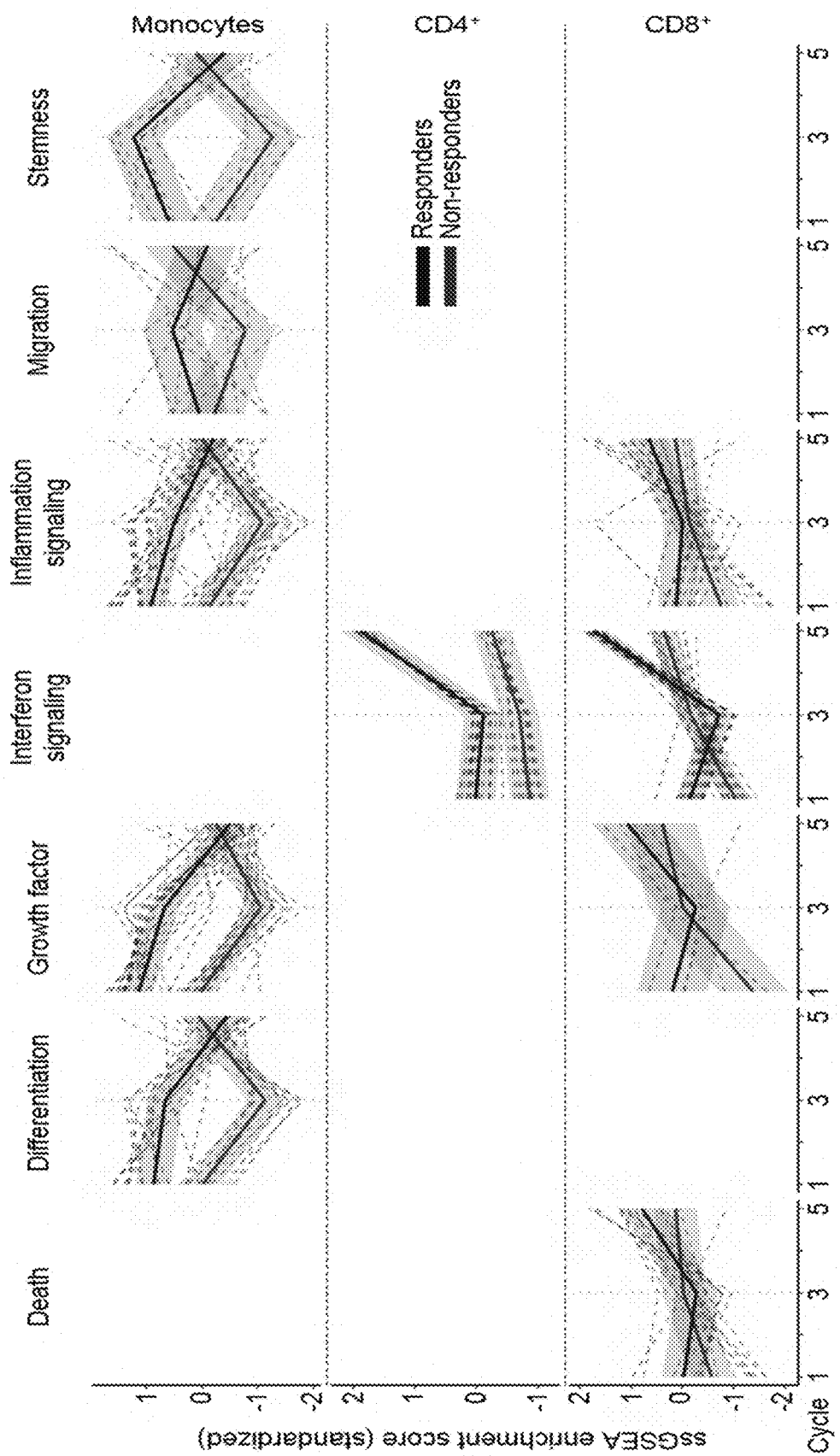
FIG. 16 are plots showing the overview of differential temporal trends in monocyte and T cell pathway expression between responders and non-responders. Response (red or blue) related differences in pathway activity was identified relating to: cell death, differentiation, growth factor production, interferon, and inflammatory signaling, migration and stemness. These pathway changes are visualized when present for monocytes, $CD4^+$, and $CD8^+$ T cells. Trends of pathways exhibiting differential expression patterns in responders and non-responders are indicated by dashed lines. Overall trends of pathways within each cellular process (solid lines) and variation (shaded red or blue regions) are overlaid.

Next, specific signaling pathway dynamics in subpopulations of T cells and monocytes were analyzed. Pathway activity was measured in every single cell as above, and pathways were categorized into key phenotypes, including interferon, inflammation, growth and differentiation signaling states. Interferon pathway activity in both CD4+ and CD8+ T-cells was strongly upregulated in responder patients following the initiation of PD-1i (C3-C5) (CD4: t=19.00, p<0.001, CD8 t=16.00, p<0.001) (FIG. 3A, FIG. 16). CD8+ T cells of non-responders show upregulation of interferon pathway activity signaling after the start of PD-1i while CD4+ T cells were not significantly increased (t=7.607 p<0.001). GSEA IFN pathway genes were significantly upregulated in the CD8+ and CD4+ T cells of responders (FIG. 3B, FIG. 17). After the start of PD-1i, responders showed significantly higher upregulated gene expression of IFN-γ in CD8+ cells than non-responders (p<0.01) (FIG. 3B) [also, see for example Ref. 35]. This translated to significant upregulation of IFN downstream signaling gene expression (IRF1/2/7 and STAT1/2 and interferon-stimulated gene (ISG) expression such as IFIT family members and GBPs in responder CD8+ and CD4+ T cells (data not shown). In contrast, non-responders showed significantly higher upregulation of SOCS1 and SOCS2 gene expression in CD4+ and CD8+ T cells (p<0.05). Without wishing to be bound by theory, because SOCS can repress IFN signaling, we concluded that CD4+ and CD8+ T cells of non-responders are unable to effectively induce IFN signaling upon PD-1i treatment. [See for example Ref. 35].

Distinct inflammatory responses in the gene expression profile of responder T cells was identified (FIG. 3A). Responders' CD8+ T cells had a greater inflammatory response prior to the onset of the trial (t=5.14, p<0.001), although not after the two cycles of chemotherapy. The addition of PD-1i induced a significantly stronger inflammatory response in the CD8+ T cells of responders than in non-responders (t=3.8, p<0.001). This inflammation included significant upregulation of CD74, HLA-A/B/C and PSM genes, which are directly involved in the sorting and processing of major histocompatibility complex (MHC) class I and II (FIG. 3B). In addition to MHC modulation, responder CD8+ and CD4+ T cells had significantly higher upregulation of NF-κB pathway genes. Specifically, expression of NFKB1 and MYD88 genes is upregulated significantly more in responders than in non-responders after the start of PD-1i while promoter (IKBKB) and inhibitor (NFKBIA) of NF-κB expression were upregulated and downregulated, respectively. NF-κB activation suggests an overall pro-survival state of these cells. Responder CD8+ and CD4+ T cells also upregulated chemokines that initiate immune cell recruitment (e.g. CCL3/4/5) (FIGS. 17A-C).

Figure 17A:
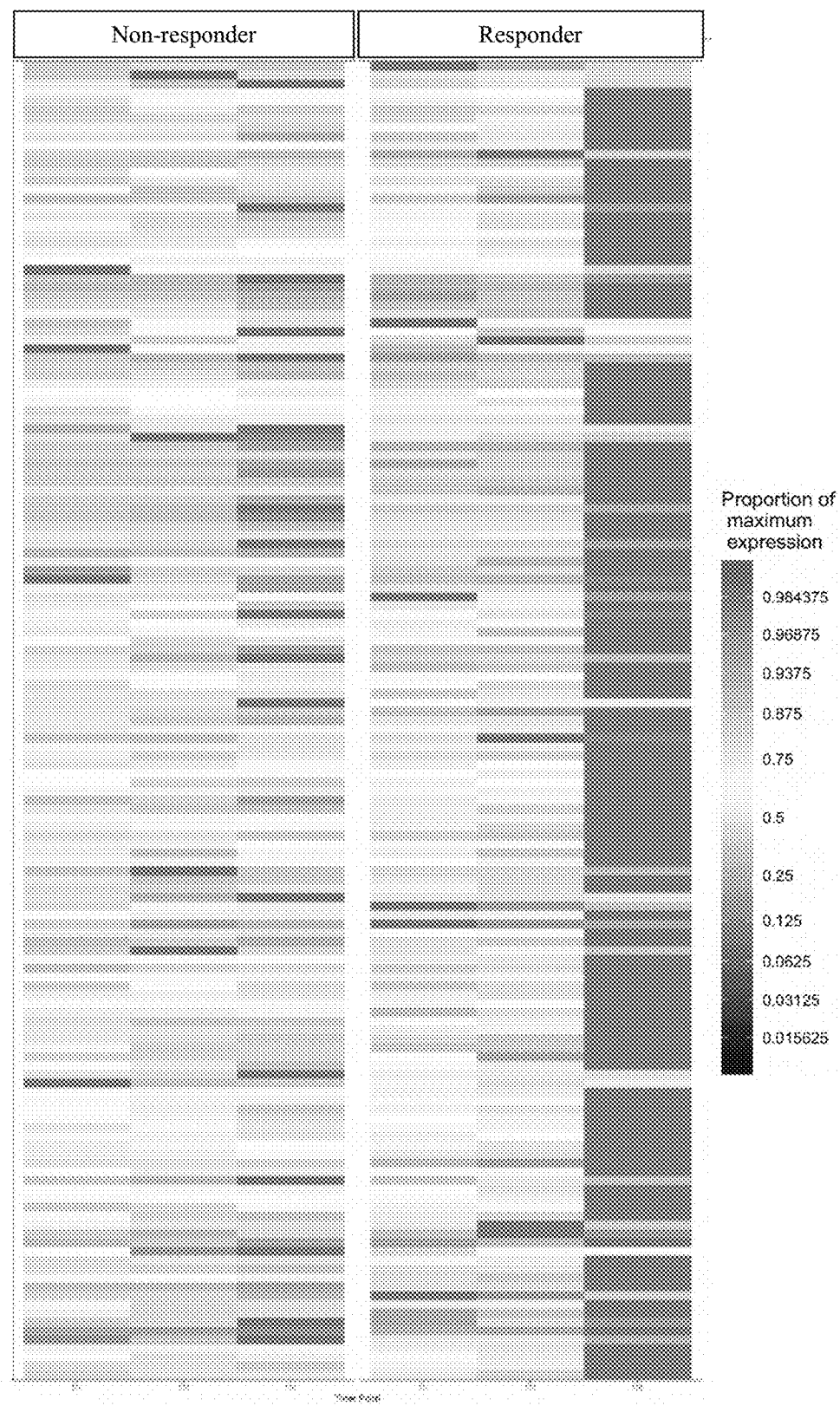
FIGS. 17A-C illustrate gene expression data showing that responders' $CD4^+$ and $CD8^+$ T cells show upregulation of IFN gene signature pathways following the addition of anti-PD-1 immunotherapy, as shown in cell density vs. differentiation plots. Heatmaps showing the changes in IFN (interferon) pathway-related gene expression of responders and non-responders $CD4^+$ and $CD8^+$ T cells over time are plotted. Gene expression is displayed as the proportion of the maximum level of each gene, compared at time points C1 (baseline, left), C3 (start of chemotherapy FOLFOX regimen, middle) and C5 (two cycles of anti-PD-1 immunotherapy in addition to chemotherapy, right). Results for non-responders are on the left, and responders on the right.

FIG. 17A presents results for gene expression data for the following genes, from top to bottom, ZFP36L2, ZBP1, XRCC6, XAF1, WARS, VAMP5, USP18, UBE2L6, UBA7, TYMP, TXNIP, TRIM26, TRIM25, TRIM22, TRIM21, TRIM14, TRAFD1, TNFSF10, TMEM140, TAP1, STAT2, STAT1, ST8SIA4, ST3GAL5, SSBP1, SRSF2, SRP9, SP110, SP100, SOCS3, SOCS1, SMAD4, SLC25A28, SKP1, SHFM1, SDCBP, SAMHD1, SAMD9L, SAMD9, RTP4, RNF213, RIPK2, RHOC, RBCK1, RBBP4, RARRES3, PTPN6, PTPN2, PTPN1, PSME2, PSME1, PSMB9, PSMB8, PSMB10, PSMA3, PPP5C, PPP3CA, POLR2B, PNPT1, PML, PMAIP1, PLSCR1, PDXK, PARP9, PARP14, PARP12, PARP1, OGFR, OASL, OAS3, OAS2, OAS1, NUP93, NUB1, NMI, NLRC5, NCOA7, MYD88, MX2, MX1, MT2A, MOV10, LY6E, LIPA, LGALS3BP, LAP3, JAK2, ISG20, ISG15, IRF9, IRF7, IRF3, IRF2, IRF1, IL4R, IL15RA, IL15, IFNAR2, IFITM3, IFITM2, IFITM1, IFIT5, IFIT3, IFIT2, IFIT1, IFIH1, IFI6, IFI44L, IFI44, IFI35, IFI16, HIF1A, HERC6, HERC5, HADHB, HADH, GCH1, GBP4, GBP2, GBP1, FAS, EPSTI1, EPS15, ELK4, ELF1, EIF4E3, EIF2B1, EIF2AK2, DTX3L, DHX58, DDX60, DDX58, DDX17, CYCS, CFH, CD74, CD164, CASP8, CASP1, BTG1, BST2, BBC3, BAG1, B2M, ATP6V0B, APOL6, APOL1, APOBEC3G, and ADAR.

Figure 17B:
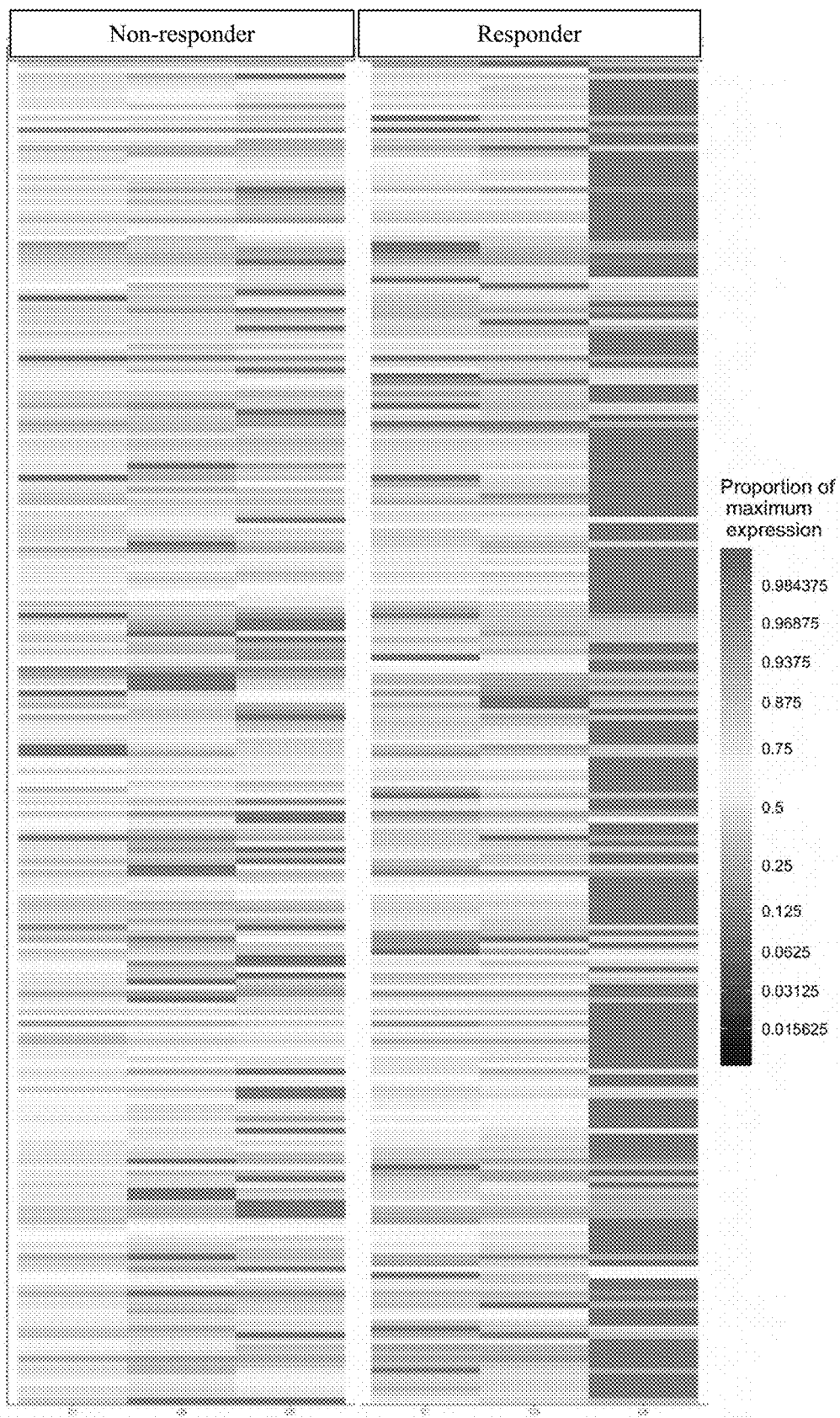

FIG. 17B presents results for gene expression data for the following genes, from top to bottom, ZFP36L2, ZBP1, XRCC6, XAF1, WARS, VAMP5, USP18, UBE2N, UBE2L6, UBE2E1, UBA7, UBA52, TYMP, TYK2, TXNIP, TRIM26, TRIM25, TRIM22, TRM21, TRIM14, TRAFD1, TPR, TNFSF10, TMEM140, TAP1, SUMO1, STAT3, STAT2, STAT1, ST8SIA4, ST3GAL5, SSBP1, SRSF2, SRP9, SP110, SP100, SOCS3, SOCS1, SMAD4, SLC25A28, SLAMF7, SKP1, SHFM1, SEH1L, SDCBP, SAMHD1, SAMD9L, SAMD9, RTP4, RPS27A, RNF213, RNASEL, RIPK2, RHOC, RBCK1, RBBP4, RARRES3, RANBP2, RAE1, PTPN6, PTPN2, PTPN1, PSME2, PSME1, PSMB9, PSMB8, PSMB10, PSMA3, PRKCD, PPP5C, PPP3CA, PPM1B, POM121, POLR2B, PNPT1, PML, PMAIP1, PLSCR1, PLCG1, PINE PIAS1, PDXK, PARP9, PARP14, PARP12, PARP1, OGFR, OASL, OAS3, OAS2, OAS1, NUPL2, NUPL1, NUP93, NUP88, NUP85, NUP62, NUP54, NUP50, NUP43, NUP37, NUP35, NUP214, NUP210, NUP205, NUP188, NUP155, NUP153, NUP133, NUP107, NUB1, NMI, NLRC5, NFKB1, NCOA7, NCAM1, MYD88, MX2, MX1, MT2A, MOV10, MAPK3, MAPK1, MAP2K6, LY6E, LIPA, LGALS3BP, LAP3, KPNB1, KPNA5, KPNA4, KPNA3, KPNA2, KPNA1, JAK2, JAK1, ISG20, ISG15, IRF9, IRF7, IRF3, IRF2, IRF1, IP6K2, IL4R, IL2RB, IL18BP, IL15RA, IL15, IFNGR2, IFNGR1, IFNG, IFNAR2, IFNAR1, IFITM3, IFITM2, IFITM1, IFIT5, IFIT3, IFIT2, IFIT1, IFIH1, IFI6, IFI44L, IFI44, IFI35, IFI16, ICAM1, HIF1A, HERC6, HERC5, HADHB, HADH, GCH1, GBP5, GBP4, GBP2, GBP1, FLNB, FAS, EPSTI1, EPS15, ELK4, ELF1, EIF4G3, EIF4G2, EIF4G1, EIF4E3, EIF4E2, EIF4E, EIF4A3, EIF4A2, EIF4A1, EIF2B1, EIF2AK2, DTX3L, DHX58, DDX60, DDX58, DDX17, CYCS, CISH, CFH, CEBPD, CD74, CD44, CD164, CASP8, CASP7, CASP3, CASP1, CAMK2D, BTG1, BST2, BBC3, BAG1, B2M, ATP6V0B, ARIH1, APOL6, APOL1, APOBEC3G, ADAR, and AAAS.

Figure 17C:
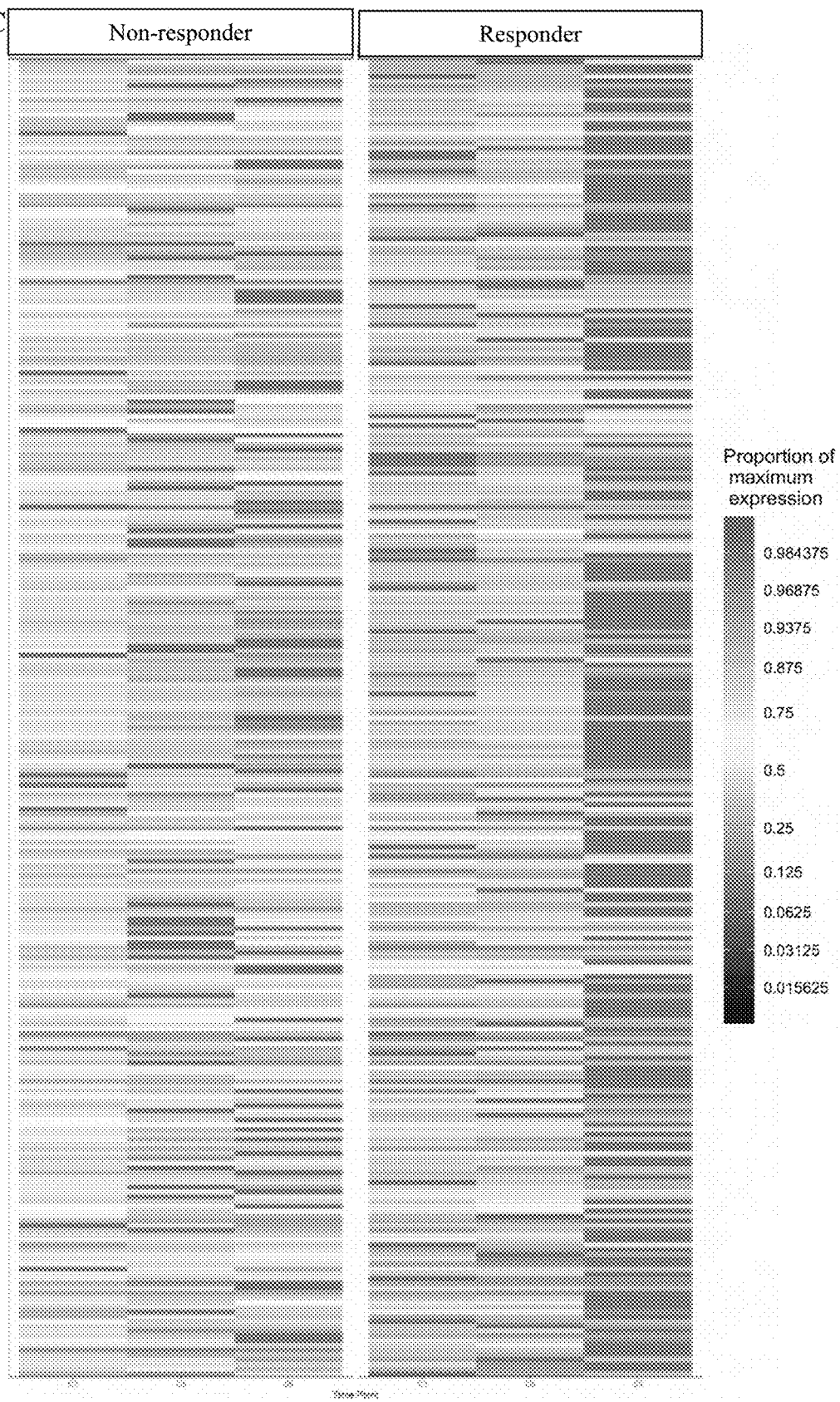

FIG. 17C presents results for gene expression data for the following genes, from top to bottom, ZBTB16, YWHAZ, YWHAB, YES1, WWP1, WSB1, VPRBP, VHL, VAV1, UBR4, UBR2, UBR1, UBOXS, UBE4A, UBE3C, UBE3B, UBE3A, UBE2Z, UBE2W, UBE2V2, UBE2S, UBE2R2, UBE2Q2, UBE2Q1, UBE2O, UBE2N, UBE2M, UBE2L6, UBE2L3, UBE2K, UBE2J2, UBE2J1, UBE2H, UBE2G2, UBE2G1, UBE2F, UBE2E3, UBE2E1, UBE2D4, UBE2D3, UBE2D2, UBE2D1, UBE2B, UBE2A, UBA7, UBA6, UBA52, UBA5, UBA3, UBA2, UBA1, TYROBP, TYK2, TRIP12, TRIM37, TRIM32, TRIM21, TRIM11, TRAF6, TPP2, TPI1, TNIP1, TCEB2, TCEB1, TAP1, TAB2, STUB1, STMN1, STAT5A, STAT3, STAT1, SSX2IP, SPSB2, SOS1, SOCS3, SOCS1, SMURF2, SKP2, SKP1, SHC1, SH3BGRL, SERINC3, SEC61G, SEC61B, SEC61A1, SEC31A, SEC24D, SEC24C, SEC24B, SEC23A, SEC13, SAR1B, SAE1, RPS27A, RNF6, RNF41, RNF4, RNF34, RNF25, RNE220, RNE138, RNE123, RIPK2, RELA, RCHY1, RBX1, RBCK1, RAF1, PTPN6, PSMF1, PSME4, PSME2, PSME1, PSMD9, PMSD8, PSMD7, PSMD6, PSMD5, PSMD4, PSMD3, PSMD2, PSMD14, PSMD13, PSMD12, PSMD11, PSMD10, PSMD1, PSMC6, PSMC5, PSMC4, PSMC3, PSMC2, PSMC1, PSMB9, PSMB8, PSMB7, PSMB6, PSMB5, PSMB4, PSMB3, PSMB2, PSMB10, PSMB1, PSMA7, PSMA6, PSMA5, PSMA4, PSMA3, PSMA1, PRKACB, PLCG2, PJA2, PJA1, PIK3R3, PIK3R1, PIK3CD, PIK3CB, PIK3CA, PDIA3, PDCD1, PCNA, OAS3, OAS2, OAS1, NRAS, NPFPPS, NFKBIA, NCF4, MX1, MKRN1, MAP3K8, MAP3K7, LYN, LRSAM1, LRRC41, LRR1, LNPEP, LCK, KRAS, KLRK1, KLHL9, KLHL20, KIF22, KEAP1, JAK2, JAK1, ITM2B, ITGB1, ISG15, IL7R, IL6S1, IL12RB1, IKBKG, IKBKB, IFNG, IFITM1, IFIT3, IFIT1, IFIH1, IFI44, ID3, ID2, ICAM1, HUWE1, HSPA5, HRAS, HERC2, HECTD3, H2AFV, GRB2, GBP1, GAN, FYN, FTH1, FBXW7, FBW11, FBX06, FBXO44, FBXO4, FBXO3, ERAP1, DZIP3, DTX3L, DNAJA1, DDX60, DCTN6, DBI, CYBA, CXCR3, CUL5, CUL3, CUL2, CUL1, CTSS, CTSD, CTSB, CTSA, CST3, CHUK, CDKN2C, CDC34, CDC27, CDC26, CDC23, CDC16, CD74, CCR5, CCR2, CCL5, CCL4, CCL3, CBLB, CBL, CASP1, CANX, CALR, BLMH, B2M, ATPIF1, ATG7, ASB8, ASB7, ASB6, ASB1, ARIH2, ANAPC7, ANAPC5, ANAPC4, ANAPC2, ANAPC13, ANAPC11, ANAPC10, ANAPC1, ALAD, and AHNAK.

The upregulation of ubiquitin and vesicle trafficking gene expression (UBE and SEC family members) further suggests the increased overall activation of these cells. In contrast, non-responder T cells downregulated genes related to the NF-κB pathway (decreased IKBKB and increased NFKBIA) as well as genes related to migration of immune cells, indicating an inactive state. These results indicate that the signaling state dynamics of immune cells in the peripheral blood could captures signaling information relevant to tumor response to immunotherapy. Responder T cell signaling states differ from those of non-responders, with T cells in responders upregulating inflammation and IFN signaling that may reflect better recruitment and activation of immune cells and a potentially greater capacity to detect and kill cancer cells.

Responders Exhibit Changes in Monocyte Signaling During Treatment

Figures 3C, 3D:
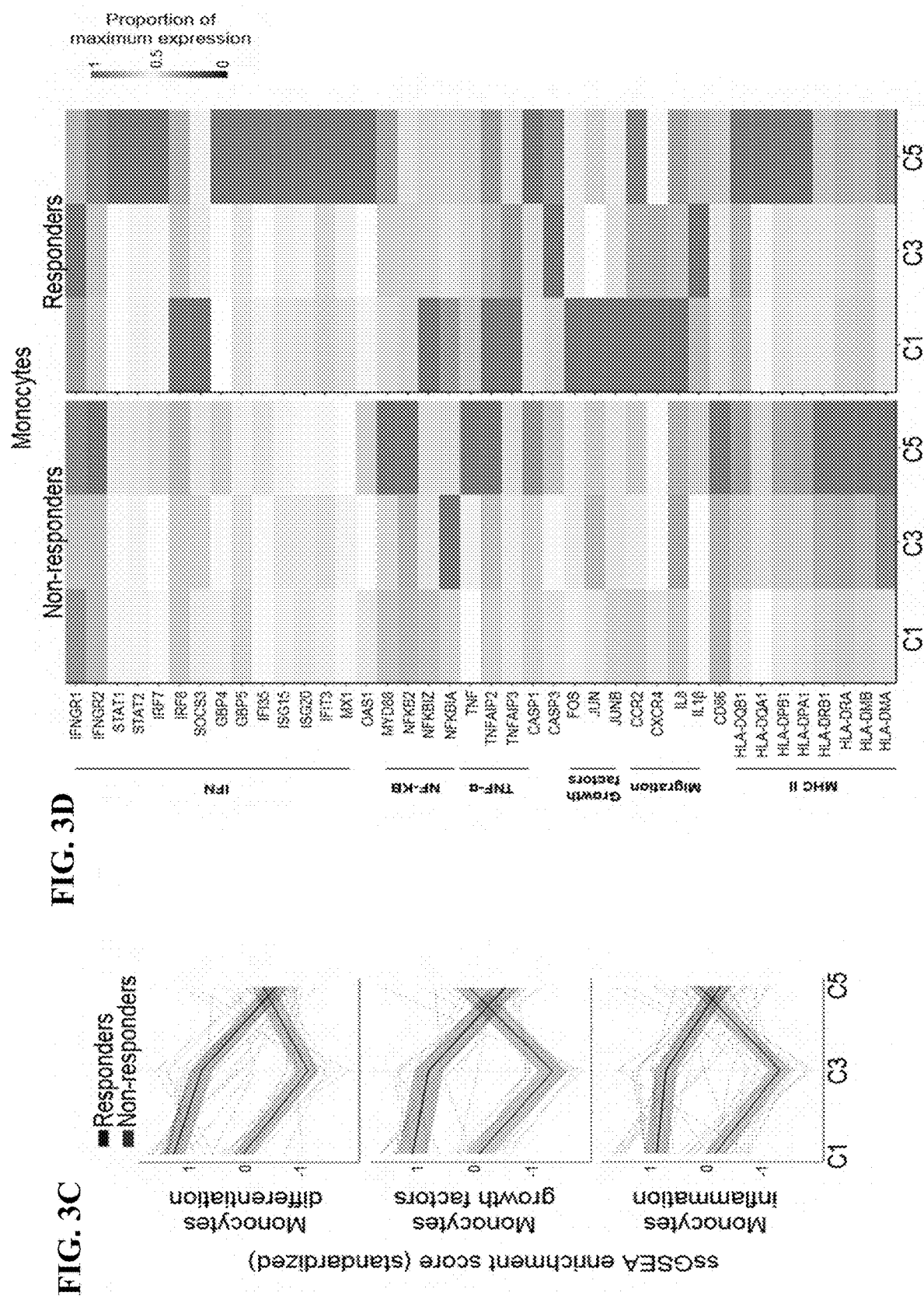

Monocytes also exhibit different phenotypes in responders and non-responders but with signaling changes from those in T cells. Before treatment (C1), responder monocytes had significantly higher activation of three pathways representing related but distinct measures of monocyte developmental states: growth factor production (t=9.2, p<0.001), inflammation (t=6.1, p<0.001), and differentiation (t=6.3, p<0.001) (FIG. 3D). Chemotherapy decreased each of these pathway scores in both responders and non-responders, but responders experienced a significant reduction in all three pathways after PD-1i treatment (p<0.001 for each pathway) while non-responders showed a significant increase (p<0.001 for each pathway).

At C1, responder monocytes had higher expression of genes involved in the inhibition of NF-κB pathway (i.e. NFKBIZ and NFKBIA) than non-responders (p<0.001) (FIG. 3D, FIGS. 18A-C).

Figure 18A:
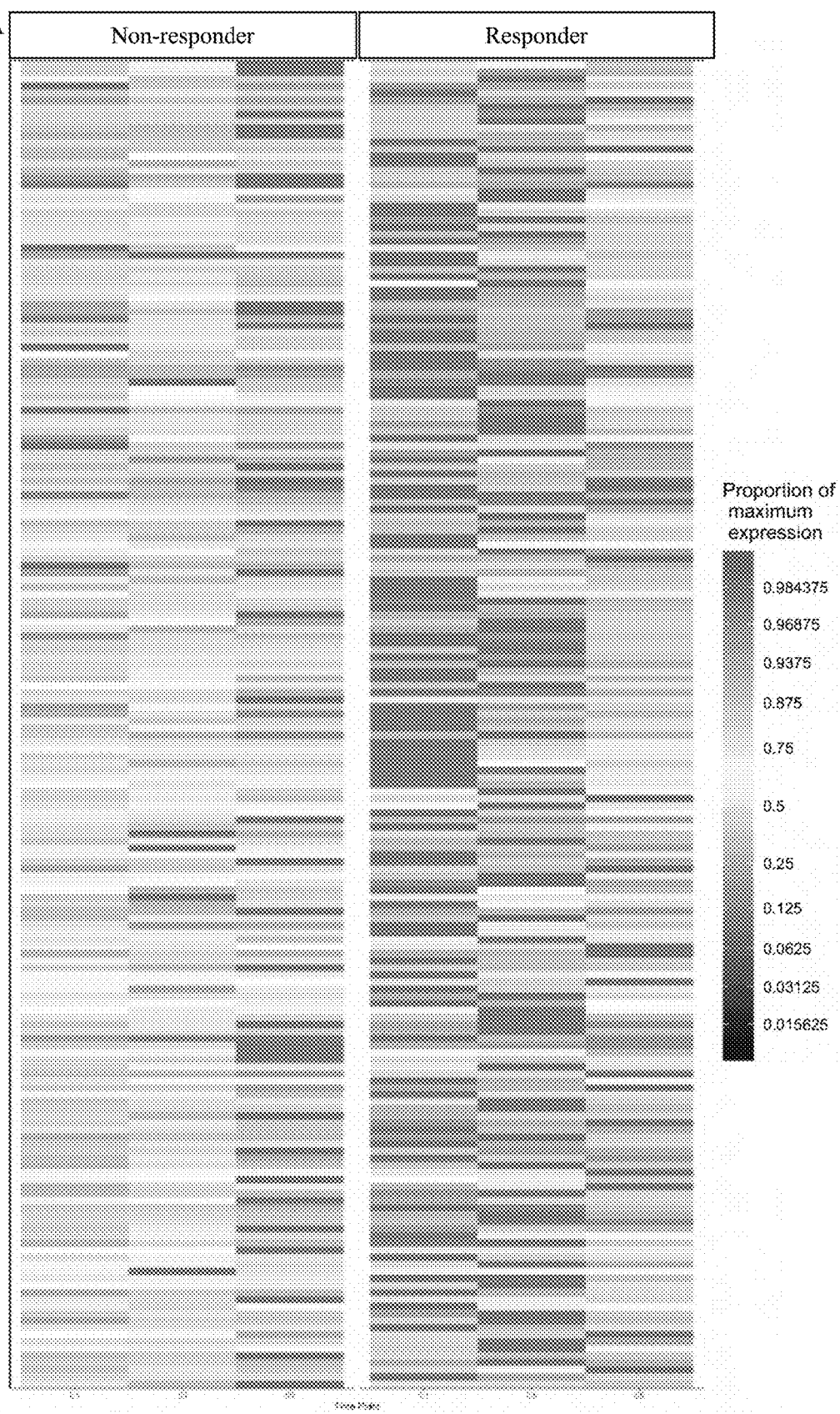
FIGS. 18A-C illustrate gene expression data showing that non-responder and responder monocytes show a different gene expression pattern of inflammatory, growth factor, and differentiation pathways before and in response to anti-PD-1 immunotherapy. Heatmaps of changes in monocyte differentiation, growth factor production and inflammatory response gene expression over time in responders and non-responders are plotted. Gene expression is displayed as the proportion of the maximum level of each gene. Expression compared at time points C1 (baseline, left), C3 (start of chemotherapy FOLFOX regimen, middle) and C5 (two cycles of anti-PD-1 immunotherapy in addition to chemotherapy, right). Results for non-responders are on the left, and responders on the right.

FIG. 18A presents results for gene expression data for the following genes, from top to bottom, ZSCAN16, ZNF217, ZNF107, ZFP36L2, ZFP36, ZFAND6, ZC3HAV1, ZBTB25, ZBTB20, WDR45, WDR37, VPS54, VOPP1, VEGFA, UGCG, UBE2H, UBAC2, TUBA4A, TTC39B, TSC22D1, TRIB1, TRA2B, TPP2, TP53INP1, TOP2B, TNFAIP3, TMEM64, THBS1, TCF12, TBC1D5, TBC1D15, TASP1, SUV420H1, STRN3, STAT5B, SOD2, SMAD1, SLC35B3, SIK3, SGMS1, SESN1, SEMA3C, SATB1, SAT1, SAMHD1, RNF125, RHOB, RGS2, RFX3, REEP3, RBL2, RBBP6, RB1, RAPGEF6, RABGAP1L, RAB8B, PTGS2, PTGER2, PSPC1, PSMA1, PPP3CC, PPP2R5C, PIP4K2A, PIM1, PIK3R1, PIK3IP1, PHTF2, PELI1, PDE4B, NUP153, NUDCD3, NSMCE2, NRBF2, NR4A2, NFKBIZ, NFIL3, NEK7, NCOA3, NCK2, MYC, MDFIC, MCL1, MBNL1, MAP4K4, MAP3K5, MAP3K1, MAN1A2, MAN1A1, MALT1, LTA4H, LRIF1, LRCH1, LATS2, L3MBTL3, KLF6, KLF3, KDM3A, KAT6B, JUNB, JUN, JMJD1C, JARID2, IRS2, IRF4, IRF2, IL7R, IGF1R, IFNAR2, IER3, ID2, IBTK, HIVEP2, HIF1A, HERPUD2, HEATR5A, HBS1L, GPRIN3, GPR183, GPHN, GLCCI1, GDI2, FOSL2, FOSB, FOS, FEM1C, FAS, FAM91A1, FAM76B, FAM3C, F2RL1, EXT1, EXOC6B, EVI5, ETS2, ETS1, ETNK1, ELK3, ELF1, EGR1, DUSP6, DUSP5, DOCK10, DNAJB4, DENND5A, CXCR4, CTSB, CREM, CPOX, CNOT6L, CNOT2, CITED2, CHD9, CELF2, CEBPD, CEBPB, CDKN1B, CDK19, CDK17, CDC42EP2, CD9, CCNG2, CBLB, CAST, C6orf62, C2lorf91, BTN2A1, BTG2, BTG1, BTBD10, BCL6, BARD1, BAG3, BACH1, B3GNT2, ATP2B1, ATP1B3, ATF3, ATAD2B, ASXL2, ARL4A, ARID5B, ARHGEF3, ARHGAP5, ARHGAP15, AKAP13, ADM, ADD3, and ABT1.

Figure 18B:
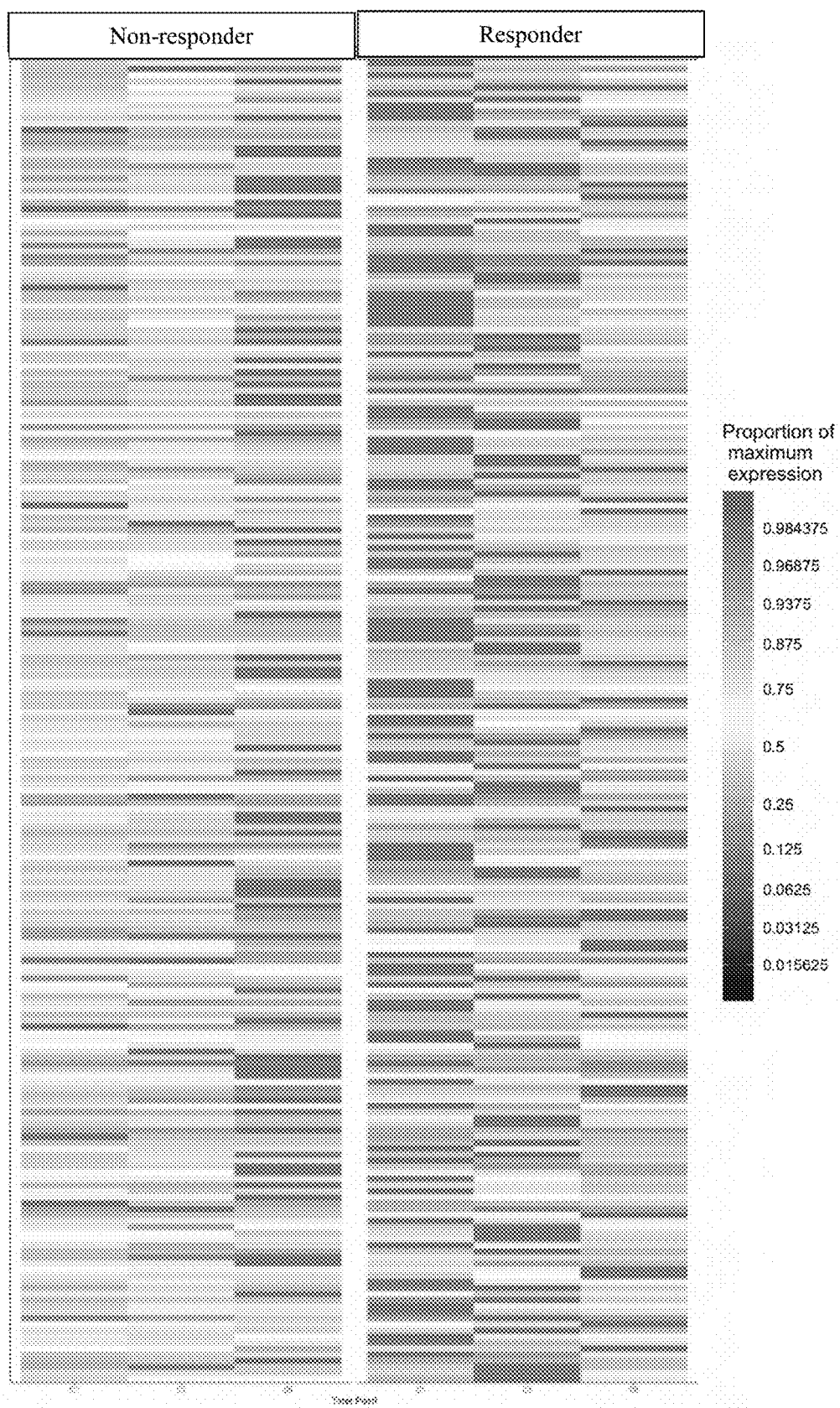

FIG. 18B presents results for gene expression data for the following genes, from top to bottom, ZFP36, XBP1, VEGFA, TYK2, TTC9, TSC22D2, TSC22D1, TRIB1, TNFAIP3, TNFAIP2, TLR7, TLR2, TLE3, TJP2, TIMP1, THBD, TGIF1, TGFBR1, SYK, STAT5B, STAT5A, STAT3, STAT1, ST3GAL4, SQSTM1, SPHK1, SOS1, SOCS3, SLC2A3, SLC2A14, SIAH2, SHC1, SELL, SAT1, SAMSN1, RUNX1, RPAGD, RPS6KB1, RPS6KA5, RPS6KA3, RNF217, RNF19B, RIPK2, RHOB, RELA, REL, RAF1, PTX3, PTPRE, PTPN6, PTPN11, PTK2B, PTGS2, PTGER2, PRKCB, PPP2R5D, PPP2CA, PPP1R15A, POU2F1, PMAIP1, PLIN2, PLEKHG3, PLEK, PLAUR, PIM1, PIK3R1, PIK3CA, PIAS3, PHTF2, PFKFB3, PF4, PDGFC, P2RX4, NUAK2, NOD1, NFKBIZ, NFKBIA, NFKB2, NFIL3, NDRG1, NCOA3, MYC, MXD1, MOB3B, MGLL, MFSD2A, MEF2C, MCL1, MARCKSL1, MAPKAPK2, MAPK9, MAPK8, MAPK3, MAPK14, MAPK1, MAP3K8, MAP2K6, MAP2K4, MAP2K3, MAP2K2, MAP2K1, LTB, LRRC8C, LDLR, KLF6, KLF2, KLF13, KLF10, JUNB, JUN, JAK3, JAK2, JAK1, ITGAV, IRS2, IRF8, IRF4, IRF1, IL8, IL7R, IL6ST, IL6R, IL4R, IL3RA, IL2RG, IL2RB, IL13RA1, IFNGR2, IFI16, IER5, IER3, IER2, ICAM1, HUWE1, HRAS, HK2, HES1, HCK, HBEGF, GUCY1B3, GRB2, GPR65, GNPTAB, GNG2, GFOD1, GCH1, GBP4, GALNT3, GALC, GADD45B, GABARAPL1, GAB2, G0S2, FPR3, FOSL2, FOSB, FOS, FGL2, FCER2, FAM126B, F2RL1, ETS2, ETS1, ELK1, EHD1, EGFR1, DUSP6, DUSP5, DUSP1, DOK2, DENND5A, DCPS, CXCR4, CTSZ, CST7, CSNK2A1, COTL1, CLEC4A, CKAP4, CISH, CFLAR, CEBPD, CEBPB, CDKN1C, CDKN1A, CD86, CD83, CD79B, CD44, CD14, CCR5, CCNL1, CCND2, CCL5, CCL4, CCL3, CBL, CAPG, CA2, C4orf32, BTG3, BTG2, BTG1, BIRC3, BIRC2, BHLHE40, BCL6, BCL2L1, BATF3, BATF, ATF3, ARL4A, ARID5B, ANTXR2, AKT1, AK3, AGER, and ABCA1.

Figure 18C:
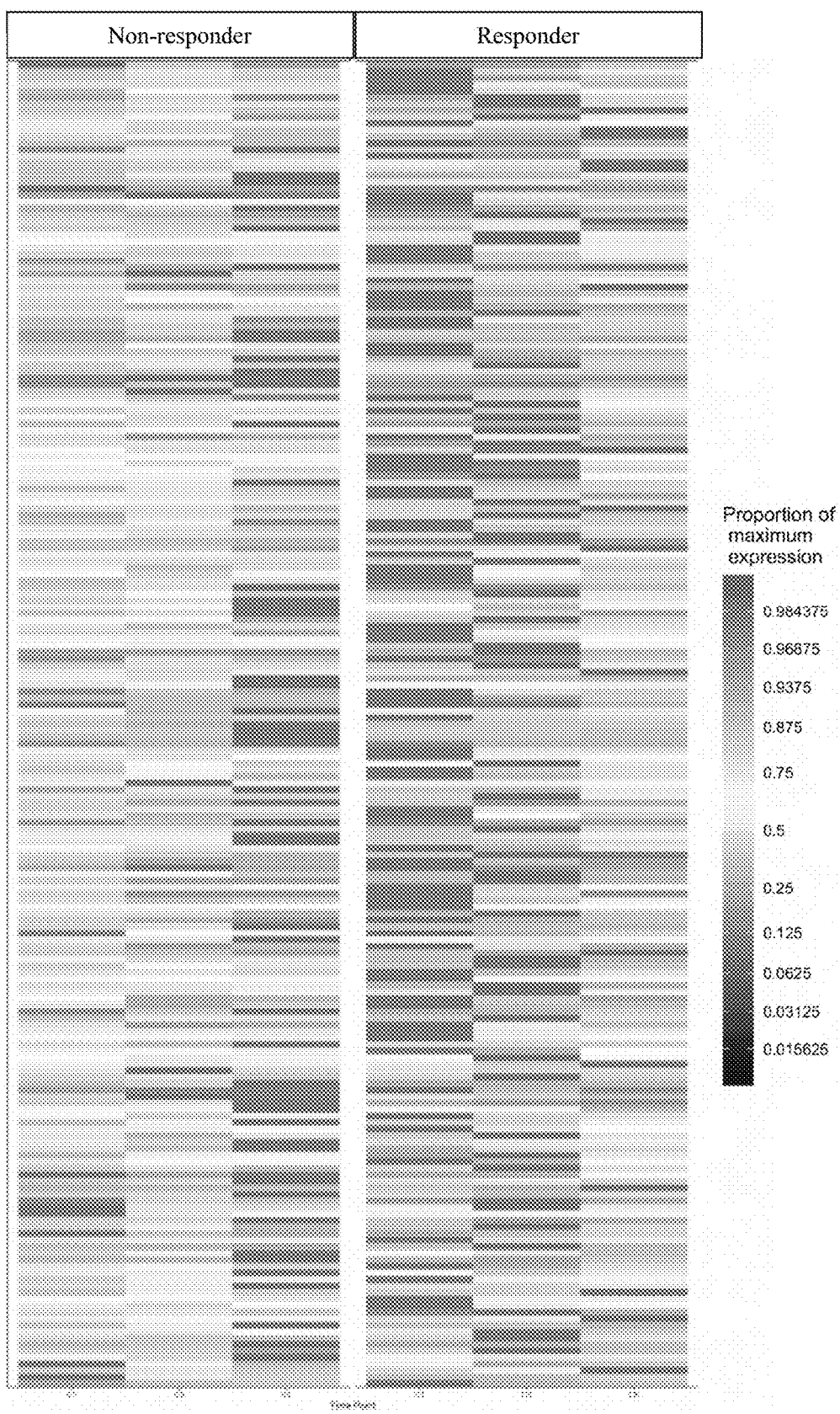

FIG. 18C presents results for gene expression data for the following genes, from top to bottom, ZFP36L2, ZFP36, ZFAND5, YRDC, VEGFA, VCL, USP12, UPP1, TSC22D1, TRIB E TPM1, TOP1, TOB1, TNFRSF10B, TNFAIP3, TMEM176B, TMEM176A, TIPARP, TIMP1, TIAM1, THBS1, TFRC, STAT3, SRF, SRC, SPHK1, SPARC, SOS1, SOCS3, SMAD7, SLK, SLC20A1, SLC12A2, SIK1, SHC1, SGMS1, SGK1, SERPINB8, RUNX1, RPS6KA5, RPS6KA3, RPS6KA1, RHOA, RGS2, RBMS1, RASA1, RAPGEF1, RAP1B, RAP1A, RAF1, PXN, PVR, PTX3, PTPRE, PTPN11, PTK2B, PTK2, PTGS2, PTEN, PRKCA, PPP1R15A, PPBP, PNPLA8, PMAIP1, PLEKHO2, PLAUR, PIM1, PIK3R1, PIK3CG, PIK3CA, PFKFB3, PER2, PER1, PDPK1, PDLIM5, PALLD, OXSR1, NR4A2, NR4A1, NFKBIZ, NFKB1, NEDD9, NDRG1, NAB2, MYD88, MYC, MTM1, MPZL2, MIR22HG, MEG3, MEF2C, MCL1, MBNL2, MAPKAPK2, MAPK8, MAPK7, MAPK3, MAPK14, MAPK1, MAP4K1, MAP3K8, MAP2K3, MAP2K1, LYN, LRRFIP1, LRRC8C, LDLR, LBH, KLF6, KLF4, KLF10, KDM6B, KCNN4, KBTBD2, JUNB, JUN, JOSD1, JAK1, ITPRIP, ITGAV, IRS2, INPP1, IL8, IL6R, IL1B, IKZF1, IGF1R, IER5, IER3, IER2, HRAS, HOMER1, HK2, HGF, HES1, HBEGF, GRB2, GNG11, GK, GALNT7, GADD45B, GADD45A, GAB1, G0S2, FRS2, FOXP1, FOSL2, FOSB, FOS, F2RL1, EZR, ETS2, ETS1, EPHB2, ELK1, EHD4, EHD1, EGR1, DUSP7, DUSP6, DUSP5, DUSP2, DUSP10, DUSP1, DST, DNMBP, DNAJB1 CYP1B1, CXCR4, CSNK2A1, CSNK1E, CSNK1D, CRKL, CRK, CREB1, CLCF1, CITED4, CEBPB, CD55, CD44, CCNL1, CBL, CASP9, C12orf44, BTBD3, BIRC3, BHLHE40, BCL3, BCL10, B3GNT5, ATF3, ATF1, ARHGAP6, ARHGAP25, ARAP2, AKT2, AKT1, AKIRIN1 AEN, ADRB2, ADM, ADAM8, and ADAM17.

Moreover, responder monocytes had upregulated TNF ($p<0.05$) and TNFAIP ($p<0.001$) expression known to inhibit NF-κB activation. Both transcription factors (JUN and FOS), related to growth factor signaling molecules are expressed at higher levels in responders (both $p<0.001$). We also found significant upregulation of CXCR4, CCR and CCL family members in responder monocytes, which promote migration and the recruitment of other immune cells. [Also, see for example Ref. 37]. After the start of PD-1i, responder monocytes significantly downregulate inflammation and growth-related genes, while non-responders monocytes upregulate genes related to NF-κB activation (NFKB2, BIRC3, AKT1 or RELA). Both non-responders and responders upregulated ISGs (STAT, GBP, IRF, IFIT family members) after commencement of PD-1i, yet this upregulation was markedly greater in responders ($p<0.001$). In addition, MHC II genes were upregulated in non-responders and responders after the start of PD-1i; however, responders have significantly higher expression of HLA-DQ and HLA-DP while non-responders have higher expression of HLA-DR. Gene expression of HLA-DM protein, which is involved in the intracellular processing of antigen presentation, is upregulated in both responders and non-responders. Upregulation of more antigen presenting receptor genes (HLA) by responder monocytes may confer an increased ability to activate other immune cells. Monocytes show significant pre-treatment differences in signaling and divergent evolutionary trajectories in responders versus non-responders. Activation of monocytes after the start of PD-1i may reflect responses to the upregulation of IFN and cytokine gene expression observed in responder T cells.

Evolution of Memory T Cell Densities in Response to Immunotherapy

Figure 4:
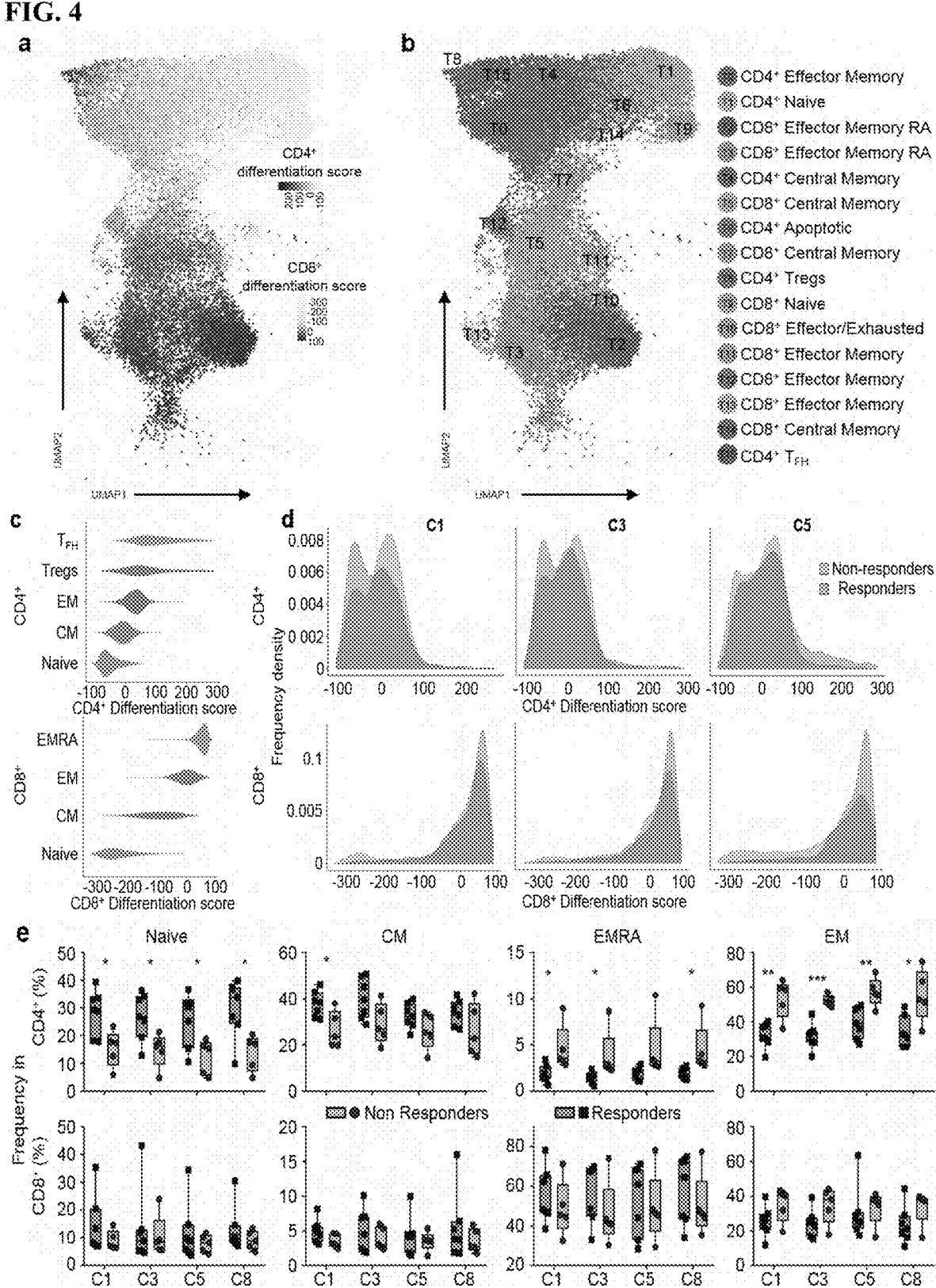
FIG. 4 presents data illustrating responsiveness to therapy is dependent on circulating memory T cell evolution. Panel (a) is a Uniform Manifold Approximation and Projection (UMAP), representing gradients of CD4$^+$ differentiation state (top: lowest score at right and highest to the left) and CD8$^+$ differentiation state (bottom: lowest score towards the top right and highest at the bottom). Panel (b) is a UMAP identification of CD4$^+$ and CD8$^+$ subclusters, where $T_{FH}$ is Follicular helper. Panel (c) is a plot comparison of CD4$^+$ and CD8$^+$ T cell subtype differentiation scores, where all subtypes differ with a Tukey test. The variables EM (Effector memory), EMRA (Effector memory CD45RA$^+$), CM (Central memory) are plotted vs. differentiation score. Panel (d) are graphs showing frequency of CD4$^+$ and CD8$^+$ T cells with different states of differentiation of responders and non-responders at each treatment time point (C1, C3, and C5). Panel (e) are graphs showing direct comparison of frequencies of CD4$^+$ (top) T cells and CD8$^+$ (bottom) subpopulations based on CCR7 and CD45RA markers.
Figure 19:
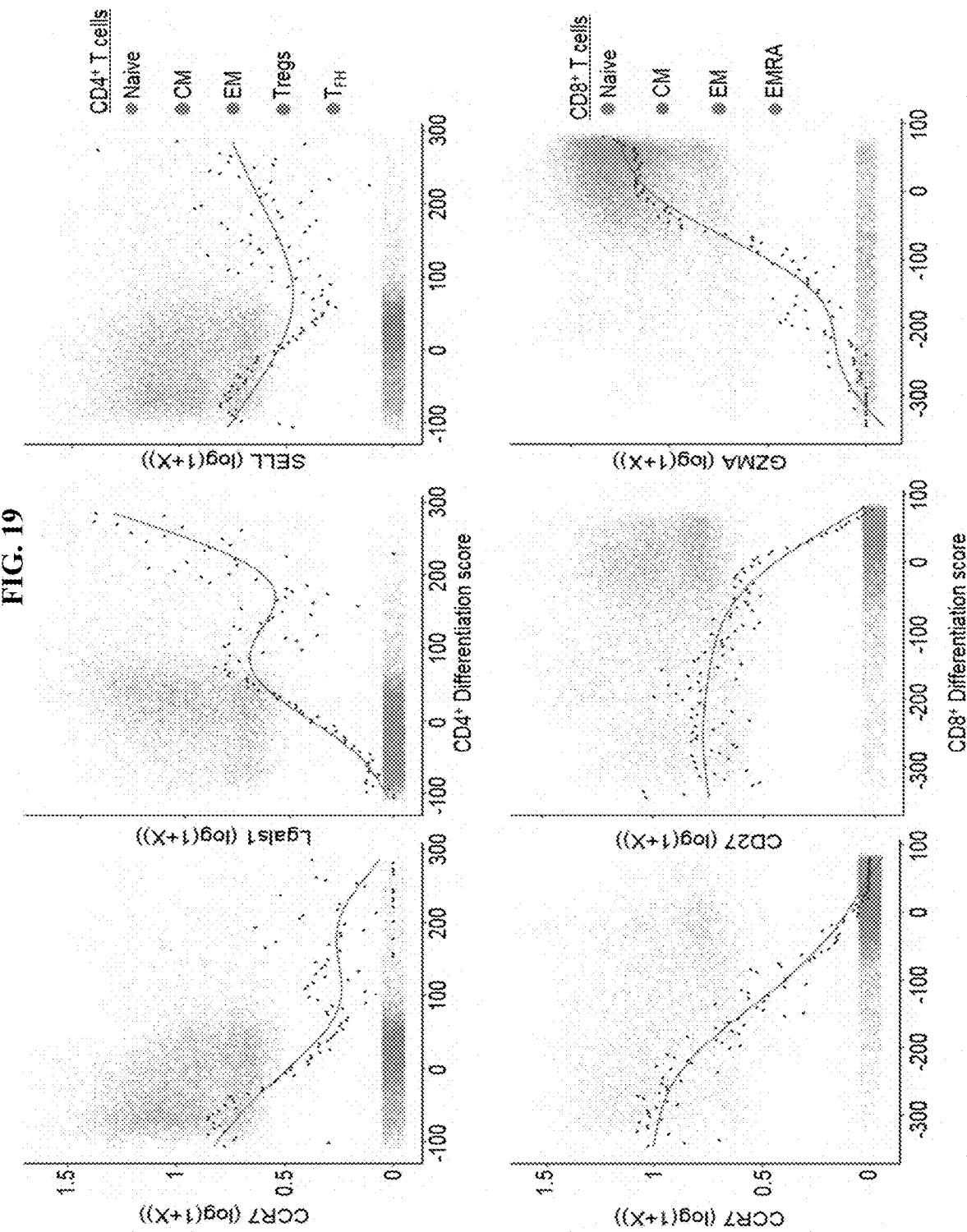
FIG. 19 are phenotype axes plots capturing the continuous spectrum of T cell differentiation states. Changes in $CD4^+$ and $CD8^+$ T cell gene expression are shown across the T-cell differentiation gradient. For each cell (dot) in each T cell subtype (color), the cell differentiation score is plotted against marker genes of naïve (CCR7) and effector states (LGALS1 and GZMA). Average expression of cells in small regions of the phenotype gradient are calculated, after discretizing the differentiation axis into 100 categories and classifying cells into these groups. A generalized additive model indicates the trend in gene expression across the phenotype gradient.

To evaluate the differences in differentiation and activation states of CD4$^+$ T cells, CD8$^+$ T cells, and monocytes between patients during treatment, major axes of phenotypic variation within each immune type from single-cell gene expression profiles were identified using pseudotime reconstruction (FIG. 4). Naïve T cells are CCRT7$^+$/CD45RA$^+$, the EM (Effector memory) T cells are CCR7$^-$/CD45RA$^-$, EMRA (Effector memory CD45RA$^+$) T cells are CCR7$^-$/CD45RA$^+$, CM (Central memory) T cells are CCR7$^+$/CD45RA$^-$, from right to left, and on the x-axis C stands for cycle, 1 cycle is 14 days, C1 is the baseline, C3 is the chemotherapy mFOLOFX6 regimen, C5 and C8 are Chemotherapy including anti-PD-1 immunotherapy. The statistical significance is displayed as *$P<0.05$, $P<0.01$ and *$P<0.001$ (two-tailed unpaired t-test), and box plots represent the interquartile range (IQR), with the horizontal line indicating the median. Whiskers extend to the farthest data point within a maximum of 1.5×IQR. These phenotypic traits were verified using zinbwave and principal component analysis dimension reduction methods (FIG. 19). By overlaying these phenotypic scores onto the uniform manifold approximation and projection (UMAP), we further validated that these traits reflect major sources of variation within the immune cell types (FIG. 4 panel (a)). For both CD4$^+$ and CD8$^+$ T cells, the major axes of phenotypic gradient related to differentiation states. The CD4$^+$ T cell phenotypic gradient captured a continuum of differentiation from naïve to effector helper T cells (FIG. 4 panel (a)). Canonical gene markers of T cell differentiation (e.g. CCR7 and S100A4) distinguished the naïve, central memory, and effector memory CD4$^+$ sub-types (FIG. 4 panel (b)). The expected order of cell type differentiation aligned clearly with the continuous phenotype gradient (FIG. 4 panel (c)). Similarly, the CD8$^+$ T cell phenotype gradient captured differentiation from naïve to highly cytotoxic cells. Naïve, central memory, effector memory, and effector memory CD45RA+ (EMRA) subtypes were identified. The strong agreement between CD8$^+$ T cell subtype classification and the cytotoxic phenotype scales reinforced the functional relevance of the T cell sub-types that were identified.

Figure 20:
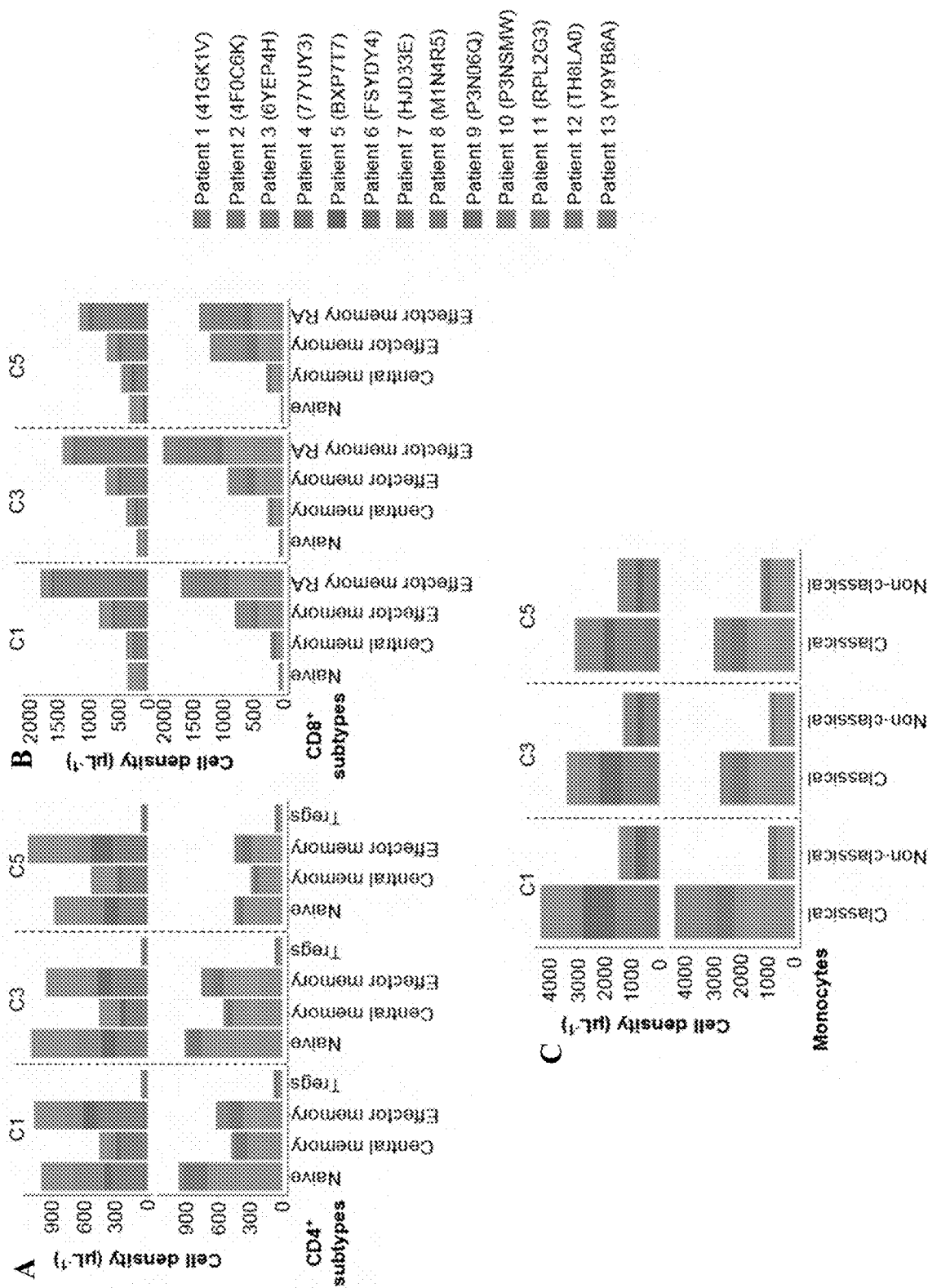
FIG. 20 shows graphs illustrating that the abundance of different immune cell subtypes in $CD4^+/CD8^+$ T cells and monocytes differs between responders and non-responders and over time. Immune cell densities are shown for each patient (color) for subtypes of: $CD4^+$ T cell as in Panel (a); $CD8^+$ T cell as in Panel (b); and monocytes as in Panel (c). Patients are grouped into responders and non-responders in each panel, and C stands for cycle, 1 cycle is 14 days, C1 is the baseline, C3 is the chemotherapy FOLFOX regimen, C5 is the chemotherapy+anti PD-1 immunotherapy regimen.

The distribution of T cell phenotypes in the peripheral blood population was assessed by calculating a phenotype score for each cell. Differences in the frequency of T cells with different scores were identified between responders and non-responders and over time. Before the trial (C1), responders had a higher frequency of undifferentiated (naïve) CD4$^+$ T cells, while non-responders had more differentiated CD4$^+$ T cells, especially CD4$^+$EM cells ($t=-7.5$, $p<0.001$). This difference remained following the onset of chemotherapy (C3). However, after the addition of immunotherapy (C5), the CD4$^+$ T cells of responders showed a significant shift towards increased differentiation ($t=9.9$, $p<0.001$) and in fact converged with non-responders (FIG. 4 panel (d), FIG. 20 panel (a)). In CD8$^+$ T cells, responders had a higher frequency of cytotoxic differentiated CD8$^+$ T cells than non-responders, both before and during treatment (FIG. 4 panel (d), FIG. 20 panel (b)) ($F=16.8$, $p<0.001$). With the addition of PD-1i, responder CD8$^+$ T cells became more differentiated ($t=3.9$, $p<0.001$), while non-responder CD8$^+$ T cells shifted to lower differentiation ($t=-4.0$, $p<0.001$).

In addition to the scRNAseq analyses, flow cytometry analysis using CD45RA and CCR7 as markers to discriminate memory from naïve T cells identified multiple significant differences in the CD4$^+$ population. Responders had a higher frequency of CCR7$^+$ CD45RA$^+$ CD4$^+$ naïve cells before and throughout treatment (FIG. 4 panel (e), FIG. 9). CD45RA$^-$/CCR7$^+$ CD4$^+$ CM cells were significantly more frequent in responders at the C1 and C3 time points but not after PD-1i treatment (C5). Conversely, CCR7$^-$/CD45RA$^-$ CD4$^+$ EM cells and CD45RA$^+$/CCRT CD4$^+$ EMRA cells were significantly more frequent in non-responders at all time points. CD8$^+$ subtypes showed no significant difference between responders and non-responders.

Responders Start Therapy with Exhausted Memory T Cells

Figure 5:
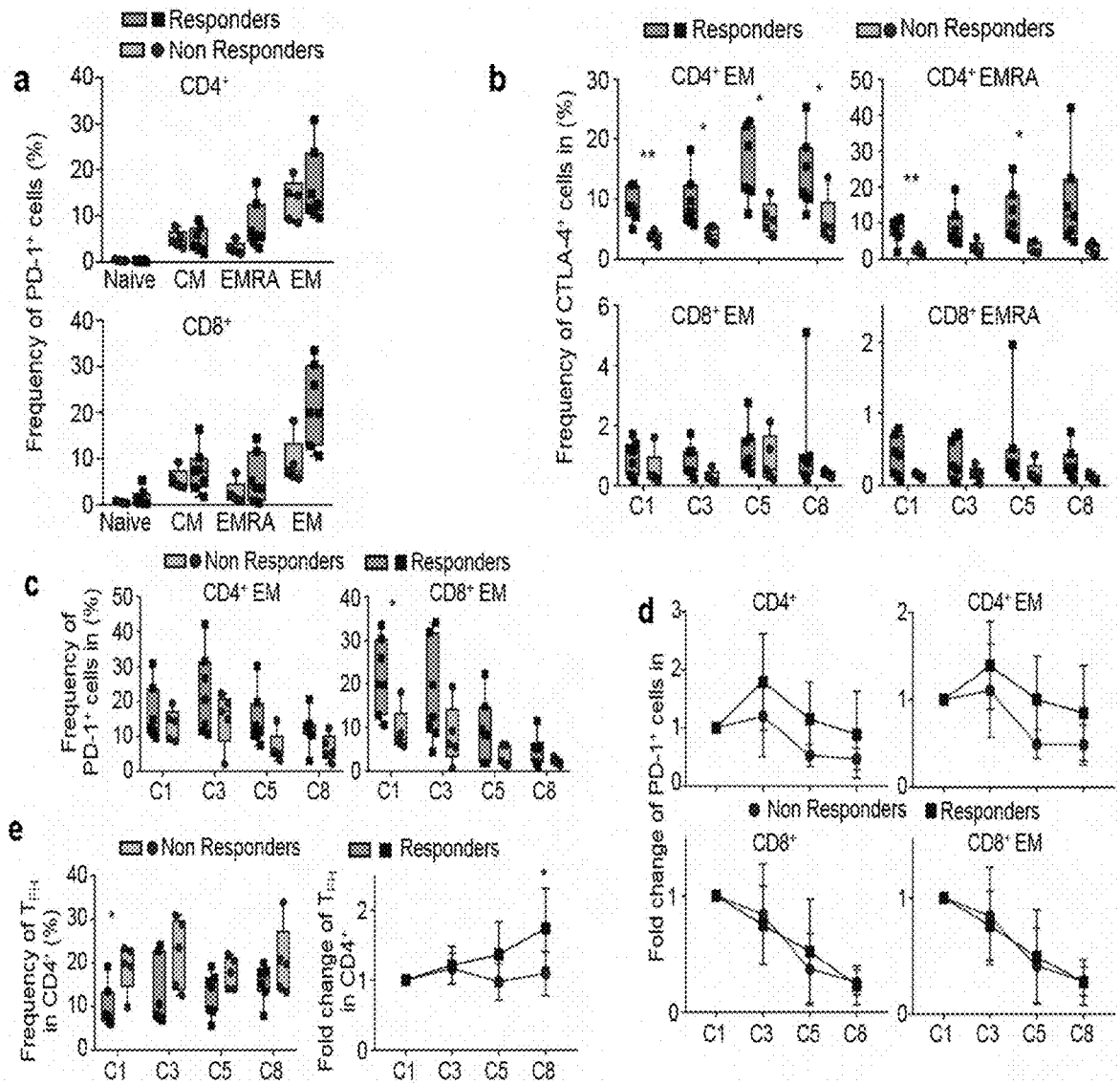
FIG. 5 presents data indicating that the exhaustion of circulating memory T cells is a hallmark of response prior to therapy. Panel (a) are plots showing frequencies of PD-1$^+$ cells in CD8$^+$ (left) CD4$^+$ (right) subpopulations at C1. Panel (b) are plots showing the frequencies of CTLA4$^+$ cells of CD4 EM or EMRA cells (top) and CD8$^+$ EM or EMRA cells (bottom) vs. cycles C1, C3, C5, and C8 (C stands for cycle, 1 cycle is 14 days, C1 is the baseline, C3 is the chemotherapy mFOLOFX6 regimen, C5 and C8 are Chemotherapy including anti-PD-1 immunotherapy). Panel (c) Are plots showing frequencies of PD-1$^+$ cells in CD4$^+$ EM or CD8$^+$ EM cells between responders and non-responders over the course of treatment. Panel (d) are graphs showing the fold change of PD1$^+$ cells of responders and non-responders over the course of treatment. Panel (e) are graphs showing the frequencies (left) and fold change (right) of $T_{FH}$ (Follicular helper) between responders and non-responders across treatment.

Due to pembrolizumab targeting the PD-1 receptor, the frequencies of PD-1$^+$ cells by CD4$^+$ and CD8$^+$ subtype at C1 were evaluated and found that EM cells are the most frequent of PD1$^+$ cells in both CD4$^+$ and CD8$^+$ cells (FIG. 5 panel (a)). With the alternative exhaustion marker, CTLA-4, the frequency of CTLA-4$^+$ cells within the CD4$^+$ EM cells and CD4$^+$ EMRA populations is higher in responders across all time points (FIG. 5 panel (b)). The data showed no difference of CTLA-4$^+$ frequency among CD8$^+$ subtypes; however, PD-1$^+$ CD8$^+$ EM cells were significantly more frequent in responders than non-responders before treatment (FIG. 5 panel (c)). FIG. 5 panels (a), (b), (c), and (e) show box plots representing the interquartile range (IQR), with the horizontal line indicating the median. Whiskers extend to the farthest data point within a maximum of 1.5×IQR. Because exhausted markers are also associated with a past or present activated function, patients with activated/exhausted T cell function (i.e., against cancer cells) are more likely to respond to therapy [See for example Refs. 38, 39].

Across all treatment time points, PD-1 expression in CD8 and CD4 T cells differs between responders and non-responders. In both groups, PD-1$^+$ CD8$^+$ and PD-1$^+$ CD8$^+$ EM cell frequencies significantly decrease upon commencement of PD-1i therapy. CD4$^+$ and CD4$^+$EM cell frequencies show a significant decrease only in the non-responder patients after the start of PD-1i ($p<0.05$) (FIG. 5 panel (d)). This decrease of PD-1 levels by FACS may be explained by the internalization of the receptor after binding pembrolizumab, suggesting that PD-1$^+$ CD8$^+$ T cells, CD4$^+$, and especially CD4$^+$EM cells of non-responders are targeted by the drug. CD4$^+$ EM cells express PD-1 and are found at a higher frequency in non-responders, suggesting that these cells may act as a collateral target of pembrolizumab. In addition, the frequency of PD-1$^+$ T follicular helper cells ($T_{FH}$), a population that highly expresses PD-1 [See for example Ref. 40], was higher in non-responders than responders at C1, suggesting that these cells could also, in a minority way due to their abundance compared to the CD4$^+$EM, bind pembrolizumab reducing its availability to other cells (FIG. 5 panel (e)). In FIG. 5 panels (d), (e) the vertical bars indicate s. d. The statistical significance is displayed as *$P<0.05$, $P<0.01$ and *$P<0.001$ (two-tailed unpaired t-test).

Finally, at baseline, scRNAseq shows responder T cells express more genes associated with programmed cell death, including PMAIP1, SOCS3, BTG1 and several caspases (FIGS. 16, 17A-C). These genes may signal hallmarks of an exhausted immune cell status. A category of pathways including all death related genes was created and data showed that responders show higher expression of these pathways than non-responders throughout treatment (FIG. 16). Combined with flow cytometry results, the data supported a conclusion that the exhausted status of circulating CD8$^+$ and CD4$^+$ T cells may be a useful criterion in assessing patient response to PD-1i.

Monocytes of Responders are Activated After the Start of PD-1i and Frequency of Classical Monocytes Predict Response.

Figure 6:
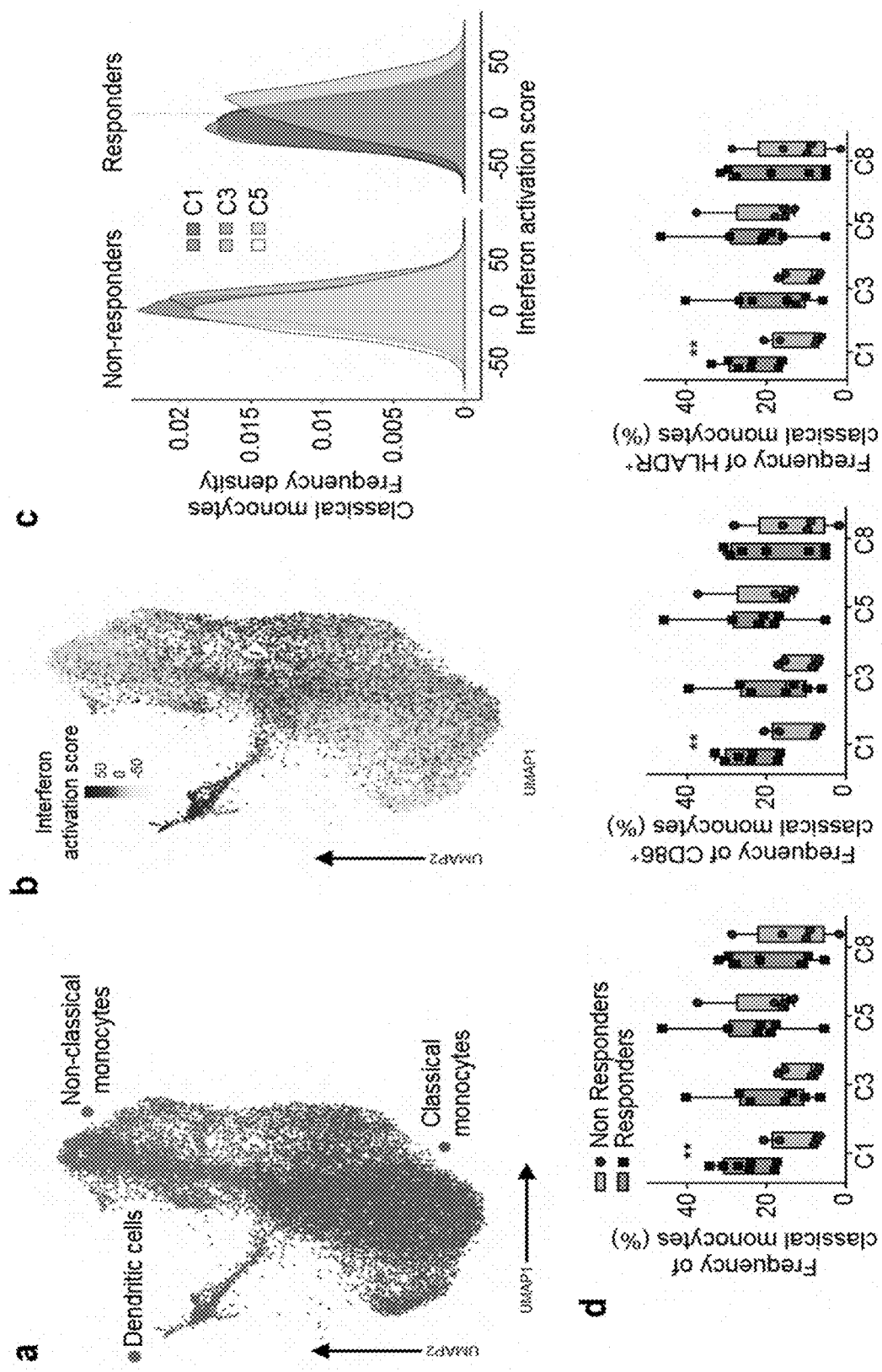
FIG. 6 illustrates that the evolution of classical monocytes in responders from baseline to the start of immunotherapy can represent different activated states. Panel (a) is a Uniform Manifold Approximation and Projection (UMAP) identification of classical and non-classical monocytes and dendritic cells. Panel (b) is a UMAP representing a gradient of interferon activation states (lowest scores situated at the top- and bottom-left and the highest scores at the center right and in dendritic cells). Panel (c) is a graph showing frequency density of monocytes with different interferon (IFN) activation states of responders and non-responders at each treatment time point. Panel (d) are graphs showing a comparison of the frequency of classical monocytes (CD14$^+$/CD16$^-$), CD86$^+$ classical monocytes and HLADR$^+$ classical monocytes of responders and non-responders at different treatment time points as analyzed by flow cytometry is plotted over C1, C3, C5, and C8. The statistical significance is displayed as **P<0.01 (two-tailed unpaired t-test). Box plots represent the interquartile range (IQR), with the horizontal line indicating the median. Whiskers extend to the farthest data point within a maximum of 1.5×IQR.

The major axes of phenotypic variation in monocytes were associated with the distinction among classical monocytes (CD14), non-classical monocytes (FCGR3A=CD16), and dendritic cells (FCER1A) (FIG. 6 panel (a)), as well as the interferon response genes (FIG. 6 panel (b)). Indeed, within both monocyte groups, the expression of interferon response genes was the major axis of monocyte subtype phenotypic variation. Cells with high interferon activation scores had higher expression of genes directly upregulated by IFN stimulation (e.g. IFIT1/3, IFITM3, IFI44L, PSME2, IFI6, ISG15) and MHCII production (e.g. HLA.DPA1, HLA.DPB1, and HLA.DMA). The monocyte interferon activation score was highest in the dendritic cells (FIG. 6 panels (a)-(b)). Cells with lowest scores had increased expression of genes related to proliferation (e.g. FOS, FOSB, and JUN), differentiation (e.g. BTG1, RGS2, and DDX17), inflammation e.g. SELL, S100A12, and CD36) and migration (e.g. VCAN, MALAT1, VIM, and ZEB2).

Figure 21:
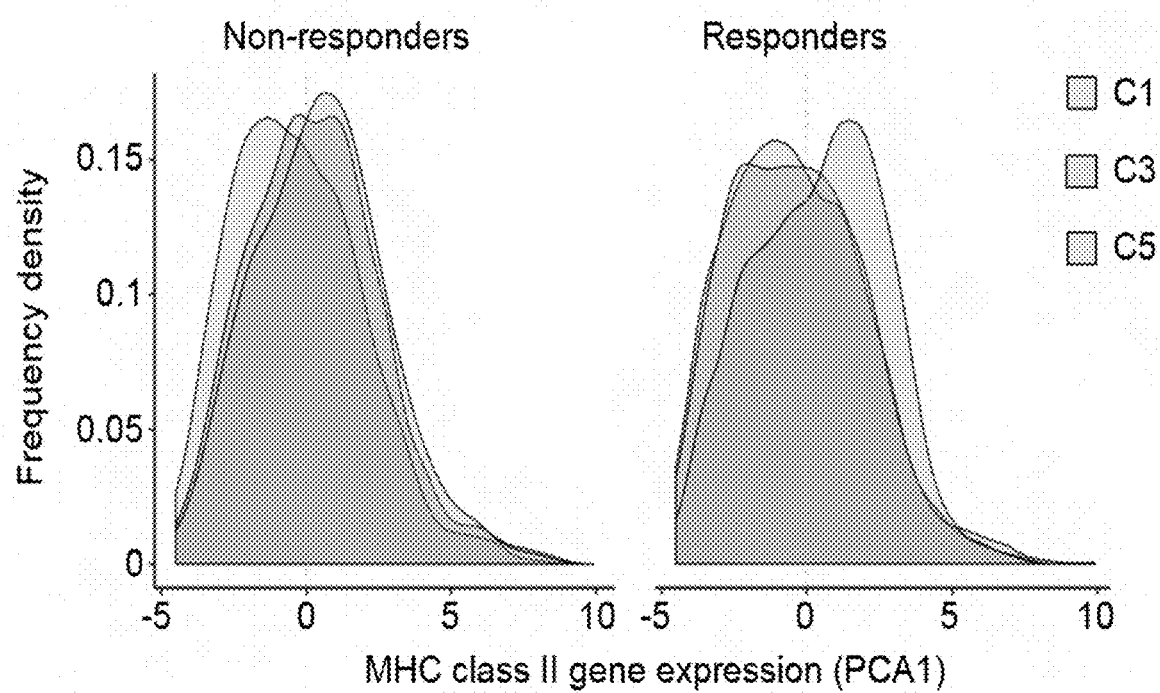
FIG. 21 is a graph showing that Major Histocompatibility Complex (MHC) II gene expression of monocytes increases more in responders than non-responders following PD-li immunotherapy. Frequency of monocytes with different levels of MHC II gene expression compared between responders and non-responders at each treatment time point (C1, C3, and C5, where C stands for cycle, 1 cycle is 14 days, C1 is the baseline, C3 is the chemotherapy FOLFOX regimen, C5 is the chemotherapy+anti PD-1 immunotherapy regimen). The overall MHC II expression score was produced using the first dimension of a principle component analysis applied to the expression of all HLA class II alpha chain genes within each cell.

Cells with the highest interferon activation score were prevalent in responder patients after the onset of the PD-1i (FIG. 6 panel (b), FIG. 11B). The distribution of interferon activation in non-responder monocytes of remained relatively constant between time points C1, C3, and C5. In contrast, responder monocytes showed a significant activation shift after the addition of PD-1i (C5) ($t=15.463$, $p<0.001$) (FIG. 6 panel (c)). The phenotype distribution of monocytes in responders shifted from having the lowest to the highest average level of interferon activation and MHC II gene expression (FIG. 21).

Next, the frequency of classical monocytes (CD14$^+$/CD16$^-$) was analyzed by flow cytometry, a measure shown to be useful for predicting response to PD-1i in melanoma cancer [See for example Ref 28]. At C1, responders had a higher frequency of classical monocytes, a difference abolished by the start of chemotherapy treatment (FIG. 6 panel (d)). Contrary to the findings from scRNAseq analysis, data showed that responders have more CD86$^+$ and HLADR$^+$ classical monocytes than non-responders (FIG. 6 panel (d)). Indeed, scRNAseq showed a higher density of classical monocytes and a slightly higher upregulation of MHC II genes in non-responders at baseline. The data suggests MHC II gene expression and protein expression are inversely correlated.

Figure 7:
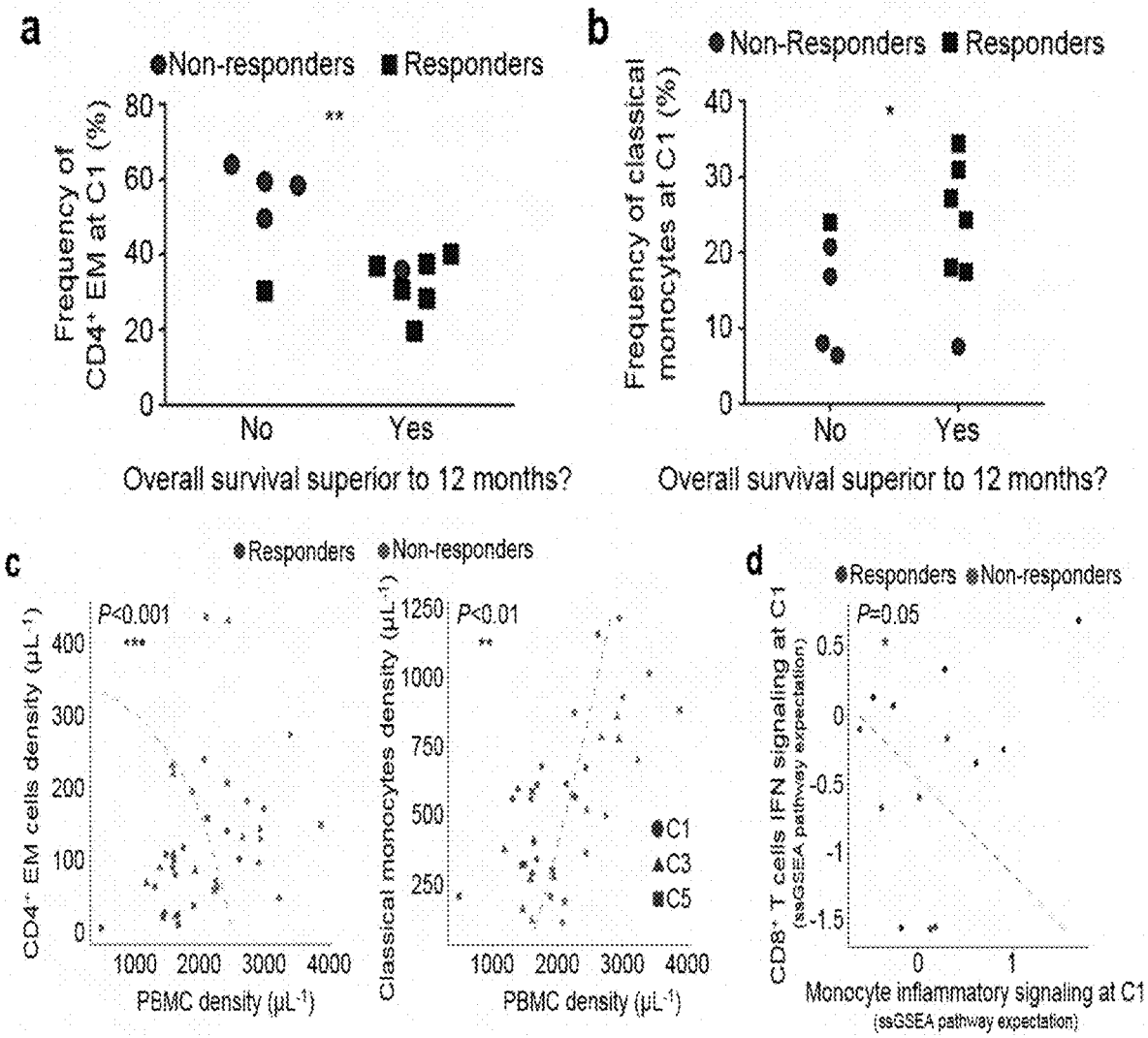
FIG. 7 are plots showing that density and signaling states of CD4$^+$ EM cells and monocytes are predictive markers of response to therapy. Panel (a) is a graph showing the relationship between CD4$^+$ EM frequency observed by flow cytometry and the overall survival at 12 months in non-responders and responders. Panel (b) is a graph showing the relationship between classical monocyte frequency observed by flow cytometry and the overall survival at 12 months in non-responders and responders. "No" indicates patients with survival less than 12 months while "Yes" indicates patients with survival greater than 12 months. In Panels (a)-(b), statistical significance is displayed as *P<0.05 and **P<0.01 (two-tailed unpaired t-test), and C stands for cycle, 1 cycle is 14 days, C1 is the baseline, C3 is the chemotherapy mFOLOFX6 regimen, and C5 is the Chemotherapy+anti PD-1 immunotherapy regimen. Panel (c) are graphs showing the response of GI cancer patients to PD-1 inhibitor immunotherapy (point color) depends on PMBC density at the early stages of treatment (C1-C5), as well as CD4$^+$ EM (Effector memory) T cells and classical monocyte density. Patient response boundaries (dashed lines) were predicted using a hierarchical logistic regression model and delineate responsive and non-responsive immune states. Panel (d) is a graph of the pretreatment patient averaged GSEA pathway scores for CD8+ T cell interferon (IFN) activation and monocyte inflammatory response. The figure shows the correlation of monocytes inflammatory signaling and CD8 IFN signaling and responsiveness to therapy.

Frequencies of CD4$^+$EM and Classical Monocytes are Correlated with Overall Survival The relationship between the frequency of CD4$^+$ EM cells as determined by flow cytometry and the overall survival after 12 months of treatment was analyzed (FIG. 7 panel (a)). Data showed that 7 patients had an overall survival greater than 12 months when their frequency of CD4$^+$EM was below 40% at the C1 time point. Among these 7 patients, 6 were responders and 1 a non-responder. In contrast, 5 patients survived less than 12 months. Four were non-responders and show a frequency of CD4$^+$ EM greater than 40%. Similarly, classical monocyte counts prior to therapy may also serve as a marker of response to immunotherapy (FIG. 7 panel (b)).

In order to test whether immune cell density and signaling states predict response to therapy, random effects logistic regression models were developed. Patients with a lower total PBMC density during the first five cycles of treatment were significantly more likely to respond to PD-1i ($z=-3.01$, $p<0.001$). Incorporating the frequencies of CD4$^+$ T cell and classical monocyte immune sub-classes significantly improved the prediction of patient response (FIG. 7 panel (c)). Patients with a lower CD4$^+$ effector memory density were significantly more likely to respond to PD-1i therapy than would be expected given their PBMC density ($z=-4.03$, $p<0.001$). Patients with a relatively high proportion of classical monocytes were also significantly more likely to respond ($z=2.76$, $p<0.01$). By combining initial PBMC count and immune subclass frequencies, patient responses could be predicted with an overall 85% accuracy (FIG. 7 panel (c)). Differences in pathway activity signatures (GSEA scores) between responders and non-responders at baseline were assessed. Responsive patients had either: a) monocytes exhibiting a high inflammatory response or b) CD8$^+$ T cells with high IFN signaling activation ($z=3.18$, p<0.001) (FIG. 7 panel (d)). These results indicate that patient PD-1i response could be predicted at early stages of therapy based on a low CD4$^+$ EM T cell count and a high fraction of classical monocytes. Importantly, the signaling state of T cells and monocytes may contribute to outcomes.

Discussion

Figure 8:
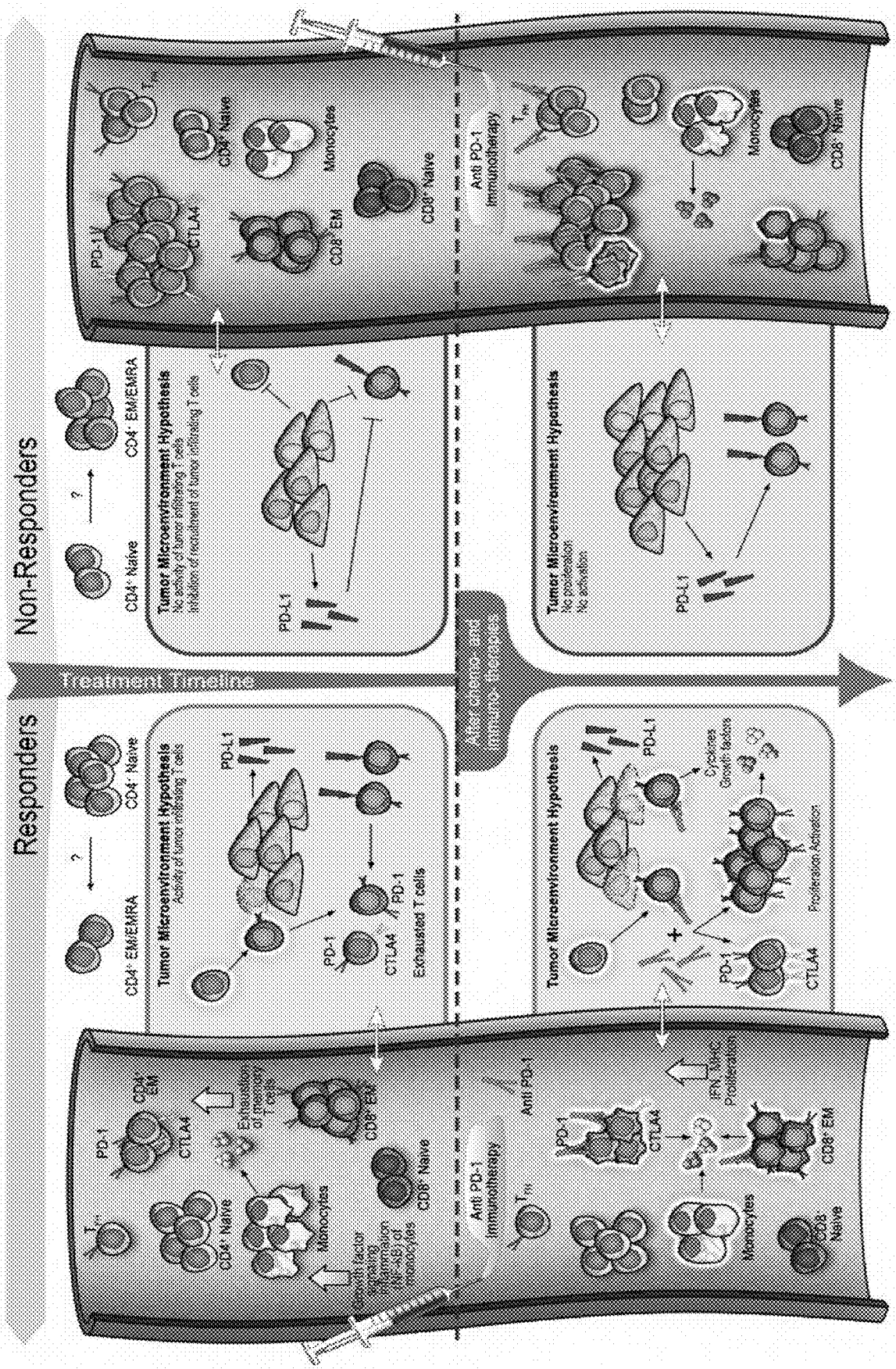
FIG. 8 illustrates a model of the dynamics and evolution of PBMCs in responders and non-responders.
Figures 1, 9A:
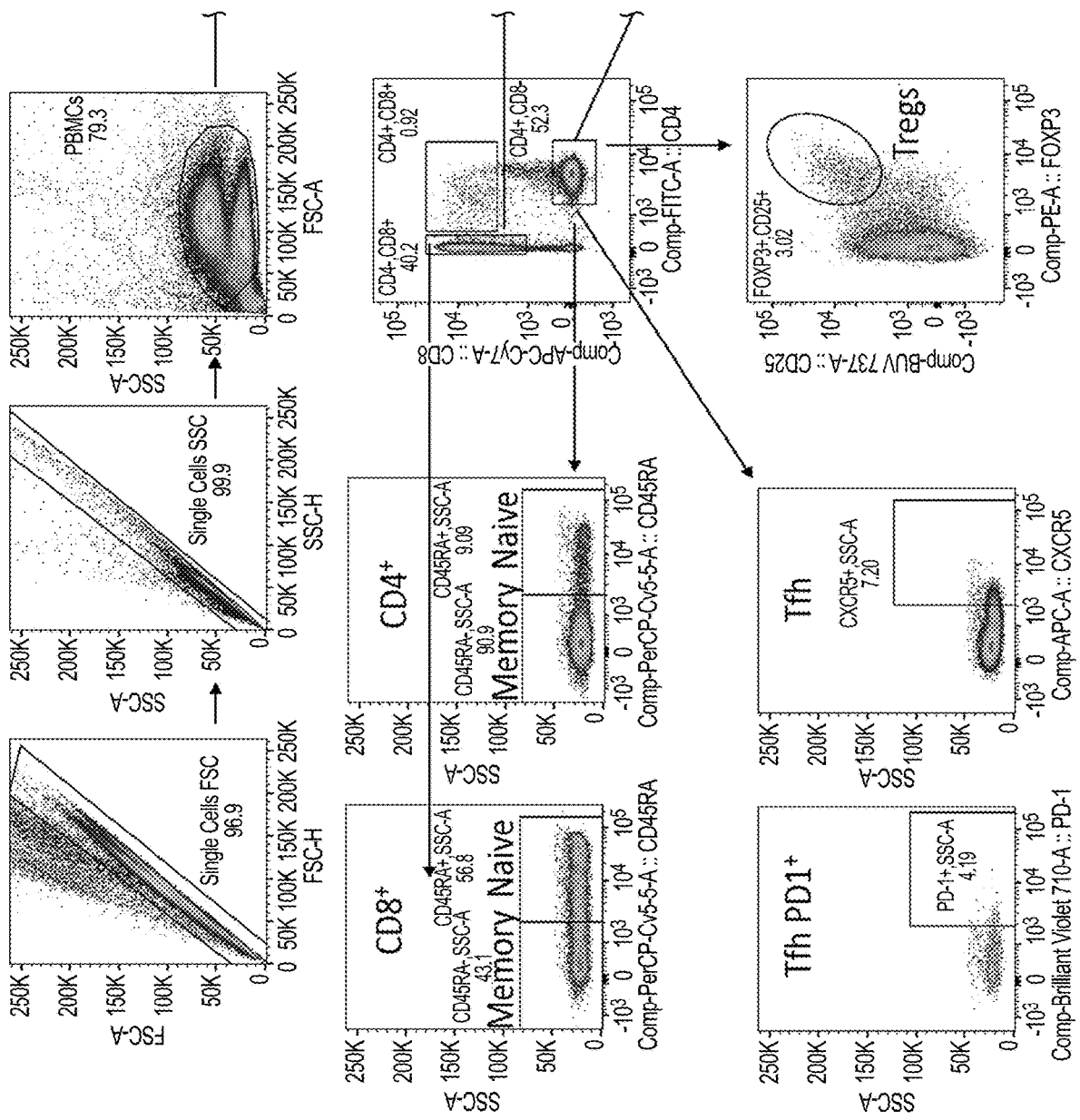
FIGS. 9A-F (including FIGS. 9A-1, 9A-2, 9B, 9C-1, 9C-2, 9D-1, 9D-2, 9E-1, 9E-2, 9F-1, and 9F-2) depict a gating strategy used to analyze PBMCs, including a stepwise division of various cell populations, starting from PBMCs, into smaller and smaller subpopulations of interest based on multiple binning methods. In one example, flow cytometry analysis of PBMCs isolated from 3 to 4 time points, C1, C3, C5, and C8 was performed on a set of responder and non-responder patients. The time points refer to cycle 1 (C1), which is baseline without any treatment, cycle 3 (C3), which is treatment with only mFOLFOX6 chemotherapy, and cycle 5 (C5) or cycle 8 (C8), which are two different time points during treatment with both mFOLFOX6 and PD-1i immunotherapy. A total of 12 patients (responder n=7, non-responder n=5) were analyzed by flow cytometry. In another example, flow cytometry analysis using CD45RA and CCR7 as markers was used to discriminate memory from naïve T cells identified multiple significant differences in the CD4 population.
Figures 2, 9A:
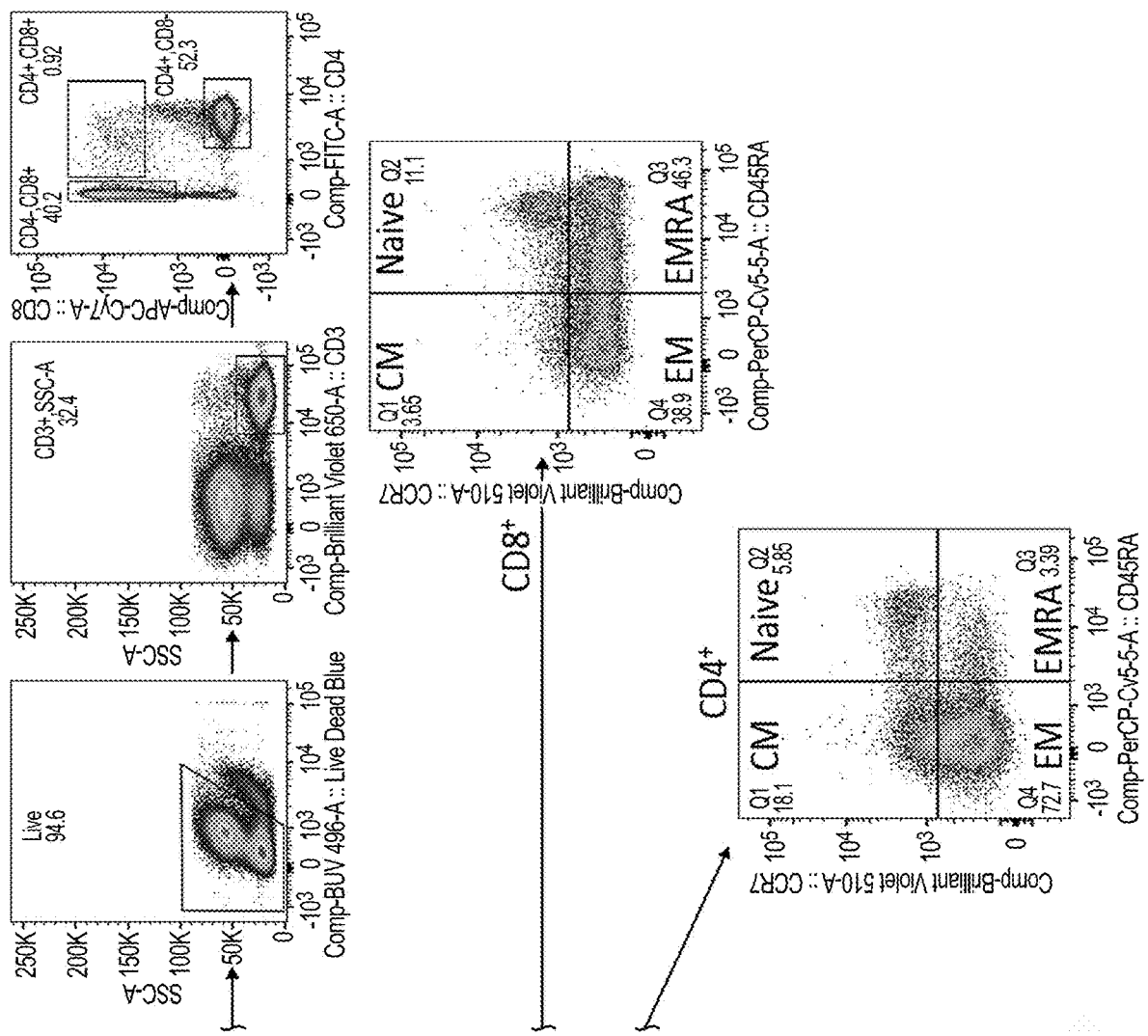
Figure 9B:
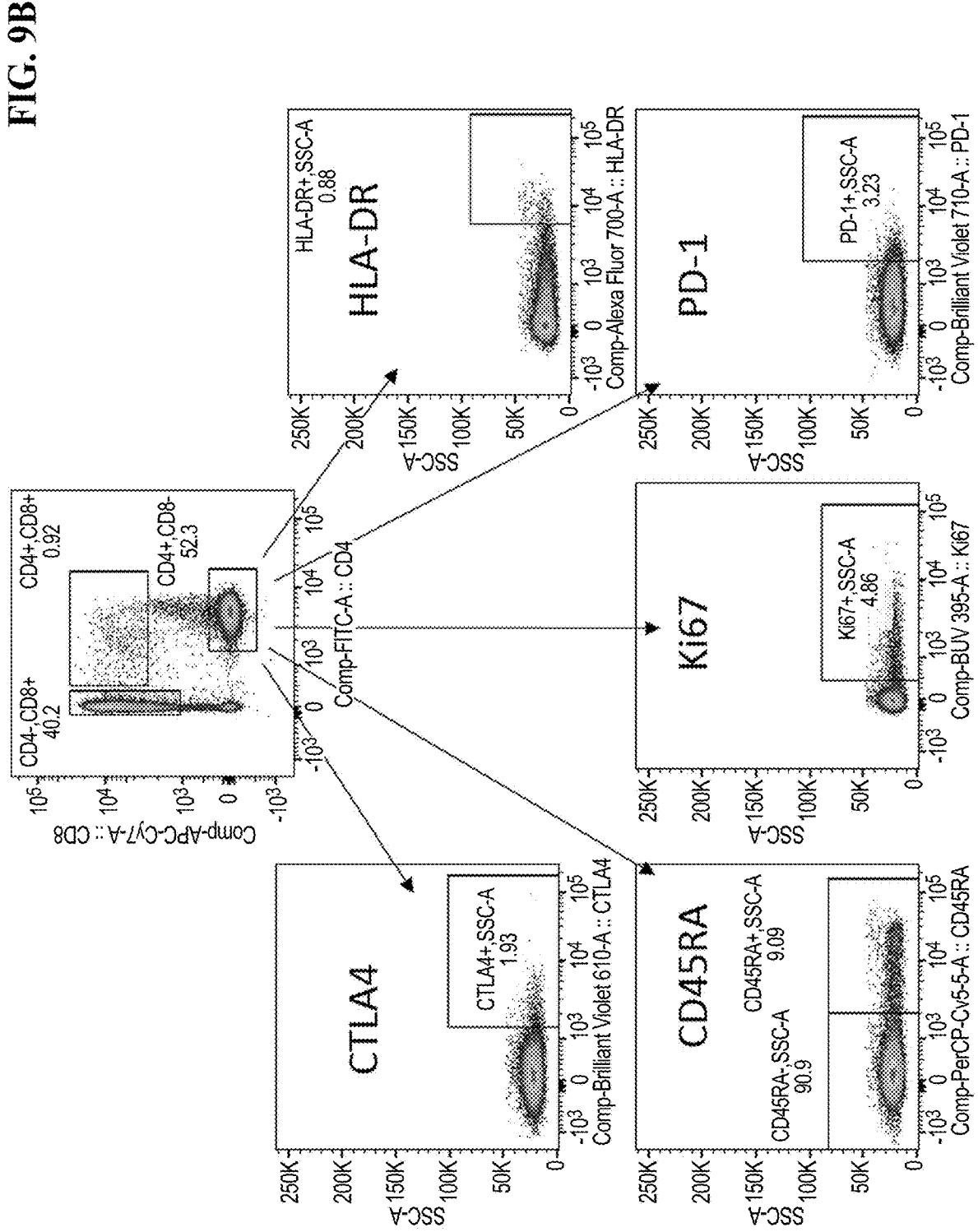
Figure 9C:
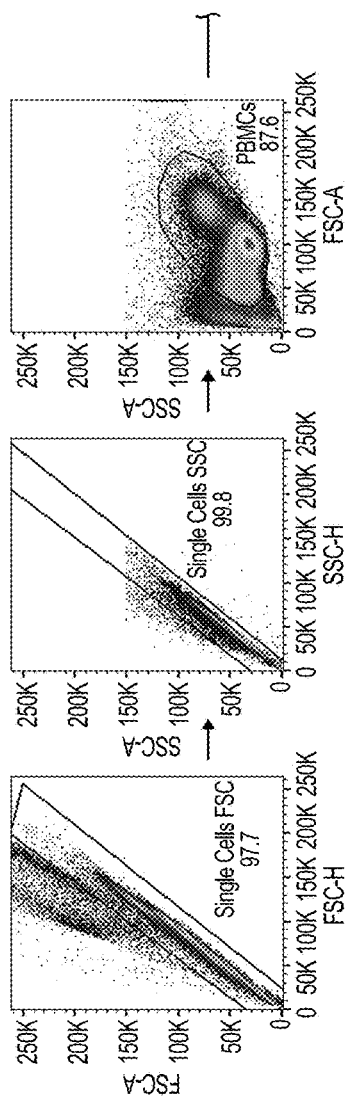
Figure 1:
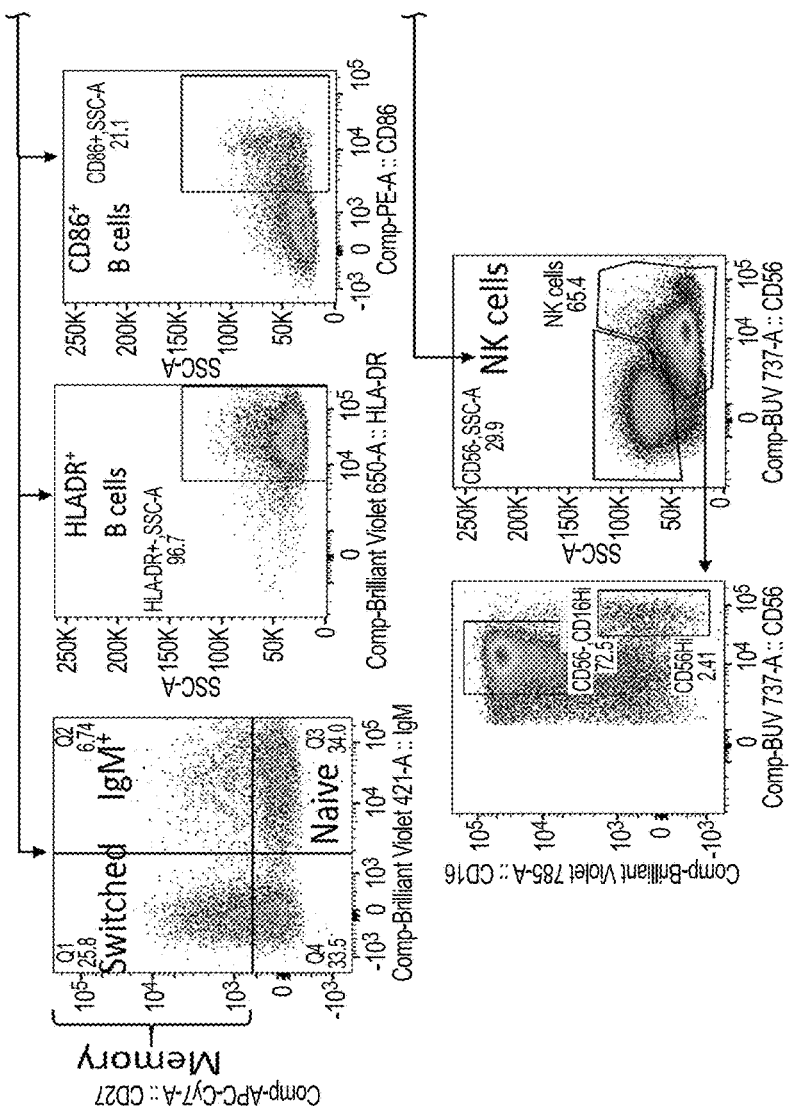
Figures 2, 9C:
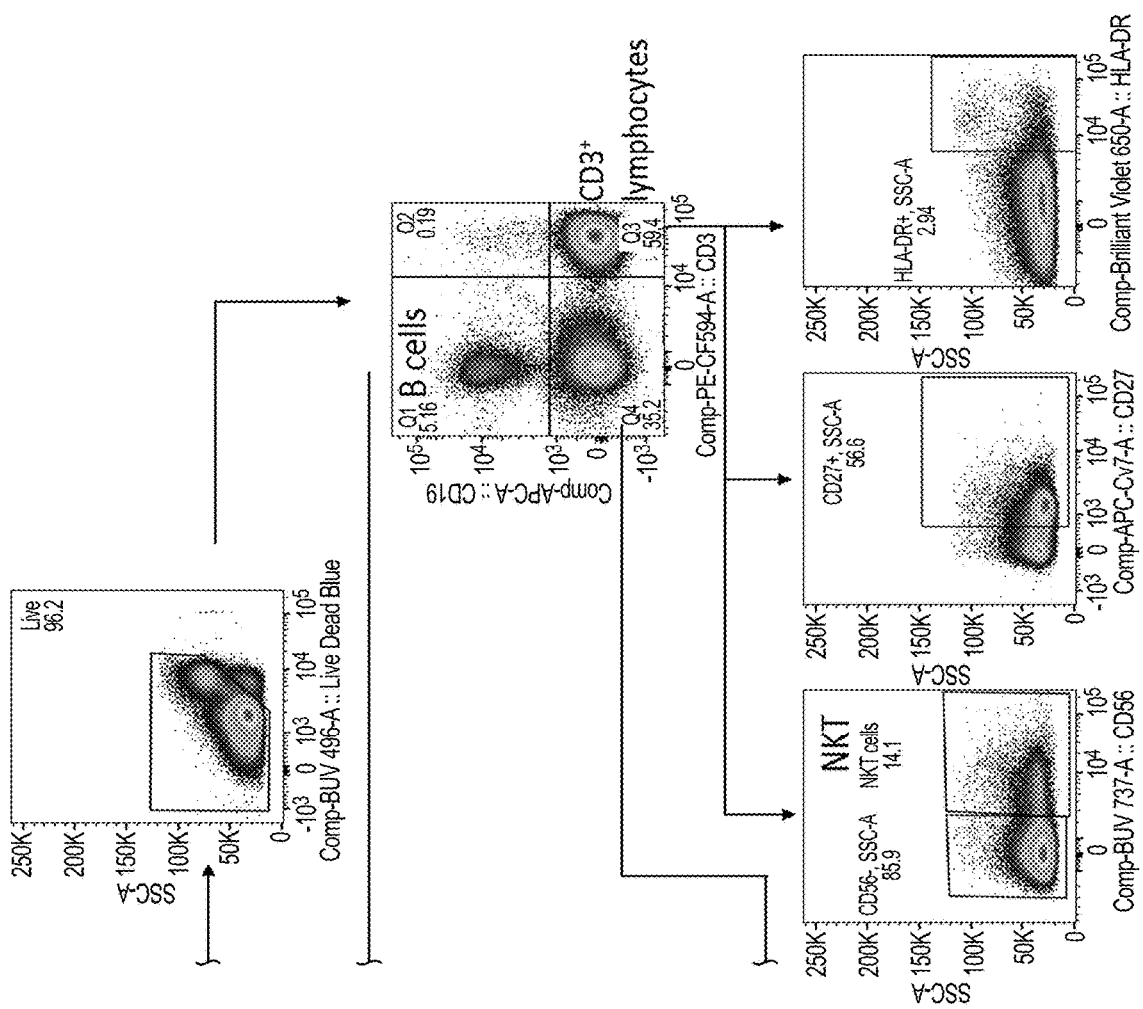
Figures 1, 9D:
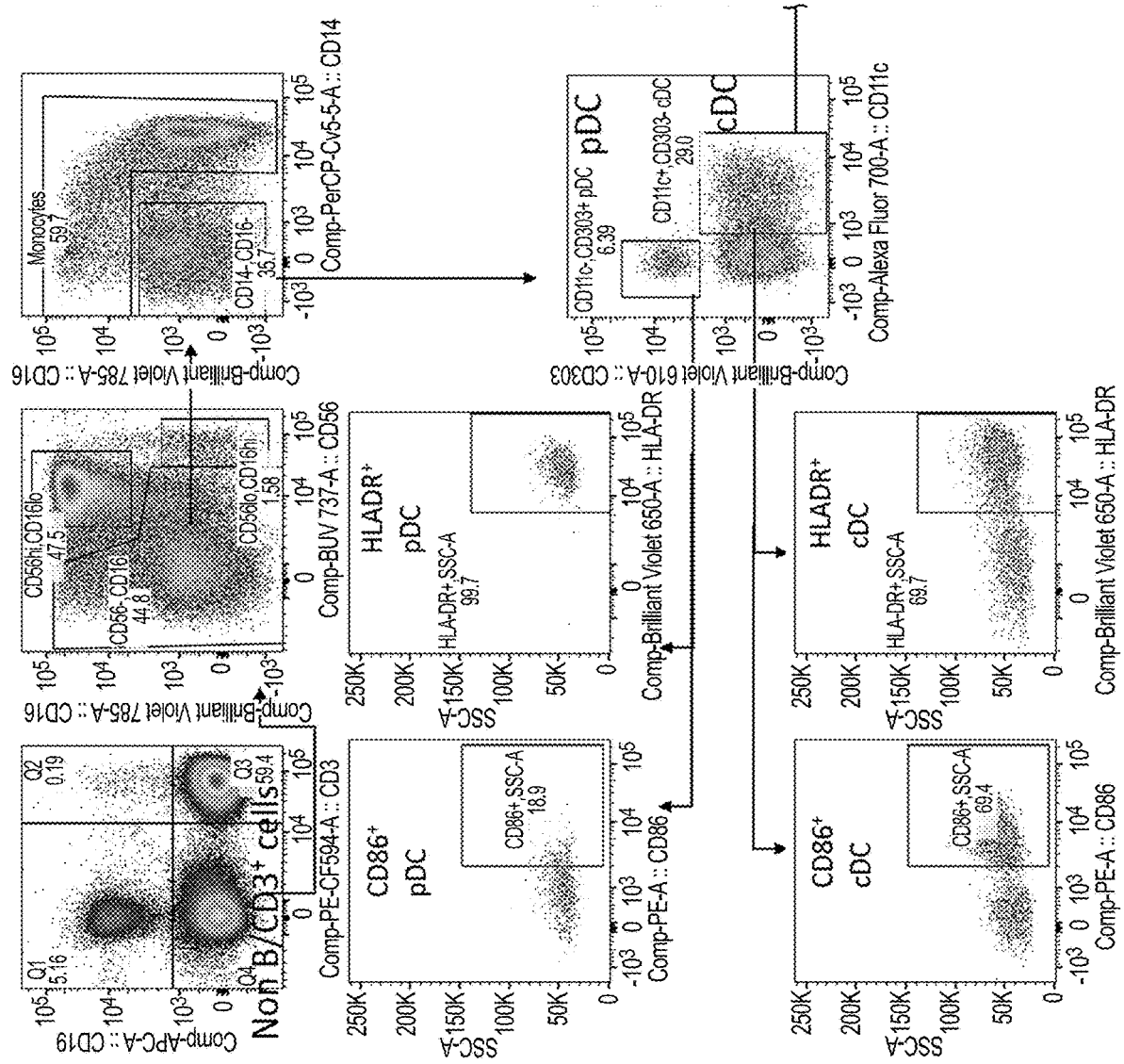
Figures 2, 9D:
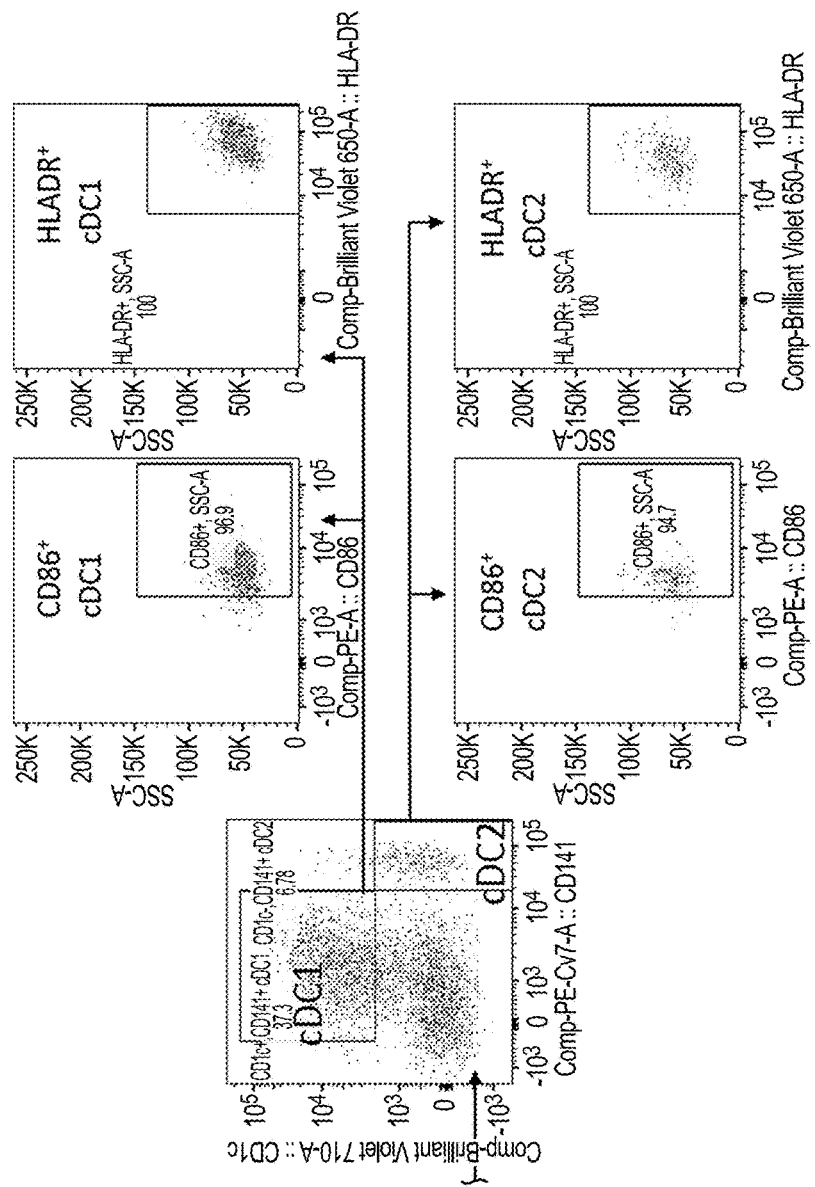
Figures 1, 9E:
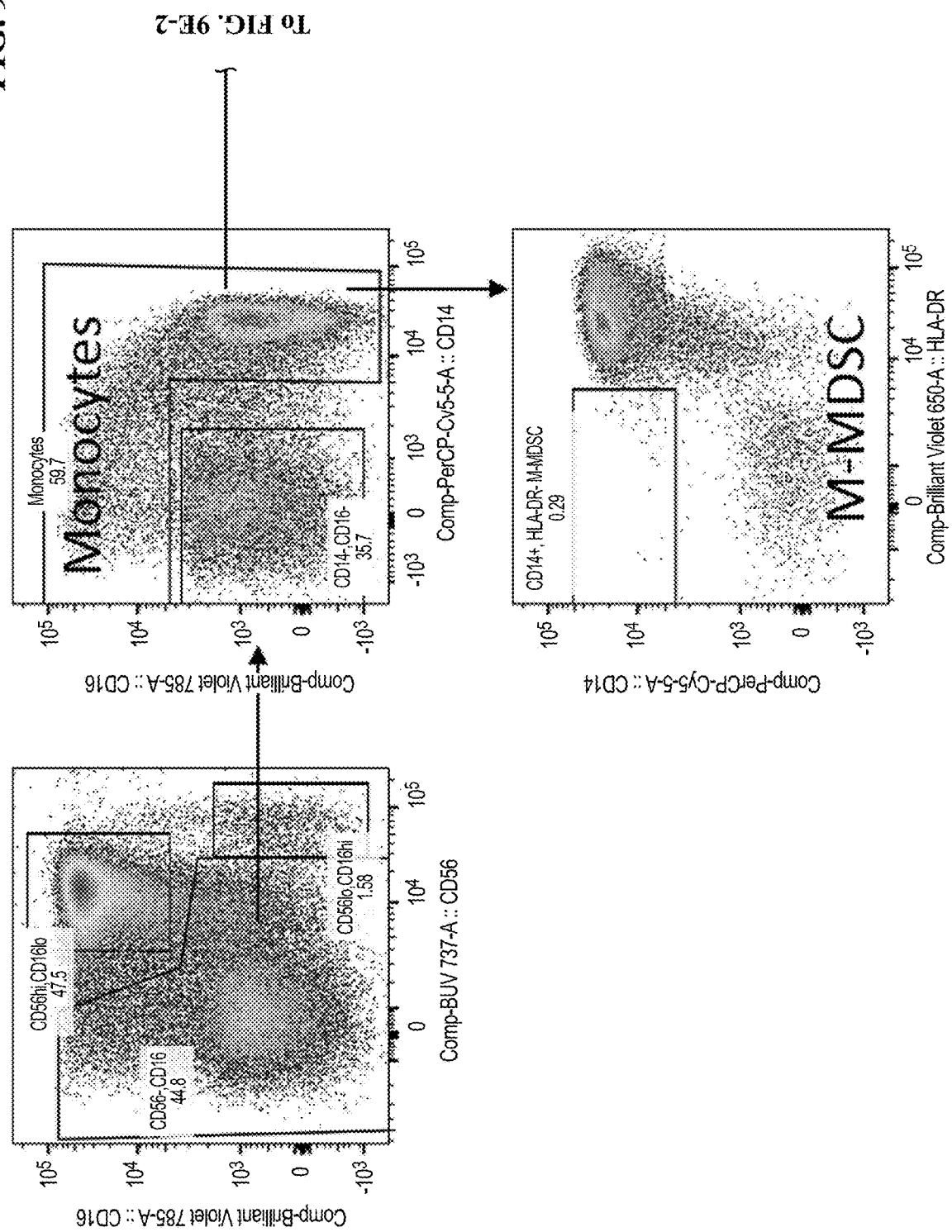
Figure 9F:
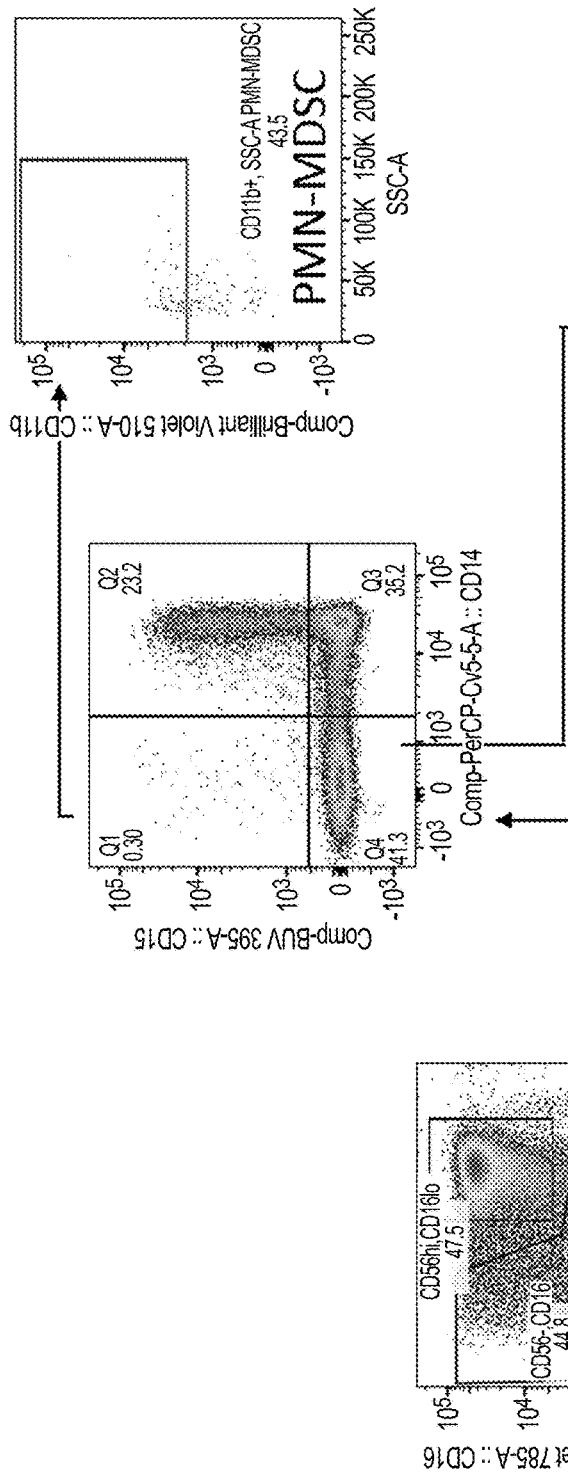
Figure 1:
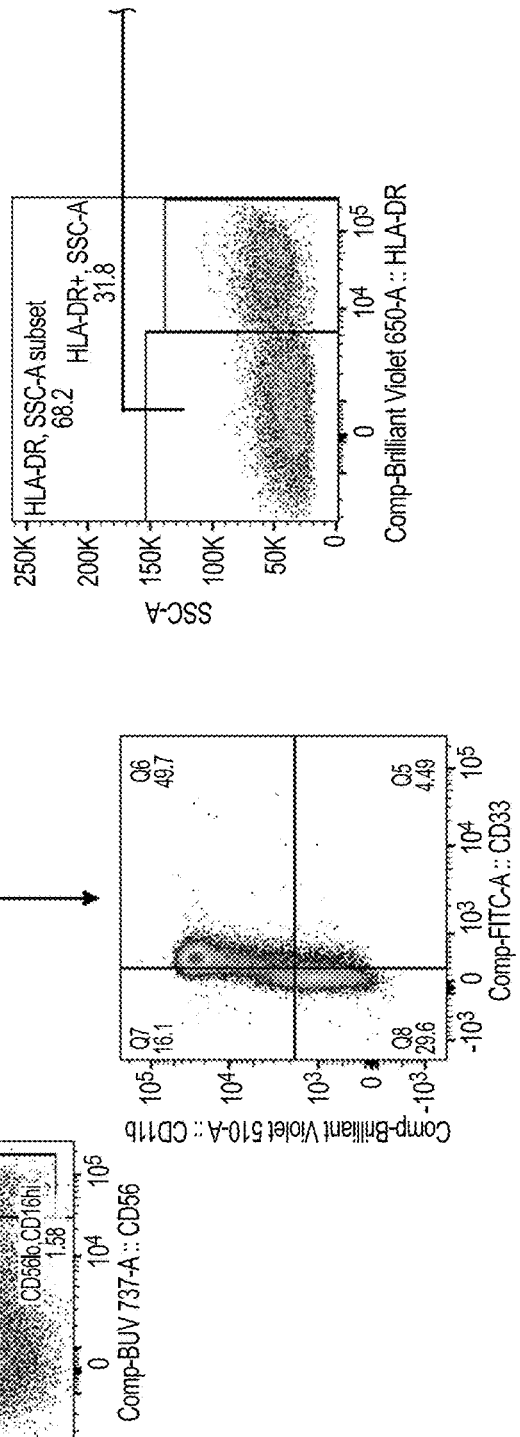
Figures 2, 9F:
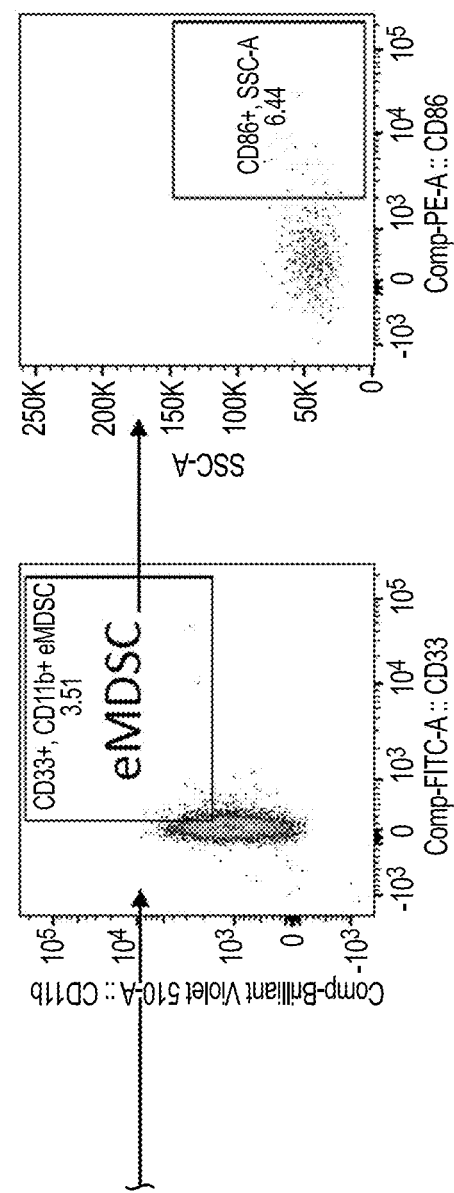

Immune checkpoint inhibitors have great potential and are being increasingly used to treat a variety of cancers; however, only a minor proportion of patients have an objective response [See for example Ref 41]. To understand why some patients respond while others do not, the evolution of immune response to PD-1i using a combined scRNAseq and flow cytometry analysis of PBMCs was assessed. The data show state changes of immune populations during chemotherapy and immunotherapy and provide potential markers of therapy response, including the density of CD4$^+$EM cells and classical monocytes. Moreover, measurements of T cell and monocyte signaling states before and during therapy in relation to patient responsiveness were determined. Based on all observed results, a model of circulating immune cell evolution during the treatment of GI cancer patients is provided (FIG. 8), where treatment with PD-1i leads to activation of PD1-expressing exhausted T-cells, resulting in antitumor activity, cytokine release, and stimulation of the immune system. Before treatment, responders have more circulating CD4$^+$ naïve cells, fewer CD4$^+$ EM (Effector memory) cells and more CTLA4$^+$ EM cells, more PD-1$^+$ CD8$^+$ EM cells, fewer $T_{FH}$, and more activated classical monocytes than non-responders. The exhausted state of responders' immune cells supports the hypothesis that T cells of responders were activated before treatment, possibly with tumor specificity, followed by exhaustion induced by cancer or stromal cells. In addition, responder monocytes have higher frequency than non-responders and upregulated TNF-α, NF-KB and growth factor pathways. An explanation for this behavior is that responder monocytes can have an immune suppressive function. Further, non-responders have low levels of exhausted cells and a large population of circulating differentiated cells (CD4$^+$ EM). Also, in non-responders, an explanation for this behavior includes cancer cells directly or indirectly inhibiting the recruitment of tumor infiltrating cells and/or the function of cytotoxic immune cells. After chemotherapy and immunotherapy, T cells and monocytes of responders upregulate activation pathways including interferon signaling and MHC processing. The continuing excess of CTLA4$^+$ CD4$^+$ EM cells in responders and lack of a difference in PD-1$^+$ CD8$^+$ EM cells imply that PD-1i is protecting T cells leading to their activation along with recruitment and subsequent activation of other cancer-killing immune cells. In non-responders, CD4$^+$ EM and $T_{FH}$ (Follicular helper) are high in frequency and express PD-1, and may act as a decoy for the PD-1i before it reaches cytotoxic CD8$^+$ T cells. Finally, non-responder monocytes upregulated NF-KB and TNF-α pathways after the start of PD-1i. An explanation for this behavior includes non-responder monocytes having an immune suppressive function similar to responder monocytes before treatment.

In particular, before treatment, responders exhibit a high abundance of exhausted PD1$^+$ T-cells and classical monocytes show increased growth and inflammation signaling. This exhausted state may reflect prior tumor recognition, for example upon chemotherapy treatment and neoantigen presentation. No other immune cell populations show these signatures prior to immune therapy initiation. Following PD-1i treatment, monocytes change states that may reflect cancer cell recognition and immune cell activation. Further, memory T cell abundances in immunotherapy-responsive patients evolves and increases, with concurrent upregulation in IFN signaling. Overall, both abundance and frequency of CD4$^+$EM and classical monocytes, as well as their signaling states, are associated with improved survival.

After the start of PD-1i, the data showed that IFN signaling is highly upregulated in T cells and monocytes of responders. In particular, CD8$^+$T cells upregulate IFN-γ gene expression, a major cytokine associated with an overall activation of immune cells and to an anti-tumor effect [See for example Ref. 42]. However, the CD8$^+$ T cells and monocytes of non-responders do not have a clear upregulation of the IFN signaling, indicating that these cells are not fully activated. This lack of IFN activation in circulating immune cells in non-responders may indicate these cells are not able to detect the cancer cells even with the help of PD-1i.

Another potential mechanism of non-responsiveness to immunotherapy may be an imbalance of T cell subtype abundances. If chemotherapy response and subsequent cancer cell death releases antigen and promotion of T cell exhaustion, resistance to chemotherapy could be one mechanism explaining why non-responders have a low relative abundance of exhausted T cells. PD-1$^+$ and CTLA4$^+$ cells are commonly categorized as exhausted which also means that they potentially were or are activated against cancer cells [See for example Refs. 38 and 39]. The data demonstrated increased circulating PD-1$^+$CD8$^+$EM and CTLA4$^+$ CD4$^+$EM (exhausted) T cells in responders at baseline and after a month of mFOLFOX6 therapy. In agreement, NSCLC patients with clinical benefit to immunotherapy also exhibited circulating PD-1$^+$CD8$^+$ T-cell with effector-like phenotype [See for example Ref. 44]. The low frequency of PD1$^+$ CD8$^+$ cells in non-responders before the start of PD-1i imply less potential PD-1 immunotherapy-targeted cells. Indeed, a recent study demonstrated that FOLFOX induces durable complete responses when combined with anti-PD-1 therapy in mouse colorectal cancer models [See for example Ref 43], in part due to recruitment of exhausted PD-1$^+$CD8$^+$ cells to the tumor. The data herein supports circulating exhausted T cells may reflect the presence of activated intra-tumoral T cells and therefore be a marker of immunotherapy response.

An alternative possibility of non-response is that the PD-1 antibody availability to cytotoxic CD8$^+$ is reduced in non-responders. For example, CD4$^+$EM express PD-1 and have high relative abundance in non-responders at baseline. A high frequency of CD4$^+$EM was also correlated with shorter PFS in NSCLC [See for example Ref. 45]. Some studies reveal that chemotherapy induces the proliferation of differentiated CD4$^+$memory or EM cells in breast cancer or chronic lymphocytic leukemia patients [See for example Refs. 46-48]. Those studies found that PD-1 is highly expressed in those memory CD4$^+$ cells [See for example Refs. 46, 48]. In the cohort studied herein, all non-responders had prior treatment and 70% had prior 5-FU/Oxaliplatin whereas only 25% of responders had prior treatment and 88% did not have prior 5-FU/Oxaliplatin and had, at baseline, more CD4$^+$EM which expressing PD-1 compare to responders. The data suggests that long term chemotherapy increases the production of CD4$^+$EM cells expressing PD-1 which could potentially diminish availability of pembrolizumab to tumor-specific CD8$^+$ T cells through binding in the peripheral blood. Additionally, protected by anti-PD-1 therapy, CD4$^+$EM cells could actively secrete immune suppressive cytokines after activation. It does not appear as though any mechanistic research regarding CD4$^+$EM cells under PD-1i treatment has been conducted but a high frequency of those cells were also found in melanoma patients non-responsive to anti-PD-1 therapy [See for example Ref. 28].

Additional mechanisms include the possibility that non-responder cancer cells may have developed PD-1/PD-L1 independent avoidance of the immune system such as down regulation of MHC presentation, and that non-responders present less circulating naïve CD4$^+$T cells and lower tumor-dependent activation and differentiation of these cells in response to antigen-presenting cells.

At baseline, the data demonstrated increased classical monocytes (CD14$^+$/CD16$^-$) in responders, which correlated with longer survival. These results parallel findings in melanomas responsive to PD-1i [See for example Ref 28]. There were striking differences in signaling states of monocytes before and during PD-1i treatment. At baseline, responder monocytes inhibit the NF-κB pathway, upregulate TNF-induced gene expression, and express genes related to migration and recruitment of immune cells. The data showed that classical monocytes express more MHC class II receptor, HLADR, reflecting a potential antigen presentation function. These cells also express more CD86, which is a ligand of both CTLA-4, a protein associated with immunosuppressive function, and CD28, a costimulatory signal for activation of T cells. These results, taken along with the increased frequency of exhausted T cells, suggest that at baseline, monocytes of responders may have an immune suppressive function. However, after the start of PD-li, responder monocytes upregulate expression of ISGs and MHC related genes showing an overall activation of these cells with potentially a costimulatory immune function. This phenotype could be the consequence of T cells high upregulation of IFN gene expression we have detected after the start of PD-li. IFN could be used as a biomarker of early response to PD-1i and clearance of cancer. However, long-term exposure to IFN-γ is not necessarily beneficial to patients [See for example Ref 42]. In this trial, most responders eventually developed resistance to treatment by cycle 9, (median PFS of responders was 8 months, data not shown). Relapses could be explained by cancer cells capacity to take advantage of IFN signaling to develop new resistance mechanisms [See for example Ref 42].

Rapid and readily accessible predictive biomarkers can be used to target therapies to responsive patients, reducing adverse events and costs. A PBMC marker provides such access. Overall, the data showed that the density and signaling activity of circulating immune cells is dynamic. Differences in immune cells between patients that respond and do not respond to PD-li are present prior to and following treatment, and reflect unique activation and differentiation states related to drug response. The fact that cell densities and signaling states of circulating classical monocytes and CD4$^+$EM cells are correlated with better overall survival in melanoma and GI cancers, demonstrates the possibility of using blood-based biomarkers for predicting PD-1i response across multiple cancer types in which this treatment has been approved.

Example 2

Materials and Methods

Patient Samples

Cryopreserved peripheral blood mononuclear cells (PBMC) samples from patients with advanced (stage 3/4) gastrointestinal cancers (including colorectal, gastroesophageal, pancreatic and biliary cancers) were provided by the Huntsman Cancer Institute, University of Utah, Salt Lake City, Utah, USA. Patients in this trial (NCT02268825), were treated with modified FOLFOX6 (mFOLOFX6) chemotherapy regimen consisting of 400 mg/m$^2$ intravenous (IV) leucovorin, 400 mg/m$^2$ IV fluorouracil (5-FU) bolus followed by 2400 mg/m$^2$ IV over 46 hrs and 85 mg/m$^2$ IV oxaliplatin (Eloxatin) every 2 weeks (i.e. 1 cycle) until disease progression, death, or completion of the study. Pembrolizumab 200 mg IV every two weeks was added to mFOLFOX6 at cycle 3, after 4 weeks of mFOLFOX. Every two weeks, and before starting treatment, patients' blood was collected and PBMCs were isolated and cryopreserved. Median of previous history of chemotherapy treatment for responders was 101 days and 42 days for non-responders (Table 1). Clinical response and disease assessment were measured by computed tomography scans and assessed according to RECIST1.1 and immune-related response criteria (irRC) every 12 weeks. The responders were classified as any patient with clinical benefit at 24 weeks after the start of the trial; this group includes patients with complete response (CR), partial response (PR) and stable disease (SD). The non-responder group includes patients with progressive disease (PD) at least 12 weeks after the start of the trial and maximum 24 weeks after the start of the trial. Progressive disease was defined by an increase in the tumor volume of at least 20% or appearance of new metastatic lesions. All human biological samples were collected after written informed consent of the patients was obtained and with approval of the local ethics committee in accordance to federal and institutional guidelines. Samples from 12 patients were used for flow cytometry immunophenotyping at cycle 1 (C1), C3, C5, C8 time points (period since prior chemotherapy). Samples from 13 patients were used for single cell (SC) RNA analysis at C1, C3 and C5 time points. Samples from eight patients were utilized for both FACS and SC RNA analysis.

Single-Cell RNA Sample Preparation and Sequencing Analysis

PBMC samples were thawed at 37° C. and washed with PBS followed by 0.04% non-acetylated BSA in PBS. Samples were diluted to 1000 cells/μL and suspensions were loaded on a Chromium 10× Cell Instrument (10× Genomics). Approximately 1200 to 2000 cells were loaded per sample. Single-cell RNA sequencing libraries were prepared using the Chromium Single Cell 3' Library & Gel Bead Kit V2 protocol (10× Genomics). Libraries were sequenced on an Illumina HiSeq 2500 with 2×125 paired-end reads. Raw BCL sequencing files were processed by the Cell Ranger Single Cell Software Suite for demultiplexing, barcode assignment, alignment and UMI counting (support. 10×genomics.com/single-cell-gene-expression/software/overview/welcome). Samples were aligned to hg19 using the STAR aligner [See for example Ref. 49]. Count tables were generated with a total of 71,545 cells and used as input into Seurat v2 [See for example Ref 50]. We filtered out cells with fewer than 400 genes and high mitochondrial expression (cells with >10% of mitochondrial counts), resulting in 69,745 cells and 19,324 genes. Counts from remaining cells were log-transformed and normalized across samples. Two regressions were performed on the data set, the first to remove sequencing lane artifacts and the second to further reduce mitochondrial heterogeneity. No notable batch effects were found (FIGS. 11B-D).

The top 1000 variable genes with 1480 non-overlapping known immune cell marker genes were used for PCA [See for example Refs. 51-53]. The data showed the first 25 PCs to be significant using Seurat's jackstraw analysis, which was then used for graph-based clustering and UMAP visualization [See for example Ref. 54]. To gain a better understanding of T cell subpopulations, initial T cell clusters were identified by CD3D, CD4 and CD8 expression and re-clustered. The same number of PCs were used for clustering along with 500 T cell specific variable genes and 273 known T cell markers [See for example Ref.53]. Differential expression markers for each cluster were generated using the MAST [See for example Ref. 55].

Pathway enrichment scores were generated using the R package GSVA 1.30.0 [See for example Ref. 32]. The GSVA ssGSEA option was used to generate scores for all molecular Signatures Database C2 and Hallmark pathway signatures (version 5).

Comparing Cluster Annotations in PD-1 Dataset with Public Data Sets

Two methods were used to compare immune cell annotation in our study and in two public datasets [See for example Refs. 29,30]. First, the dataset herein was used to train classification learners and used the trained learners to predict immune cells from public data sets. The cluster labels annotated in public data sets were used as ground truth. The similarity of annotations was measured by the accuracy of prediction. Second, the similarity of annotation was measured by the number of shared markers between this study and public data sets. To match the clusters in two datasets, only clusters containing at least 10 cells in public data sets were used.

Machine Learning Method

PD-1 scRNAseq samples (N=69745) were used to train and evaluate the classifiers. ScRNAseq raw counts for PBMCs were downloaded from GEO accession GSE114727 [See for example Ref. 30] as a test data set. TPM values for tumor-infiltrating immune cells downloaded from GSE120575 See for example Ref. 29] were used as a second test data set.

In PD-1 dataset, 500 samples were randomly selected from each cluster, except for T6. For clusters with less than 1000 cells, oversampling was performed for 50% of the cells in the cluster. In total, 17,000 cells were used as a training set. The rest of the samples were held out for validation. We repeated this procedure and generated 10 different training and 10 corresponding validation sets.

Seurat was run on the training dataset to obtain the cluster-associated markers See for example Ref. 50]. Only positive markers were selected. For efficiency, only genes that were detected in a minimum fraction of 0.25 in either of the two populations (min.pct=0.25) and whose average expression was larger than 0.25 between clusters were selected (thresh.use=0.25). We ranked the candidate markers using adjusted p-values. The top 20 markers per cluster (410 unique genes) were selected as features in the machine learning process. A multi-class classification using MLR with the RandomForest classifier was performed See for example Ref 56].

Shared Markers Method

The lists of markers was downloaded from Azizi et al. and Sade-Feldman et al. See for example Refs. 29,30]. The markers in Azizi et al. were ranked by z-score and only those with absolute z-score greater than 1.95 were kept. Then, the number of shared marker genes between public data sets and top 20 markers was calculated for each cluster in our study.

Network Visualization

A network structure was used to visualize the similarity and hierarchy of our clusters and the ones in a breast cancer study. The rationale of inferring cluster B belongs to A is that: (1) A and B share a high number of markers. (2) A can pair more clusters than B. The network visualization workflow is shown in FIGS. 13A-C.

Identifying Gene Set Expression Differences Between Responders and Non-Responders Differences in the gene set expression of immune cell types were examined between responder and non-responder patients (R). For each immune cell type, the changes in pathway (X) expression over time (T) and with the addition of the PD-1 inhibitor (P) were examined. A random effects model with the following linear predictor (II) and error structure was constructed for each pathway:

$$E(ssGSEA[X])_i = \beta_0 + \beta_R R + \beta_T T + \beta_{TR} RT + \beta_{PT} PT + \beta_{PTR} RPT + u_i$$

$$ssGSEA[X]_{i,c} \sim \text{Normal}(E(ssGSEA[X])_i, \sigma_X^2)$$

$$u_i \sim \text{Normal}(0, \sigma_{u_i}^2)$$

Initial differences in gene set expression between immune cells from responders and non-responders, at the pre-treatment time point (C1), were captured by the group-specific intercepts ($\beta_0$ vs. $\beta_R$). Differential trends in expression over the first 5 treatment cycles were described by the group specific slope terms of responders and non-responders ($\beta_T$ vs $\beta_{TR}$). Differential effects of the addition of PD-1i on gene expression, over cycle C3-C5, were described by the group specific PD-1i treatment effect terms of responders and non-responders ($\beta_{PT}$ vs $\beta_{PTR}$).

Consistent and considerable background differences in gene expression occur between individuals and are independent of the impacts of therapy. This interpatient variability was accounted for by allowing the model intercept to vary among patients ($u_i$). Significant differences in: A) initial pathway scores, B) temporal trend and C) PD-1i treatment effects between non-responders and responders were assessed using likelihood ratio tests. Multiple comparison corrections were made using Holm's p-value correction.

Pathways exhibiting significant differences in PD-1i treatment effects between responders and non-responders were examined and found to reflect four major processes: a) interferon signaling b) inflammatory response, c) growth factor production and d) differentiation. The trends in immune cell expression were predicted by producing the expectation across all significant ssGSEA pathways reflecting each process. Separate predictions were made for each immune cell type and for responders and non-responders. Pathway scores were normalized to the average score of each cell type at the initial sample (C1).

Quantifying Immune Cell Phenotypes

Major axes of phenotypic variation were identified separately for $CD4^{+/}CD8^+$ T cells and monocytes using Affinity-based pseudotime reconstruction of cell states [See for example Refs. 57, 58]. This allowed the description of continuous spectrums of cellular states, as is produced by differentiation and activation processes. It also allows complex nonlinear gene expression changes to be captured, despite the sparsity of transcripts (leading to dropout), the presence of normalization induced noise artifacts and the high levels of gene amplification noise that is present in all single cell datasets [See for example Ref. 59]. The full gene expression profile of the immune cell types was filtered to remove genes that had zero expression in more than 99% of cells. The first 150 principle components of this gene expression profile were then calculated and used to create a dissimilarity matrix (Euclidean distance) of gene expression between cells. Nearest neighbor distances were calculated for the 100 most similar cells and an exponential kernel was used to produce the local affinity matrix, which was normalized to give the Markov transition matrix between cells. The kernel decay rate (a) parameter was set to 10, to capture the local and global relatedness between cells (Parameter sensitivity was low but below 5 the global structure is lost and above 30 local structure is lost). Log transition probabilities were calculated and a reduce dimension embedding was created to visualize the first 5 major axes of phenotypic variation. Phenotypic axes were validated using comparisons to PCA, zinbwave, and UMAP dimension reduction [See for example Refs. 54, 60]. The same phenotypes were identified by all the dimension reduction techniques and the correspondence between the inferred phenotypic scores was high for all cell types. Random effects linear regression was used to test the statistical differences in immune population phenotype distributions between responders and non-responders, whilst accounting for patient-specific random effects.

Identifying Predictors of Patient Response to PD1 Therapy

Response to PD1 therapy was predicted based on immune cell number and composition. Measurements of peripheral blood mononuclear cell density (cells $\mu L^{-1}$) were obtained from blood draws, taken from each patient at each sampling time point (C1-C5). Immune cell subtype densities ($N_S$) were calculated for each patient sample, by multiplying the total PBMC density (N) by the proportion of scRNA sequenced cells belonging to each immune class.

Total PBMC density (N) and the density of immune subclasses ($N_s$) were used to predict patient response, using random effects logistic regression models:

$$\text{Repsonse}_i \sim Bern(logit^{-1}(\beta_0 + \beta_N N + \beta_s N_s + \beta_{SN} NN_s + u_{Time}))$$

$$u_{Time} \sim Normal(0, \sigma^2_{uTime})$$

A random effect of time ($u_{Time}$) was included to account for the non-independence of patients' responses when predicted by the immune composition at different time points. Sample size corrected Akaike information criterion (AIC) was used to compare the ability of differing components of the total immune cell density in predicting patient responses.

Flow Cytometry Antibodies and Immunophenotyping

This assay was performed by the UCLA Immune Assessment Core. PBMCs were stained with two different antibody panels. The first panel was used to phenotype antigen presenting cells and B cells using: IgM BV421 (clone MHM-88), CD11b BV510 (clone ICRF44), CD303 BV605 (clone 201A), HLA-DR BV650 (clone L243), CD1c BV711 (clone L161), CD16 BV785 (clone 3G8), CD33 FITC (clone P67.6), CD86 PE (clone IT2.2), CD141 PE-CY7 (clone M80), CD3 PECF594 (OKT3), CD14 PCP-CY5 (HCD14), CD19 APC (SJ25C1), CD11c Alexa700 (Bu15), CD27 APC-CY7 (M-T271), CD15 BUV395 (HI98), CD56 BUV737 (NCAM16.2). The second panel was used to phenotype T cell lineage using: CCR10 BV421 (clone 1B5), CCR7 BV510 (clone G043H7), CTLA4 BV605 (clone BNI3), CD3 BV650 (clone OKT3), PD-1 BV711 (clone EH12.2H7), CD4 FITC (clone RPA-T4), FOXP3 PE (clone PCH101), CD45RA PCP-CY5 (clone HI100), CXCR5 APC (clone J252D4), HLA-DR Alexa700 (clone LN3), CD8 APC-CY7 (clone SK1), Ki67 BUV395 (clone B56), CD25 BUV737 (clone 2A3). An average of $0.3\times10^6$ cells per cocktail were stained for 20 min at 4° C. with LIVE/DEAD Fixable Blue Dead Cell Stain Kit (Invitrogen), diluted 1:1000 in PBS. Cells were then washed once with flow cytometry buffer (2% FBS in PBS) and stained with fluorochrome-conjugated antibodies (BioLegend, BD Biosciences, eBioscience) for 20 minutes at 4° C. Finally, the cells were washed and re-suspended in 200 µL FACS buffer. At least 100,000 lymphocyte events per sample were acquired using DIVA 8.0 software on an LSRFortessa Cell Analyzer (BD Biosciences). Data analysis was performed using FlowJo v10.5.0 (Tree Star) by gating on live cells based on forward versus side scatter profiles, then gating on singlets using forward scatter area versus height, followed by dead cell exclusion using Live/Dead exclusion stain, and then cell subset-specific gating.

Intracellular Cytokine Staining

This assay was performed by the UCLA Immune Assessment Core. An average of $0.3\times10^6$ cells per cocktail were stained with 1:1000 LIVE/DEAD Fixable Blue Dead Cell Stain Kit (Invitrogen), diluted in PBS, for 20 min at 4° C. After washing with flow cytometry buffer (2% FBS in PBS), cells were stained for surface markers for 20 min at 4° C., washed again with FACS Buffer, then centrifuged at 1500 rpm for 5 minutes. Subsequently, cells were incubated for 45 minutes using FoxP3 fix/perm buffer (eBioscience) at 4° C. in the dark, washed twice with perm buffer (eBioscience), and centrifuged at 2000 rpm for 6 min. Antibodies specific to FoxP3, Ki67, and CTLA4 intracellular markers were then prepared in perm buffer and used to stain cells for 30 min at 4° C. Following two additional washes with perm buffer, cells were resuspended in flow cytometry buffer and 100,000 lymphocyte cell events per sample were collected using DIVA 8.0 software on an LSRFortessa Cell Analyzer (BD Biosciences). Data analysis was performed using FlowJo v10.5.0 (Tree Star) by gating on live cells based on forward versus side scatter profiles, then gating on singlets using forward scatter area versus height, followed by dead cell exclusion using Live/Dead exclusion stain, and then cell subset-specific gating.

Example 3

Patient Specific Immune Function Linked to Immunotherapy Success

Additional analyses were performed in connection with the experiments described in Examples 1 and 2. Time courses of tumor burden and immune abundance (PBMC) were constructed for each patient (FIG. 22i). Tumor burden was measured by combining information from cancer specific antigen biomarkers and RECIST 1.1 measurements of tumor size, using a Gaussian process latent variable model. The changes in patients' tumor burden and immune cell abundance during the trial were described mathematically by a dynamic model of cancer-immune cell interactions (FIG. 22ii). This model describes the interactions between populations of tumor and immune cells within a patient, with tumor cells (T) being attacked by immune cells (I) and inducing increased immune cell recruitment. Chemotherapy (C) kills both tumor and immune cells, whilst PD-1 inhibitor immunotherapy (P) impacts immune proliferation, recruitment and cytotoxic tumor activity (FIG. 23A).

Changes in tumor and immune cell abundance over time were accurately described by statistically fitting the mathematical model to the clinical data, using a Bayesian hierarchical approach (FIG. 23B). This captured the biological differences between tumor and immune populations of responders and non-responders and described the substantial variation between patients within response categories. Key biological rates were also estimated, including: a) how effectively immune cells attack the tumor and b) the impact of chemotherapy on tumor and immune populations. This identified the consistently improved ability of responder patients' immune cells to attack the tumor, compared to the non-responder (FIG. 23C).

The time periods of most rapid growth and decline of the tumor and immune populations were determined by analyzing the population's relative growth rates (RGR=speed of population change, positive=growth, negative=decline) (FIG. 23D-E). The response dynamics (described below) were not dependent on the patient's cancer tissue type. The tumor burden of the responders declined more rapidly during the chemotherapy phase and continued to decline (negative RGR) over most of the rest of the time on trial (FIG. 23D). The exception is a time window around day 100 when the immune population was still increasing but the chemotherapy effect was generally decreased. Once the immune cell abundance increased further, the tumor began to shrink once again. As a result, tumor burden of responders remained substantially below the pre-treatment level for the duration of the trial. Responders' PBMC's were also initially less abundant and more sensitive to chemotherapy (more negative RGR). However, their immune cell abundance was substantially boosted following the addition of immunotherapy (FIG. 23D; spike in PBMC's RGR around days 48-100). Their immune abundance the stabilized at this level or even increased gradually during the rest of the trial (with an overall positive RGR).

In contrast, the tumor burden of patients non-responsive to immunotherapy declined very little during the pre-immunotherapy chemotherapy phase, and only marginally in the first weeks of immunotherapy. Subsequently, tumor growth accelerated, and the tumor burden returned to the pre-treatment level within just 80-150 days. Non-responders also exhibited a continual decline in immune cell number (negative RGR over most of the trial) and did not experience the immunotherapy induced boost in immune population growth following the addition of immunotherapy (no spike between days 48-100). Analysis of the fitted mathematical model showed that prior to immunotherapy, the responders' immune populations less effectively regulated tumor growth (FIG. 23E). However, after immunotherapy induced the growth spike in the responders' immune cell population, these immune cells became more effective at regulating the tumor growth. In contrast, the ability of immune cells to regulate tumor growth declined continually during the trial and very little benefit of immunotherapy could be detected.

Overall Measures of Tumor Burden

We assessed the strength of tumor-immune cell interactions and the predictability of responsive to therapy, by fitting a coupled tumor-immune population model to clinical patient data. For each patient, a time series of tumor burden was first constructed, by combining RECIST 1.1 measurements, from CT scans, with information from tumor burden biomarkers (CA 19-9 and CEA), using a Gaussian process model [see, e.g., Ref. 69]. The RECIST1.1 data provides information about the absolute burden and the magnitude of changes during therapy, whilst blood biomarkers provides higher temporal resolution of the patterns of change. Gaussian process models probabilistically combine these tumor burden data sources, allowing inference of the most likely time course of tumor burden, given the available information.

Gaussian processes latent variable models were fitted to each patients' tumor time course data. A Bayesian priors of nonlinear functions was constructed to describe a wide range of different kinds of fluctuation in tumor burden that could have occurred. Then, using the Markov chain Monte Carlo, we infer a posterior that represents our belief about the fluctuations that are likely to have occurred, conditioned on observed data. Specifically, a multidimensional Gaussian, $F=(f_1 \ldots f_x) \sim N(\mu, \Sigma)$, {indices i=1 ... x}, was defined, with each of n dimensions describing the tumor burden at one of the time points at which either RECIST or blood biomarker data was available. The nonlinear function describing the tumor burden over time (f (t)) was then described as a Gaussian process: $f(t) \sim GP(m(x), k(x, x'))$, {indices x}, where m(x) is an n-vector and k(x, x') is an n×n covariance matrix. The covariance of tumor burden at different time points was calculated, using a squared exponential covariance function:

$$k(x)_{i,j} = \eta_2 \exp(-\rho \rho^2 \Sigma_{d=1}^{D}(x_{i,d}-x_{j,d})^2) + \delta_{i,j}\sigma^2.$$

Covariance function hyper-parameters ($\eta$, $\rho$) were estimated. To ensure a positive definite covariance matrix, $\rho^2$ was added to the diagonal elements, using $\delta$ as a Kronecker delta function with value 1 if i=j, but 0 otherwise. The summation of squared Euclidean distances in time results in smooth changes in tumor burden over time.

RECIST1.1 assessments of the volume of tracked lesions within a given patient ($R_p$) was assumed to be a lognormally distributed measurement of a fixed fraction of a patient's overall tumor burden: $R_p(t) \sim LogNormal(f_p(t), \sigma_{R_p})$. The two blood biomarkers were assumed to be produced by cancer cells at a constant rate, $\alpha$, degrade at rate $\lambda$ and to have a baseline production level within the healthy body of rate r. The dynamics of blood antigens can then be described as:

$$\frac{dM_x}{dt} = r + \alpha f_P(t) - \lambda M_x.$$

Applying steady state assumptions, the blood biomarkers were also expected to be lognormally distributed measurements such that:

$$M_{x_P}(t) \sim \text{Log Normal}(\beta_{x_P} f_P(t) + c_{x_P}, \sigma_{M_{x_P}}).$$

Bayesian sampling of these probabilistic models yielded overall time course estimates of tumor burden during the trial. Concurrent measurements of immune cell abundance and therapeutic dosages (immunotherapy and chemotherapy) were also curated.

Tumor-Immune Interaction Model

The dynamics of tumor and immune cell abundance were coupled with the immunotherapy and chemotherapy dosing schedules, using a patient specific tumor-immune population dynamic model. The model (Equ.1 below) describes the patient specific changes in tumor (T) and immune cell (I) abundance over time. Over short periods of time, the increase or decrease in tumor and immune cell abundance was measured by the populations relative growth rate ($RGR_T$ for tumor and $RGR_I$ for immune cells). Positive RGR values indicate population growth, whilst negative values show population decline. The data driven model decomposed this population growth rate into effects of different concurrent biological processes (described below). Tumor and immune cells interact in two main ways, with tumor cells being attacked by immune cells (α) and also inducing increased immune cell recruitment (λ). Therapeutic dosing also impacts the cell populations and the strength of their interactions, with chemotherapy (C) killing both tumor ($\vec{\mu_T}$) and immune cells ($\vec{\mu_I}$), whilst PD-1i immunotherapy (P) influences immune proliferation ($\beta_r$), recruitment ($\beta_\lambda$) and cytotoxic tumor killing activity ($\beta_\varphi$). Both tumor and immune cells experience density dependent population growth ($\gamma_T$ & $\gamma_I$), reflecting competition for resources or growth stimulating molecules. This leads to the equations:

$$RGR_T = \frac{1}{T}\frac{dT}{dt} = r_T(1 - \gamma_T T) - (\alpha + \beta_\varphi P)I - \sum_i \vec{\mu_T}[i]Ci, \quad \text{Equ. 1}$$

$$RGR_I = \frac{1}{I}\frac{dI}{dt} = (r_I + \beta_r P)(1 - \gamma_I I) + (\lambda + \beta_\lambda P)T - \sum_i \vec{\mu_I}[i]Ci$$

We simultaneously fitted this model to all of the patients' time course tumor and immune data, and accounted for the differing dosages and timings of therapy. To capture interpatient biological differences, patient specific parameters were assumed to be drawn from a hyper-distribution of parameters, creating a hierarchical model structure. Observation error in the populations' growth rates were assumed to be T distributed, to account for occasional large observed changes in tumor or immune measurements. Model parameters were estimated using Bayesian inference, with Hamiltonian Monte Carlo in Stan [see, e.g., Ref 70].

Linking Immune Phenotypes and Model Estimated Biological Processes

Immune cell phenotypes were related to the model estimates of: a) the effectiveness of immune cells at attacking tumor cells and b) the tumor cell sensitivity to chemotherapy. These biological estimates of immune and chemotherapy function (X) were regressed against the peripheral immune cell phenotypes identified in: i) the GSEA pathway analysis and ii) the pseudotime analysis of the major phenotypic variation within cell types. For each phenotype, the significance of the relationship between single cell peripheral immune phenotypes (Y) and immune/chemotherapy function (X) was assessed. A patient specific intercept was added to account for non-independence of cell phenotypes within a patient. The random effects regression model was:

Norm($\beta_0 + \beta_X X + u_{Time}$)

$u_i \sim$ Normal($0, \sigma_{u_i}^2$)

The significance of the relationship between peripheral phenotypes and immune/chemotherapy function was assessed using a likelihood ratio test, with the sample size corrected for the non-independence of data points.

Discussion

The input data to the predator-prey mathematical model included a) clinical measurements of tumor burden including CT imaging estimates and cancer specific antigen levels obtained during the trial and b) peripheral blood mononuclear immune cell (PBMC) counts obtained from periodic blood tests. These two data types provide time courses of the size of the tumor and the concurrent immune populations within a specific patient.

The first analysis involved looking across all available data on the size of the patients' tumor during the trial and estimating the most probable time course, using a Gaussian process latent variable model. The amount that a tumor grows or shrinks between two observation times is then assessed by a measurement called the relative growth rate. The same calculation can be made for the immune cell population size, to quantify how much the immune population is growing or shrinking over time.

REFERENCES

1. Loos, M. et al. Clinical significance and regulation of the costimulatory molecule B7-H1 in pancreatic cancer. *Cancer Lett* 268, 98-109, doi:10.1016/j.canlet.2008.03.056 (2008).
2. Nomi, T. et al. Clinical significance and therapeutic potential of the programmed death-1 ligand/programmed death-1 pathway in human pancreatic cancer. *Clin Cancer Res* 13, 2151-2157, doi:10.1158/1078-0432.CCR-06-2746 (2007).
3. Ohigashi, Y. et al. Clinical significance of programmed death-1 ligand-1 and programmed death-1 ligand-2 expression in human esophageal cancer. *Clin Cancer Res* 11, 2947-2953, doi:10.1158/1078-0432.CCR-04-1469 (2005).
4. Oki, E. et al. Protein Expression of Programmed Death 1 Ligand 1 and HER2 in Gastric Carcinoma. *Oncology* 93, 387-394, doi:10.1159/000479231 (2017).
5. Song, M. et al. PTEN loss increases PD-L1 protein expression and affects the correlation between PD-L1 expression and clinical parameters in colorectal cancer. *PLoS One* 8, e65821, doi:10.1371/journal.pone.0065821 (2013).
6. Wang, L. et al. Clinical significance of B7-H1 and B7-1 expressions in pancreatic carcinoma. *World J Surg* 34, 1059-1065, doi:10.1007/s00268-010-0448-x (2010).
7. Ye, Y. et al. Interaction of B7-H1 on intrahepatic cholangiocarcinoma cells with PD-1 on tumor-infiltrating T cells as a mechanism of immune evasion. *J Surg Oncol* 100, 500-504, doi:10.1002/jso.21376 (2009).
8. Zhang, M. Y., Yang, Y. Y., Wang, X. H. & Li, X. F. [Expression of Bcl-2, PD-L1 and its clinical significance in colorectal cancer]. *Sichuan Da Xue Xue Bao Yi Xue Ban* 43, 827-829, 859 (2012).
9. Ansell, S. M. et al. PD-1 blockade with nivolumab in relapsed or refractory Hodgkin's lymphoma. *N Engl J Med* 372, 311-319, doi:10.1056/NEJMoa1411087 (2015).
10. Garon, E. B. et al. Pembrolizumab for the treatment of non-small-cell lung cancer. *N Engl J Med* 372, 2018-2028, doi:10.1056/NEJMoa1501824 (2015).
11. Nghiem, P. T. et al. PD-1 Blockade with Pembrolizumab in Advanced Merkel-Cell Carcinoma. *N Engl J Med* 374, 2542-2552, doi:10.1056/NEJMoa1603702 (2016).
12. Yuan, Y. et al. Complete regression of cutaneous metastases with systemic immune response in a patient with triple negative breast cancer receiving p53MVA vaccine with pembrolizumab. *Oncoimmunology* 6, e1363138, doi:10.1080/2162402X.2017.1363138 (2017).
13. Palucka, A. K. & Coussens, L. M. The Basis of Oncoimmunology. *Cell* 164, 1233-1247, doi:10.1016/j.cell.2016.01.049 (2016).
14. Lynch, T. J. et al. Ipilimumab in combination with paclitaxel and carboplatin as first-line treatment in stage IIIB/IV non-small-cell lung cancer: results from a randomized, double-blind, multicenter phase II study. *J Clin Oncol* 30, 2046-2054, doi:10.1200/JCO.2011.38.4032 (2012).
15. Reck, M. et al. Ipilimumab in combination with paclitaxel and carboplatin as first-line therapy in extensive-disease-small-cell lung cancer: results from a randomized, double-blind, multicenter phase 2 trial. *Ann Oncol* 24, 75-83, doi:10.1093/annonc/mds213 (2013).
16. Rizvi, N. A. et al. Cancer immunology. Mutational landscape determines sensitivity to PD-1 blockade in non-small cell lung cancer. *Science* 348, 124-128, doi: 10.1126/science.aaa1348 (2015).
17. Samstein, R. M. et al. Tumor mutational load predicts survival after immunotherapy across multiple cancer types. *Nat Genet* 51, 202-206, doi:10.1038/s41588-018-0312-8 (2019).
18. Huang, A. C. et al. T-cell invigoration to tumour burden ratio associated with anti-PD-1 response. *Nature* 545, 60-65, doi:10.1038/nature22079 (2017).
19. Ayers, M. et al. IFN-gamma-related mRNA profile predicts clinical response to PD-1 blockade. *J Clin Invest* 127, 2930-2940, doi:10.1172/JCI91190 (2017).
20. Garris, C. S. et al. Successful Anti-PD-1 Cancer Immunotherapy Requires T Cell-Dendritic Cell Crosstalk Involving the Cytokines IFN-gamma and IL-12. *Immunity* 49, 1148-1161 e1147, doi:10.1016/j.immuni.2018.09.024 (2018).
21. Hamid, O. et al. Safety and tumor responses with lambrolizumab (anti-PD-1) in melanoma. *N Engl J Med* 369, 134-144, doi:10.1056/NEJMoa1305133 (2013).
22. Topalian, S. L. et al. Safety, activity, and immune correlates of anti-PD-1 antibody in cancer. *N Engl J Med* 366, 2443-2454, doi:10.1056/NEJMoa1200690 (2012).
23. Powles, T. et al. MPDL3280A (anti-PD-L1) treatment leads to clinical activity in metastatic bladder cancer. *Nature* 515, 558-562, doi:10.1038/nature13904 (2014).
24. Llosa, N. J. et al. The vigorous immune microenvironment of microsatellite instable colon cancer is balanced by multiple counter-inhibitory checkpoints. *Cancer Discov* 5, 43-51, doi:10.1158/2159-8290.CD-14-0863 (2015).
25. Le, D. T. et al. Mismatch repair deficiency predicts response of solid tumors to PD-1 blockade. *Science* 357, 409-413, doi: 10.1126/science.aan6733 (2017).
26. Grosso, J. et al. Association of tumor PD-L1 expression and immune biomarkers with clinical activity in patients (pts) with advanced solid tumors treated with nivolumab (anti-PD-1; BMS-936558; ONO-4538). *Journal of Clinical Oncology* 31, 3016-3016, doi:10.1200/jco.2013.31.15_suppl.3016 (2013).
27. Carbone, D. P. et al. First-Line Nivolumab in Stage IV or Recurrent Non-Small-Cell Lung Cancer. *N Engl J Med* 376, 2415-2426, doi:10.1056/NEJMoa1613493 (2017).
28. Krieg, C. et al. High-dimensional single-cell analysis predicts response to anti-PD-1 immunotherapy. *Nat Med* 24, 144-153, doi:10.1038/nm.4466 (2018).
29. Sade-Feldman, M. et al. Defining T Cell States Associated with Response to Checkpoint Immunotherapy in Melanoma. *Cell* 175, 998-1013 e1020, doi:10.1016/j.cell.2018.10.038 (2018).
30. Azizi, E. et al. Single-Cell Map of Diverse Immune Phenotypes in the Breast Tumor Microenvironment. *Cell* 174, 1293-1308 e1236, doi:10.1016/j.cell.2018.05.060 (2018).
31. Rinder, H. M., Bonan, J. L., Rinder, C. S., Ault, K. A. & Smith, B. R. Activated and unactivated platelet adhesion to monocytes and neutrophils. *Blood* 78, 1760-1769 (1991).
32. Hanzelmann, S., Castelo, R. & Guinney, J. GSVA: gene set variation analysis for microarray and RNA-seq data. *BMC Bioinformatics* 14, 7, doi:10.1186/1471-2105-14-7 (2013).
33. Liberzon, A. et al. The Molecular Signatures Database (MSigDB) hallmark gene set collection. *Cell Syst* 1, 417-425, doi:10.1016/j.cels.2015.12.004 (2015).
34. Liberzon, A. et al. Molecular signatures database (MSigDB) 3.0. *Bioinformatics* 27, 1739-1740, doi: 10.1093/bioinformatics/btr260 (2011).
35. Wang, Y. et al. Negative feedback regulation of IFN-gamma pathway by IFN regulatory factor 2 in esophageal cancers. *Cancer Res* 68, 1136-1143, doi:10.1158/0008-5472.CAN-07-5021 (2008).
36. Schroder, K., Hertzog, P. J., Ravasi, T. & Hume, D. A. Interferon-gamma: an overview of signals, mechanisms and functions. *J Leukoc Biol* 75, 163-189, doi:10.1189/jlb.0603252 (2004).
37. Shi, C. & Pamer, E. G. Monocyte recruitment during infection and inflammation. *Nat Rev Immunol* 11, 762-774, doi:10.1038/nri3070 (2011).
38. Wherry, E. J. T cell exhaustion. *Nat Immunol* 12, 492-499 (2011).
39. Herbst, R. S. et al. Predictive correlates of response to the anti-PD-L1 antibody MPDL3280A in cancer patients. *Nature* 515, 563-567, doi:10.1038/nature14011 (2014).
40. Shi, J. et al. PD-1 Controls Follicular T Helper Cell Positioning and Function. *Immunity* 49, 264-274 e264, doi:10.1016/j.immuni.2018.06.012 (2018).
41. Sharma, P., Hu-Lieskovan, S., Wargo, J. A. & Ribas, A. Primary, Adaptive, and Acquired Resistance to Cancer Immunotherapy. *Cell* 168, 707-723, doi:10.1016/j.cell.2017.01.017 (2017).
42. Reading, J. L. & Quezada, S. A. Too Much of a Good Thing? Chronic IFN Fuels Resistance to Cancer Immunotherapy. *Immunity* 45, 1181-1183, doi:10.1016/j.immuni.2016.12.004 (2016).
43. Dosset, M. et al. PD-1/PD-L1 pathway: an adaptive immune resistance mechanism to immunogenic chemotherapy in colorectal cancer. *Oncoimmunology* 7, e1433981, doi:10.1080/2162402X.2018.1433981 (2018).
44. Kamphorst, A. O. et al. Proliferation of PD-1$^+$ CD8 T cells in peripheral blood after PD-1-targeted therapy in lung cancer patients. *Proc Natl Acad Sci USA* 114, 4993-4998, doi:10.1073/pnas.1705327114 (2017).
45. Yang, P., Ma, J., Yang, X. & Li, W. Peripheral CD4$^+$ naive/memory ratio is an independent predictor of survival in non-small cell lung cancer. *Oncotarget* 8, 83650-83659, doi:10.18632/oncotarget.19330 (2017).
46. Peguillet, I. et al. High numbers of differentiated effector CD4 T cells are found in patients with cancer and correlate with clinical response after neoadjuvant therapy of breast cancer. *Cancer Res* 74, 2204-2216, doi:10.1158/0008-5472.CAN-13-2269 (2014).
47. Verma, R. et al. Lymphocyte depletion and repopulation after chemotherapy for primary breast cancer. *Breast Cancer Res* 18, 10, doi:10.1186/s13058-015-0669-x (2016).
48. Palma, M. et al. T cells in chronic lymphocytic leukemia display dysregulated expression of immune checkpoints and activation markers. *Haematologica* 102, 562-572, doi:10.3324/haematol.2016.151100 (2017).
49. Dobin, A. et al. STAR: ultrafast universal RNA-seq aligner. *Bioinformatics* 29, 15-21, doi:10.1093/bioinformatics/bts635 (2013).
50. Butler, A., Hoffman, P., Smibert, P., Papalexi, E. & Satija, R. Integrating single-cell transcriptomic data across different conditions, technologies, and species. *Nat Biotechnol* 36, 411-420, doi:10.1038/nbt.4096 (2018).

51. Tirosh, I. et al. Dissecting the multicellular ecosystem of metastatic melanoma by single-cell RNA-seq. *Science* 352, 189-196, doi:10.1126/science.aad0501 (2016).
52. Newman, A. M. et al. Robust enumeration of cell subsets from tissue expression profiles. *Nat Methods* 12, 453-457, doi:10.1038/nmeth.3337 (2015).
53. De Simone, M. et al. Transcriptional Landscape of Human Tissue Lymphocytes Unveils Uniqueness of Tumor-Infiltrating T Regulatory Cells. *Immunity* 45, 1135-1147, doi:10.1016/j.immuni.2016.10.021 (2016).
54. McInnes, L., Healy, J. & Melville, J. UMAP: Uniform Manifold Approximation and Projection for Dimension Reduction. arXiv e-prints (2018). ui.adsabs.harvard.edu/Wabs/2018arXiv180203426M.
55. Finak, G. et al. MAST: a flexible statistical framework for assessing transcriptional changes and characterizing heterogeneity in single-cell RNA sequencing data. *Genome Biology* 16, 278, doi:10.1186/s13059-015-0844-5 (2015).
56. Bischl, B. mlr: Machine Learning in R. *Journal of Machine Learning Research* (2016).
57. Moon, K. R. Manifold learning-based methods for analyzing single-cell RNA-sequencing data. *Current Opinion in Systems Biology* 7, 36-46, doi:10.1016/j.coisb.2017.12.008 (2017).
58. van Dijk, D. et al. Recovering Gene Interactions from Single-Cell Data Using Data Diffusion. *Cell* 174, 716-729 e727, doi:10.1016/j.cell.2018.05.061 (2018).
59. Moon, K. R. et al. Visualizing Transitions and Structure for Biological Data Exploration. *bioRxiv*, 120378, doi:10.1101/120378 (2018).
60. Risso, D., Perraudeau, F., Gribkova, S., Dudoit, S. & Vert, J. P. A general and flexible method for signal extraction from single-cell RNA-seq data. *Nat Commun* 9, 284, doi:10.1038/s41467-017-02554-5 (2018).
61. Sambrook, et al., Molecular Cloning: A Laboratory Manual (3rd Edition, 2001)
62. Sambrook, et al., Molecular Cloning: A Laboratory Manual (2nd Edition, 1989)
63. Maniatis et al., Molecular Cloning: A Laboratory Manual (1982); Ausubel et al.
64. Current Protocols in Molecular Biology (John Wiley and Sons, updated July 2008
65. Short Protocols in Molecular Biology: A Compendium of Methods from Current Protocols in Molecular Biology, Greene Pub. Associates and Wiley-Interscience
66. Glover, DNA Cloning: A Practical Approach, vol. I & II (IRL Press, Oxford, 1985)
67. Anand, Techniques for the Analysis of Complex Genomes, (Academic Press, New York, 1992)
68. Hames, B. S. Higgins, S. Transcription and Translation (Eds., 1984)
69. N. Lawrence, Probabilistic non-liner component analysis with Gaussian process latent variable models. *Journal of Machine Learning Research* 6, 1783-1816 (2005).
70. B. Carpenter, A. Gelman, M. D. Hoffman, D. Lee, B. Goodrich, M. Betancourt, M. Brubaker, J. Guo, P. Li, A. Riddell, Stan: A Probabilistic Programming Language. 2017 76, 32 (2017).

EMBODIMENTS

In various aspects, the present disclosure provides the following illustrative embodiments.

Embodiment 1. A method comprising detecting one or more parameters in a sample of peripheral blood from a subject with cancer, comprising detecting: (i) gene expression in monocytes comprising (1) increased expression of one or more of NFKB1, MYD88, NFKBIA or NFKBIZ, (2) decreased expression of IKBKB, (3) increased expression of one or more of growth factor genes, and/or (4) increased expression of one or more TNF genes, compared to a control; (ii) a greater number of $CD8^+$ differentiated cells, a greater number of $CD4^+$ naive cells, fewer $CD4^+$ differentiated cells, and fewer T follicular helper ($T_{FH}$) cells compared to a control; or (iii) a lower density of total peripheral blood mononuclear cells, a lower density of $CD4^+$ effector memory (EM) cells, and a higher density of classical monocytes compared to a control.

Embodiment 2. A method of identifying a cancer of a subject as responsive to treatment with a PD-1 inhibitor, the method comprising detecting one or more parameters in a sample of peripheral blood from the subject, comprising detecting: (i) gene expression in monocytes comprising (1) increased expression of one or more of NFKB1, MYD88, NFKBIA or NFKBIZ, (2) decreased expression of IKBKB, (3) increased expression of one or more of growth factor genes, and/or (4) increased expression of one or more TNF genes, compared to a control; (ii) a greater number of $CD8^+$ differentiated cells, a greater number of $CD4^+$ naive cells, fewer $CD4^+$ differentiated cells, and fewer T follicular helper ($T_{FH}$) cells compared to a control; or (iii) a lower density of total peripheral blood mononuclear cells, a lower density of $CD4^+$ effector memory (EM) cells, and a higher density of classical monocytes compared to a control.

Embodiment 3. A method for treating cancer in a subject comprising: (a) detecting one or more parameters in a sample of peripheral blood from the subject, comprising detecting: (i) gene expression in monocytes comprising (1) increased expression of one or more of NFKB1, MYD88, NFKBIA or NFKBIZ, (2) decreased expression of IKBKB, (3) increased expression of one or more of growth factor genes, and/or (4) increased expression of one or more TNF genes, compared to a control; (ii) a greater number of $CD8^+$ differentiated cells, a greater number of $CD4^+$ naive cells, fewer $CD4^+$ differentiated cells, and fewer T follicular helper ($T_{FH}$) cells compared to a control; or (iii) a lower density of total peripheral blood mononuclear cells, a lower density of $CD4^+$ effector memory (EM) cells, and a higher density of classical monocytes compared to a control; and (b) identifying the cancer as responsive to treatment with a PD-1 inhibitor if the cancer has one or more of the parameters (i)-(iii).

Embodiment 4. The method of any one of embodiments 1-3, further comprising detecting one or more of the following parameters: (iv) increased expression in T cells of one or more cell death genes compared to a control; (v) greater number of CTLA4+$CD4^+$ EM cells and PD-1+$CD8^+$ cells compared to a control; (vi) greater number of classical, CD86+, and HLADR+ monocytes as measured by florescence-activated cell sorting (FACS) and compared to a control; and (vii) fewer CD4+EM cells and a greater number of CLT4+$CD4^+$ EM cells as measured by FACS and compared to a control.

Embodiment 5. The method of any one of embodiments 1-4, further comprising selecting a PD-1 inhibitor for administration to the subject, and optionally treating the subject with the PD-1 inhibitor, if one or more of the parameters (i)-(vii) is detected.

Embodiment 6. The method of embodiment 4, wherein two, three, four, five, six, or seven of the parameters (i)-(vii) are detected.

Embodiment 7. The method of embodiment 4, wherein all of the parameters (i)-(vii) are detected.

Embodiment 8. The method of embodiment 4, wherein all of the parameters (i)-(iii) are detected.

Embodiment 9. The method of any one of embodiments 1-8, wherein the one or more growth factor genes comprise one or more of FOS, JUN, or JUNB.

Embodiment 10. The method of any one of embodiments 1-9, wherein the one or more TNF genes comprise one or more of TNF, TNFAIP2, or TNFAIP3.

Embodiment 11. The method of any one of embodiments 4-10, wherein the one or more cell death genes comprise one or more of CASP1, CASP3, CASP7, or CASP8.

Embodiment 12. The method of any one of embodiments 1-11, further comprising selecting the subject for anticancer therapy if the cancer is not identified as responsive to treatment with a PD-1 inhibitor; and optionally administering the anticancer therapy to the subject.

Embodiment 13. The method of embodiment 12, wherein the anticancer therapy comprises one or more of radiation therapy, chemotherapy, surgery, or immunotherapy.

Embodiment 14. The method of any one of embodiments 12 or 13, further comprising administering the anticancer therapy to the subject.

Embodiment 15. The method of any one of embodiments 2-14, wherein the PD-1 inhibitor is a PD-1 antibody.

Embodiment 16. The method of embodiment 15, wherein the PD-1 antibody is one or more of pembrolizumab, nivolumab, or cemiplimab.

Embodiment 17. The method of any one of embodiments 1-16, further comprising treating the subject with an anticancer therapy other than a PD-1 inhibitor.

Embodiment 18. The method of any one of embodiments 1-17, wherein the cancer is gastrointestinal cancer.

Embodiment 19. The method of embodiment 18, wherein the gastrointestinal cancer is selected from colorectal cancer, gastroesophogeal cancer, pancreatic cancer, and biliary cancer.

Embodiment 20. The method of any one of embodiments 1-19, wherein detecting gene expression comprises one or more of single-cell RNA sequencing, single sample gene set enrichment analysis, Northern blotting, fluorescent in situ hybridization, reverse transcription polymerase chain reaction (RT-PCR), serial analysis of gene expression (SAGE), microarray, or tiling arrays.

Embodiment 21. The method of any one of embodiments 1-20, wherein detecting a number of cells as fewer or greater than a control comprises one or more of single-cell RNA sequencing, affinity-based pseudotime reconstruction, flow cytometry or immunophenotyping.

Embodiment 22. A method comprising detecting one or more parameters in a sample of peripheral blood from a subject with cancer previously treated with a PD-1 inhibitor, comprising detecting: (i) in T cells, (1) increased expression of one or more interferon type I or type II signaling genes, (2) increased expression one or more of NFKB1, MYD88, NFKBIA or NFKBIZ, (3) increased expression of one or more major histocompatibility complex (MHC) class I or class II processing genes, (4) increased expression of one or more of CCL3, CCL4, CCL5, and CCR5, (5) decreased expression of one or more of CXCR3 or CCR2 genes, (6) increased expression in CD8$^+$ T cells of one or more cell death genes, (7) a greater number of differentiated CD8$^+$ cells, and/or (8) fewer differentiated CD4$^+$ cells compared to a control; or (ii) in monocytes, (1) increased expression of genes upregulated by IFN stimulation, and/or (2) increased expression of genes upregulated by major histocompatibility complex 2 (MHCII) production.

Embodiment 23. A method of identifying a cancer of a subject previously treated with a PD-1 inhibitor as responsive to treatment with the PD-1 inhibitor, the method comprising detecting one or more parameters in a sample of peripheral blood from the subject, comprising detecting: (i) in T cells, (1) increased expression of one or more interferon type I or type II signaling genes, (2) increased expression one or more of NFKB1, MYD88, NFKBIA or NFKBIZ, (3) increased expression of one or more major histocompatibility complex (MHC) class I or class II processing genes, (4) increased expression of one or more of CCL3, CCL4, CCL5, and CCR5, (5) decreased expression of one or more of CXCR3 or CCR2 genes, (6) increased expression in CD8$^+$ T cells of one or more cell death genes, (7) a greater number of differentiated CD8$^+$ cells, and/or (8) fewer differentiated CD4$^+$ cells compared to a control; or (ii) in monocytes, (1) increased expression of genes upregulated by IFN stimulation, and/or (2) increased expression of genes upregulated by major histocompatibility complex 2 (MHCII) production.

Embodiment 24. A method of monitoring response to PD-1 immunotherapy in a subject previously treated with a PD-1 inhibitor, the method comprising: (a) detecting one or more parameters in a sample of peripheral blood from the subject, comprising detecting: (i) in T cells, (1) increased expression of one or more interferon (IFN) type I or type II signaling genes, (2) increased expression one or more of NFKB1, MYD88, NFKBIA or NFKBIZ, (3) increased expression of one or more major histocompatibility complex (MHC) class I or class II processing genes, (4) increased expression of one or more of CCL3, CCL4, CCL5, and CCR5, (5) decreased expression of one or more of CXCR3 or CCR2 genes, (6) increased expression in CD8$^+$ T cells of one or more cell death genes, (7) a greater number of differentiated CD8$^+$ cells, and/or (8) fewer differentiated CD4$^+$ cells compared to a control; or (ii) in monocytes, (1) increased expression of genes upregulated by IFN stimulation, and/or (2) increased expression of genes upregulated by major histocompatibility complex 2 (MHCII) production compared to a control; and (b) identifying the cancer as responsive to continued treatment with the PD-1 inhibitor if one or both of parameters (i) and (ii) are detected.

Embodiment 25. The method of any one of embodiments 22-24, wherein the IFN signaling genes comprise one or more genes of FIGS. 17A-C, optionally including one or more of IFIT1/3, IFITM3, IFI44L, PSME2, IFI6, ISG15.

Embodiment 26. The method of any one of embodiments 22-25, wherein the MHC I processing genes comprise one or more of PIK3CD, PSMA7, PSMB8, PSMD9, HLA-A, HLA-B, or HLA-C.

Embodiment 27. The method of any one of embodiments 22-26, wherein the MHC II processing genes comprise one or more of HLA-DQB1, HLA-DQA1, HLA-DPB1, HLA-DPA1, HLA-DRB1, HLA-DRA, HLA-DMB, or HLA-DMA.

Embodiment 28. The method of any one of embodiments 22-27, wherein detecting gene expression comprises one or more of single-cell RNA sequencing, single sample gene set enrichment analysis, Northern blotting, fluorescent in situ hybridization, reverse transcription polymerase chain reaction (RT-PCR), serial analysis of gene expression (SAGE), microarray, or tiling arrays.

Embodiment 29. The method of any one of embodiments 22-28, wherein detecting a number of cells as fewer or greater than a control comprises one or more of single-cell RNA sequencing, affinity-based pseudotime reconstruction, flow cytometry or immunophenotyping.

Embodiment 30. The method of any one of embodiments 22-29, further comprising administering one or more doses of a PD-1 inhibitor after the detecting.

Embodiment 31. The method of any one of embodiments 22-30, wherein the PD-1 inhibitor is a PD-1 antibody.

Embodiment 32. The method of embodiment 31, wherein the PD-1 antibody comprises one or more of pembrolizumab, nivolumab, or cemiplimab.

Embodiment 33. The method of any one of embodiments 22-32, further comprising selecting the subject for anticancer therapy if the cancer is not identified as responsive to continued treatment with the PD-1 inhibitor, and optionally administering the anticancer therapy to the subject.

Embodiment 34. The method of embodiment 33, wherein the anticancer therapy comprises one or more of radiation therapy, chemotherapy, surgery, or immunotherapy.

Embodiment 35. The method of any one of embodiments 30-34, comprising administering the anticancer therapy to the subject.

Embodiment 36. The method of any one of embodiments 22-35, wherein the cancer is gastrointestinal cancer.

Embodiment 37. The method of embodiment 36, wherein the gastrointestinal cancer is selected from colorectal cancer, gastroesophogeal cancer, pancreatic cancer, and biliary cancer.

Embodiment 38. A system comprising: (a) at least one processor; and (b) at least one memory including program code which when executed by the at least one memory provides operations for performing a method according to any of the preceding embodiments.

Embodiment 39. The system of embodiment 38, wherein the operations include: (i) collecting gene expression data associated with a subject; (ii) collecting cell density data associated with a subject; and (iii) providing, via a user interface, a prognosis for the subject based at least in part on detected gene expression and/or cell density.

Embodiment 40. A method of monitoring response to PD-1 immunotherapy in a subject previously treated with a PD-1 inhibitor, the method comprising: (a) detecting an increase in peripheral blood mononuclear cells (PBMCs) in a sample of peripheral blood from the subject compared to a control; (b) detecting a reduced rate of tumor growth compared to a control, comprising measuring tumor size and/or a level of one or more tumor antigens; and, (c) identifying the cancer as responsive to continued treatment with the PD-1 inhibitor if both of parameters (a) and (b) are detected.

Embodiment 41. The method of embodiment 40, further comprising administering one or more doses of a PD-1 inhibitor after the detecting.

Embodiment 42. The method of embodiment 40, further comprising selecting the subject for anticancer therapy if the cancer is not identified as responsive to continued treatment with the PD-1 inhibitor, and optionally administering the anticancer therapy to the subject.

What is claimed is:

1. A method comprising detecting in a sample of peripheral blood from a subject with cancer:
   increased expression of three or more of TNF, FOS, JUN, JUNB, TNFAIP2, TNFAIP3, NFKB1, NFKBIA or NFKBIZ compared to a control;
   and treating the subject with a PD-1 inhibitor.

2. The method of claim 1, further comprising detecting
   (a) decreased expression of IKBKB, compared to a control;
   (b) a greater number of $CD8^+$ differentiated cells, a greater number of $CD4^+$ naive cells, fewer $CD4^+$ differentiated cells, and fewer T follicular helper ($T_{FH}$) cells compared to a control; or
   (c) a lower density of total peripheral blood mononuclear cells, a lower density of CD4+ effector memory (EM) cells, and a higher density of classical monocytes compared to a control.

3. The method of claim 2, further comprising detecting one or more of the following parameters:
   increased expression in T cells of one or more cell death genes compared to a control;
   greater number of $CTLA4^+CD4^+EM$ cells and $PD-1^+$ $CD8^+$ cells compared to a control;
   greater number of classical, $CD86^+$, and HLADR+ monocytes as measured by florescence-activated cell sorting (FACS) and compared to a control; and
   fewer $CD4^+EM$ cells and a greater number of $CLT4^+$ $CD4^+EM$ cells as measured by FACS and compared to a control.

4. The method of claim 3,
   wherein the one or more cell death genes comprise one or more of CASP1, CASP3, CASP7, or CASP8.

5. The method of claim 1, wherein (a) the PD-1 inhibitor is a PD-1 antibody; (b) the PD-1 inhibitor is one or more of pembrolizumab, nivolumab, or cemiplimab; or (c) the method further comprises treating the subject with an anticancer therapy other than a PD-1 inhibitor.

6. The method of claim 1, wherein the cancer is (a) gastrointestinal cancer; or (b) colorectal cancer, gastroesophogeal cancer, pancreatic cancer, or biliary cancer.

7. The method of claim 1, wherein:
   (a) detecting gene expression comprises one or more of single-cell RNA sequencing, single sample gene set enrichment analysis, Northern blotting, fluorescent in situ hybridization, reverse transcription polymerase chain reaction (RT-PCR), serial analysis of gene expression (SAGE), microarray, or tiling arrays; or
   (b) detecting a number of cells as fewer or greater than a control comprises one or more of single-cell RNA sequencing, affinity-based pseudotime reconstruction, flow cytometry or immunophenotyping.

* * * * *

UNITED STATES PATENT AND TRADEMARK OFFICE
CERTIFICATE OF CORRECTION

Page 1 of 1

PATENT NO. : 11,708,612 B2
APPLICATION NO. : 17/110067
DATED : July 25, 2023
INVENTOR(S) : Andrea Bild and Jason I. Griffiths It is certified that error appears in the above-identified patent and that said Letters Patent is hereby corrected as shown below:

On the Title Page

At Item (73) under Assignee, delete:
"NATIONAL INSTITUTES OF HEALTH (NIH), U.S. DEPT. OF HEALTH AND HUMAN SERVICES (DHHS), U.S. GOVERNMENT, Bethesda, MD (US)"
And replace it with:
-- CITY OF HOPE, Duarte, CA (US) --

Signed and Sealed this
Seventh Day of January, 2025

Derrick Brent
*Acting Director of the United States Patent and Trademark Office*